(12) United States Patent
Jalagam et al.

(10) Patent No.: US 11,072,626 B2
(45) Date of Patent: Jul. 27, 2021

(54) SMALL MOLECULE INHIBITORS OF GALECTIN-3

(71) Applicant: BRISTOL-MYERS SQUIBB COMPANY, Princeton, NJ (US)

(72) Inventors: Prasada Rao Jalagam, Bangalore (IN); Satheesh Kesavan Nair, Bangalore (IN); Manoranjan Panda, Bangalore (IN); Alicia Regueiro-Ren, New Hope, PA (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 16/754,381

(22) PCT Filed: Oct. 10, 2018

(86) PCT No.: PCT/US2018/055192
§ 371 (c)(1),
(2) Date: Apr. 8, 2020

(87) PCT Pub. No.: WO2019/075045
PCT Pub. Date: Apr. 18, 2019

(65) Prior Publication Data
US 2020/0308213 A1 Oct. 1, 2020

Related U.S. Application Data

(60) Provisional application No. 62/570,821, filed on Oct. 11, 2017.

(51) Int. Cl.
| C07H 19/056 | (2006.01) |
| C07H 19/052 | (2006.01) |
| C07H 19/24 | (2006.01) |

(52) U.S. Cl.
CPC ......... *C07H 19/056* (2013.01); *C07H 19/052* (2013.01); *C07H 19/24* (2013.01)

(58) Field of Classification Search
None
See application file for complete search history.

(56) References Cited

U.S. PATENT DOCUMENTS

2014/0099319 A1   4/2014   Traber

FOREIGN PATENT DOCUMENTS

| WO | WO2005113568 A1 | 12/2005 |
| WO | WO2005113569 A1 | 12/2005 |
| WO | WO2014067986 A1 | 5/2014 |
| WO | WO2016120403 A1 | 8/2016 |
| WO | WO2017080973 A1 | 5/2017 |

OTHER PUBLICATIONS

DeBoer, et al., "Galectin-3 in Cardiac Remodeling and Heart", Curr Heart Fail Rep (2010) 7:1-8.
Guigure,et al. "Inhibitory potential of chemical substitutions at bioinspired sites of b-D-galactopyranose on neoglycoprotein/cell surface binding of two classes of medically relevant lectins", Bioorganic & Medicinal Chemistry vol. 19, 3280-3287, (2011).
Henderson et al., "Galectin-3 Expression and Secretion LinksMacrophages to the Promotion of Renal Fibrosis", American Journal of Pathology, vol. 172(2), pp. 288-298 (2008).
Henderson et al., "Galectin-3 regulates myofibroblast activationand hepatic fibrosis", PNAS, vol. 103(13) pp. 5060-65 (2006).
Jarvis, et al., "Galectin-3C: Human Lectin for Treatment of Cancer" ACS Symposium Series, vol. 1115. Chapter 12, pp. 195-23 (2012).
MacKinnon, et al., "Regulation of Transforming Growth Factorb1-driven Lung Fibrosis by Galectin-3", Am J Respir Crit Care Med vol. 185, Iss. 5, pp. 537-546 (2012).
U.S. Appl. No. 16/650,403, filed Mar. 25, 2020, Jalagam et al.

*Primary Examiner* — Layla D Berry

(74) *Attorney, Agent, or Firm* — Jing G. Sun

(57) ABSTRACT

The present disclosure relates to compounds of formula I, which inhibit Gal-3, and include pharmaceutically acceptable salts, compositions comprising such compounds, and methods using and making such compounds and compositions.

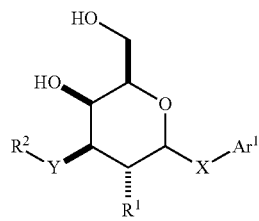

20 Claims, No Drawings

SMALL MOLECULE INHIBITORS OF GALECTIN-3

CROSS REFERENCE TO RELATED APPLICATION

This application is a 371 of International Application No. PCT/US2018/055192 filed on Oct. 10, 2018, which claims the benefit of U.S. Provisional Application 62/570,821 filed Oct. 11, 2017, the entire content of which is incorporated herein by reference in its entirety.

BACKGROUND OF THE INVENTION

Galectin-3 (Gal-3) is a β-galactoside binding lectin of about 30 KDa (Cell 76: 597-598), that is involved in the regulation of inflammatory and fibrotic processes. (Immunological Reviews 230: 160-171). Under uncontrolled inflammation and profibrotic condition, Gal-3 promotes fibroblast proliferation and transformation and mediates collagen production (Circulation 110:3121-3128).

Gal-3 is localyzed in many cellular location such as cytoplasm, nucleus, and cell surface. Gal-3 is also secreted by various cell types, mainly macrophages and monocytes into the blood stream (J Pharmacol Exp Ther 351:336-343). There are multiple lines of evidence in the literature supporting the involment of Gal-3 in the development of fibrotic process in multiple organs such as lung (Am J. Respir. Crit. Care Med. 185: 537-546), liver (PNAS 103:5060-5065) and kidney (Am. J. Pathol. 172:288-298). Gal-3 has also been identified as a biomarker for heart failure indicating that modulation of Gal-3 has potential uses in the treatment of heart failure (Curr. Heart Fail. Rep. 7:1-8). Modulation of Gal-3 can be used in the treatment of cancer since Gal-3 is involved in cell growth and differentiation playing a critical role in angiogenic, apoptotic, and metastatic pathways (Galectin-3C: Human Lectin for Treatment of Cancer. ACS Symposium Series, Vol. 1115. Chapter 12, 195-23). Recently, Gal-3 inhibitors have proven to have positive effects when used in combination immunotherapy (Galectin Therapeutics. Press Release, Feb. 7, 2017).

Several publications and patent applications describe synthetic inhibitors of Gal-3 that are being explored as antifibrotic agents. Recent examples of these approach are WO2005113568, WO2005113569, US2014067986, WO2014067986, WO2017080971, WO2016120403, US20140099319 and WO2014067986.

DESCRIPTION OF THE INVENTION

The present disclosure relates to compounds of formula I, which inhibit Gal-3, and include pharmaceutically acceptable salts, compositions comprising such compounds, and methods using and making such compounds and compositions.

One aspect of the invention is a compound of formula I

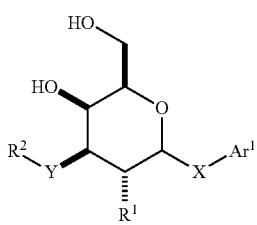

I where:
$Ar^1$ is phenyl, pyridinyl, indolyl, indazolyl, benzimidazolyl, benzoxazolyl, benzothiazolyl, or benzodioxolyl, and is substituted with 0-5 substituents selected from cyano, halo, alkyl, haloalkyl, alkoxy, and haloalkoxy;
or $Ar^1$ is pyrrolyl, furanyl, thienyl, pyrazolyl, isoxazolyl, isothiazolyl, imidazolyl, oxazolyl, thiazolyl, triazolyl, oxadiazolyl, or thiadiazolyl, and is substituted with 0-1 substituents selected from cyano, halo, alkyl, haloalkyl, alkoxy, and haloalkoxy;
$Ar^2$ is phenyl or pyridinyl and is substituted with 0-5 substituents selected from cyano, halo, alkyl, $(R^3)$alkyl, haloalkyl, cycloalkyl, $(R^3)$cycloalkyl, alkoxy, cycloalkoxy, haloalkoxy, and alkoxycarbonyl;
$R^1$ is hydrogen, halo, alkoxy, cyanoalkoxy, hydroxyalkoxy, alkoxyalkyl, $(R^4)$alkoxy, or $(R^4)$alkenyloxy;
$R^2$ is alkyl, cycloalkyl, alkoxycarbonyl, carboxy, $CON(R^{12})(R^{13})$, or $Ar^2$;
$R^3$ is cyano, halo, alkoxy, or $(R^5)(R^6)N$;
$R^4$ is $(R^7)(R^8)N$, $CO_2(R^9)$, or $CON(R^{10})(R^{11})$;
$R^5$ is hydrogen or alkyl;
$R^6$ is hydrogen or alkyl;
or $(R^5)(R^6)N$ taken together is azetidinyl, pyrrolidinyl, piperidinyl, piperazinyl, morpholinyl, thiomorpholinyl, (oxo)thiomorpholinyl, (dioxo)thiomorpholinyl, homopiperidinyl, or homopiperazinyl;
$R^7$ is hydrogen or alkyl;
$R^8$ is hydrogen or alkyl;
or $(R^7)(R^8)N$ taken together is azetidinyl, pyrrolidinyl, piperidinyl, piperazinyl, morpholinyl, or morpholinyl-N-oxide;
$R^9$ is hydrogen or alkyl;
$R^{10}$ is hydrogen, alkyl, hydroxyalkyl, alkoxyalkyl, or spiro[3.3]heptanol;
$R^{11}$ is hydrogen, alkyl, hydroxyalkyl, or alkoxyalkyl;
or $(R^{10})(R^{11})N$ taken together is azetidinyl, pyrrolidinyl, piperidinyl, piperazinyl, morpholinyl, thiomorpholinyl, (oxo)thiomorpholinyl, (dioxo)thiomorpholinyl, homopiperidinyl, or homopiperazinyl, and is substituted with 0-4 substituents selected from halo, alkyl, hydroxyalkyl, alkoxyalkyl, hydroxy, alkoxy, oxo, and acetamido;
$R^{12}$ is hydrogen, alkyl, or cycloalkyl;
$R^{13}$ is hydrogen or alkyl;
or $(R^{12})(R^{13})N$ taken together is azetidinyl, pyrrolidinyl, piperidinyl, piperazinyl, or morpholinyl, and is substituted with 0-3 substituents selected from halo and alkyl;
X is S, SO, or $SO_2$; and
Y is imidazolyl or triazolyl;
or a pharmaceutically acceptable salt thereof.

Another aspect of the invention is a compound of formula I where $Ar^1$ is phenyl or pyridinyl, and is substituted with 0-5 substituents selected from cyano, halo, alkyl, haloalkyl, alkoxy, and haloalkoxy; $Ar^2$ is phenyl or pyridinyl and is substituted with 0-5 substituents selected from cyano, halo, alkyl, $(R^3)$alkyl, haloalkyl, cycloalkyl, $(R^3)$cycloalkyl, alkoxy, cycloalkoxy, haloalkoxy, and alkoxycarbonyl; $R^1$ is alkoxy, or $(R^4)$alkoxy; and $R^2$ is $Ar^2$.

Another aspect of the invention is a compound of formula I where $Ar^1$ is phenyl substituted with 0-5 substituents selected from cyano, halo, alkyl, haloalkyl, alkoxy, and haloalkoxy; $Ar^2$ is phenyl substituted with 0-5 substituents selected from cyano, halo, alkyl, haloalkyl, alkoxy, and haloalkoxy; and $R^1$ is alkoxy, cyanoalkoxy, alkoxyalkyl, or $(R^4)$alkoxy; or a pharmaceutically acceptable salt thereof.

Another aspect of the invention is a compound of formula I where $Ar^1$ is phenyl substituted with 0-5 substituents selected from cyano, halo, alkyl, haloalkyl, alkoxy, and haloalkoxy.

Another aspect of the invention is a compound of formula I where $Ar^2$ is phenyl substituted with 3 halo substituents.

Another aspect of the invention is a compound of formula I where $R^1$ is alkoxy or $(R^4)$alkoxy.

Another aspect of the invention is a compound of formula I where Y is triazolyl.

Another aspect of the invention is a compound of formula I where Y is imidazolyl.

For a compound of Formula I, the scope of any instance of a variable substituent, including $R^1$, $R^2$, $R^3$, $R^4$, $R^5$, $R^6$, $R^7$, $R^8$, $R^9$, $R^{10}$, $R^{11}$, $R^{12}$, $R^{13}$, $Ar^1$, $Ar^2$, X, and Y can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. Terms with a hydrocarbon moiety (e.g. alkoxy) include straight and branched isomers for the hydrocarbon portion which are composed of 1 to 6 carbons. "Halo" includes fluoro, chloro, bromo, and iodo. "Haloalkyl" and "haloalkoxy" include all halogenated isomers from monohalo to perhalo "Aryl" means a monocyclic or bicyclic aromatic ring system having 5 to 12 carbon atoms wherein one or both of the rings are aromatic. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

ASSAY BUFFER Composition: 25 mM HEPES, 100 mM NaCl, 0.005% Tween 20, 0.05% BSA prepared in sterile water (all reagents from Sigma)

Controls:

Positive Control: 100% DMSO (1 µl)+His-tagged hGal-3 (20 µL)+B-ASF (20 µl)+Anti-His Terbium Antibody (5 µl)+Strep d2 Antibody (5 µl).

Negative Control: 100% DMSO (1 µl)+His-tagged hGal-3 (20µL)+Anti His Terbium Antibody (5 µl)+Strep d2 Aantibody (5 µl).

Stocks Preparation:

|  | Stock Conc. | Intermediate Conc. | Final Assay Conc. | Volume |
|---|---|---|---|---|
| His-tagged hGal-3 | 49.82 µM or can vary batch to batch | 2.525X | 15 nM | 20 µl |
| B-ASF | 25 µM | 2.525X | 15 nM | 20 µl |
| Compounds | 20 mM in 100% DMSO | Various concentration 100% DMSO | Various concentration 2% DMSO | 1 µl |
| Anti-His Tb Ab | 5.75 µM | (10X) 10 nM | 1 nM | 5 µl |
| Strep d2 | 16.67 µM | (10X) 200 nM | 20 nM | 5 µl |
| Total Assay volume |  |  |  | 51 µl |

PROTOCOL: The Gal-3 assays were performed in 384 white Opti plates in three replicates at room temperature with gentle shaking at 250-300 rpm From the original stocks, 2.525× working stock concentrations of His-tagged recombinant human Gal-3 (hGal-3) and that of B-ASF were prepared. From the working stock, 20 µl of hGal-3 (15 nM) and 20 µl B-ASF (15 nM) were added to the plates. In Negative Control, only hGal-3 was added. A concentration range of 50× working stocks were prepared for the compounds in 100% DMSO. Aliquots of 1 uL of the compounds were added to the wells and pre-incubated with 20 µl hGal-3 per well for 30 minutes Then 20 µl B-ASF were added and incubated for another 1 hour. To detect the signal, 5 µ(final conc. of 1.0 nM) terbium labelled Anti-His antibody was added and incubated for 30 min followed by adding 5 µ(final conc. of 20 nM) Streptavidin d2 and incubation for another 1 hour. The assay signal was detected using HTRF screen protocol (Excitation wavelength=340 nm, emission wavelength=615 nm/665 nm) on Envision 2104 Multilabel Reader. Data analysed using Toolset and Curve Master. Results are reported in the experimental section (IC$_{50}$ in µM).

Pharmaceutical Composition and Methods of Use

The compounds of this invention inhibit Gal-3. Accordingly, another aspect of the invention is a pharmaceutical composition comprising a therapeutically effective amount of a compound of Formula I, or a pharmaceutically acceptable salt thereof, and a pharmaceutically acceptable carrier.

Another aspect of the invention is a method for treating a patient afflicted with a disease or condition selected from fibrosis of organs (including liver, kidney, lung, heart and skin), liver diseases and conditions (including acute hepatitis, chronic hepatitis, liver fibrosis, liver cirrhosis, portal hypertension, regenerative failure, non-alcoholic steatohepatitis (NASH), liver hypofunction, and hepatic blood flow disorder), cell proliferative diseases, cancers, and conditions (including solid tumor, solid tumor metastasis, vascular fibroma, myeloma, multiple myeloma, Kaposi's sarcoma, leukemia, chronic lymphocytic leukemia (CLL)) and invasive metastasis of cancer cell), inflammatory diseases and conditions (including psoriasis, nephropathy, and pneumonia), gastrointestinal tract diseases and conditions (including irritable bowel syndrome (IBS), inflammatory bowel disease (IBD), and abnormal pancreatic secretion), renal diseases and conditions, urinary tract-associated diseases and conditions (including benign prostatic hyperplasia or symptoms associated with neuropathic bladder disease, spinal cord tumor, hernia of intervertebral disk, spinal canal stenosis, and symptoms derived from diabetes), lower urinary tract diseases and conditions (including obstruction of lower urinary tract), inflammatory diseases and conditions of lower urinary tract (including dysuria and frequent urination), pancreatic diseases and conditions, abnormal angiogenesis-associated diseases and conditions (including arterial obstruction), scleroderma, brain-associated diseases and conditions (including cerebral infarction and cerebral hemorrhage), neuropathic pain and peripheral neuropathy, ocular diseases and conditions (including age-related to macular degeneration (AMD), diabetic retinopathy, proliferative vitreoretinopathy (PVR), cicatricial pemphigoid, and glaucoma filtration surgery scarring) with a compound of formula I.

Another aspect of the invention is a method of treating renal fibrosis, pulmonary fibrosis, hepatic fibrosis, arterial fibrosis and systemic sclerosis comprising administering to a compound of formula I to a patient.

Another aspect of the invention is a method for treating fibrosis of organs (including liver, kidney, lung, heart and skin) comprising administering to a compound of formula I to a patient.

Another aspect of the invention is a method for treating liver diseases and conditions (including acute hepatitis, chronic hepatitis, liver fibrosis, liver cirrhosis, portal hypertension, regenerative failure, non-alcoholic steatohepatitis (NASH), liver hypofunction, and hepatic blood flow disorder) comprising administering to a compound of formula I to a patient.

Another aspect of the invention is a method for treating cell proliferative diseases, cancers, and conditions (including solid tumor, solid tumor metastasis, vascular fibroma, myeloma, multiple myeloma, Kaposi's sarcoma, leukemia, chronic lymphocytic leukemia (CLL)) and invasive metastasis of cancer cell) comprising administering to a compound of formula I to a patient.

Another aspect of the invention is a method for treating inflammatory diseases and conditions (including psoriasis, nephropathy, and pneumonia) comprising administering to a compound of formula I to a patient.

Another aspect of the invention is a method for treating gastrointestinal tract diseases and conditions (including irritable bowel syndrome (IBS), inflammatory bowel disease (IBD), and abnormal pancreatic secretion) comprising administering to a compound of formula I to a patient.

Another aspect of the invention is a method for treating renal diseases and conditions comprising administering to a compound of formula I to a patient.

Another aspect of the invention is a method for treating urinary tract-associated diseases and conditions (including benign prostatic hyperplasia or symptoms associated with neuropathic bladder disease, spinal cord tumor, hernia of intervertebral disk, spinal canal stenosis, and symptoms derived from diabetes) comprising administering to a compound of formula I to a patient.

Another aspect of the invention is a method for treating lower urinary tract diseases and conditions (including obstruction of lower urinary tract), inflammatory diseases and conditions of lower urinary tract (including dysuria and frequent urination) comprising administering to a compound of formula I to a patient.

Another aspect of the invention is a method for treating pancreatic diseases and conditions comprising administering to a compound of formula I to a patient.

Another aspect of the invention is a method for treating abnormal angiogenesis-associated diseases and conditions (including arterial obstruction) comprising administering to a compound of formula I to a patient.

Another aspect of the invention is a method for treating brain-associated diseases and conditions (including cerebral infarction and cerebral hemorrhage) comprising administering to a compound of formula I to a patient.

Another aspect of the invention is a method for treating neuropathic pain and peripheral neuropathy comprising administering to a compound of formula I to a patient.

Another aspect of the invention is a method for treating ocular diseases and conditions (including age-related macular degeneration (AMD), diabetic retinopathy, proliferative vitreoretinopathy (PVR), cicatricial pemphigoid, and glaucoma filtration surgery scarring) comprising administering to a compound of formula I to a patient.

The compounds of the invention may be used in the treatment and/or prophylaxis of conditions in which Gal-3 plays a role.

The compounds of the present invention may be used for the manufacture of a medicament for the treatment and/or prophylaxis of a condition in which inhibition of the physiological activity of Gal-3 is useful, such as diseases in which a Gal-3 receptor participates, is involved in the etiology or pathology of the disease, or is otherwise associated with at least one symptom of the disease.

The compounds of the invention can be used alone, in combination with other compounds of the present invention, or in combination with one or more, preferably one to two other agent(s).

"Therapeutically effective" means the amount of agent required to provide a meaningful patient benefit as understood by practitioners in the field of pain.

"Patient" means a person afflicted with pain and suitable for therapy as understood by practitioners in the field.

"Treatment," "therapy," "regimen," and related terms are used as understood by practitioners in the field.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

Chemical Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the claims, rather than to the foregoing examples, and all changes which come within the meaning and range of equivalency of the claims are therefore intended to be embraced.

Analytical LC-MS/HPLC retention time reported for each example and intermediate uses one of the following general analytical LC-MS/HPLC conditions:

Lcms Conditions:

Method A: Column: XBridge BEH XP C18 (50×2.1)mm, 2.5 μm; Mobile phase A: 10 mM $NH_4OAc$, Acetonitrile (95:5); Mobile phase B: 10 mM $NH_4OAc$: Acetonitrile (5:95); Gradient=0-100% B over 3 minutes; Temperature: 50° C.; Flow rate: 1.1 mL/min; Detection: UV at 220 nm.

Method B: Column: XBridge BEH XP C18 (50×2.1)mm, 2.5 μm; Mobile phase A: 0.1% TFA in water, Acetonitrile (95:5); Mobile phase B: 0.1% TFA in water, Acetonitrile (5:95); Gradient=0-100% B over 3 minutes; Temperature: 50° C.; Flow rate: 1.1 mL/min; Detection: UV at 220 nm.

Method C: Column-KINETEX-XB-C18 (75×3 mm-2.6 μm); M.phase A: 10 mM NH4COOH IN WATER:ACN(98:02); M.phase B: 10 mM NH4COOH IN WATER:ACN(02:98); Gradient=20-100% B over 5 minutes; Flow rate: 1.1 mL/min; Detection: UV at 254 nm.

Method D: Column: Waters Acquity UPLC BEH C18 (2.1× 50 mm), 1.7μ; Mobile phase A: 0.1% TFA in water; Mobile phase B: 0.1% TFA in Acetonitrile; Gradient=20-90% B over 1.1 minute, then a 0.6 minute hold at 90% B; Temperature: 50° C.; Flow rate: 0.7 mL/min; Detection: UV at 220 nm.

Method E: Column: Waters Acquity UPLC BEH C18 (2.1× 50 mm) 1.7μ, Mobile phase A: 10 mM $NH_4OAc$, Acetonitrile (95:5); Mobile phase B: 10 mM $NH_4OAc$: Acetonitrile (5:95), Gradient=20-90% B over 1.1 minute, then a 0.6 minute hold at 90% B; Temperature: 50° C.; Flow rate: 0.7 mL/min; Detection: UV at 220 nm Prep-HPLC Conditions:

Method A: Column: Waters XBridge C18, 19×150 mm, 5-μm particles; Mobile Phase A: 10-mM ammonium acetate; Mobile Phase B: acetonitrile; Gradient: 15-50% B over 20 minutes, then a 5-minute hold at 100% B; Flow: 15 mL/min.

Method B: Column: Inertsil ODS(250*19)mm-5 μm particles; Mobile Phase A: 010-mM ammonium acetate-pH-4.5; Mobile Phase B: ACN; Gradient: 0-80% B over 20 minutes, then a 5-minute hold at 100% B; Flow: 17 mL/min.

Method C: Column: XBridge phenyl C18 (19×250 mm), 5-μm particles; Mobile Phase A: 10-mM ammonium acetate; Mobile Phase B: acetonitrile; Gradient: 0-50% B over 20 minutes, then a 5-minute hold at 100% B; Flow: 17 mL/min.

Method D: Column: Inertsil ODS(250*19)mm-5 μm particles; Mobile Phase A: 10-mM ammonium acetate; Mobile Phase B: ACN; Gradient: 0-90% B over 25 minutes, then a 5-minute hold at 100% B; Flow: 17 mL/min.

Method E: Column: Sunfire OBD(250*30)mm-5 μm particles; Mobile Phase A: 10-mM ammonium acetate; Mobile Phase B: ACN; Gradient: 0-95% B over 25 minutes, then a 5-minute hold at 100% B; Flow: 30 mL/min.

Method F: Column: Symmetry C8(300*19)mm-7 μm particles; Mobile Phase A: 10-mM ammonium acetate; Mobile Phase B: ACN; Gradient: 0-90% B over 20 minutes, then a 5-minute hold at 100% B; Flow: 18 mL/min.

Method G: Column: Sunfire C18 1(150×19)mm-5 μm particles; Mobile Phase A: 10-mM ammonium acetate; Mobile Phase B: ACN; Gradient: 0-70% B over 25 minutes, then a 5-minute hold at 100% B; Flow: 15 mL/min.

Method H: Column: Waters XBridge C18, 150 mm×19 mm, 5-μm particles; Mobile Phase A: 5:95 acetonitrile: water with 0.1% TFA; Mobile Phase B: 95:5 acetonitrile: water with 0.1% TFA; Gradient: 0-minute hold at 10% B, 10-45% B over 25 minutes, then a 5-minute hold at 100% B; Flow Rate: 15 mL/min.

Method I: Column: Inertsil ODS(250*20)mm-5 μm particles; Mobile Phase A: 10-mM ammonium acetate; Mobile Phase B: TFE; Gradient: 0-80% B over 20 minutes, then a 5-minute hold at 100% B; Flow: 18 mL/min.

Method J: Column: Lux-cellulose C2(250×21.2)mm, 5 micron; Mobile Phase: ACN:MeOH(1:1); Gradient: 0-100% B over 20 minutes, then a 5-minute hold at 100% B; Flow: 19 mL/min.

Synthetic Scheme for C2-Methoxy Analogs

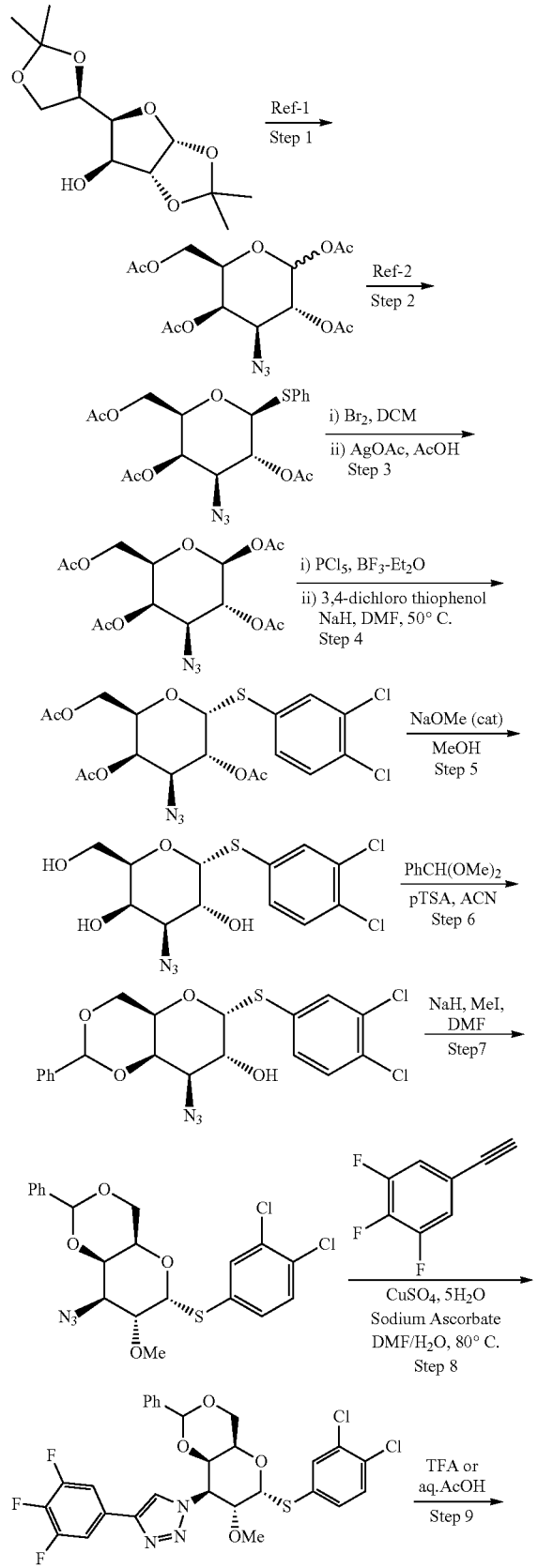

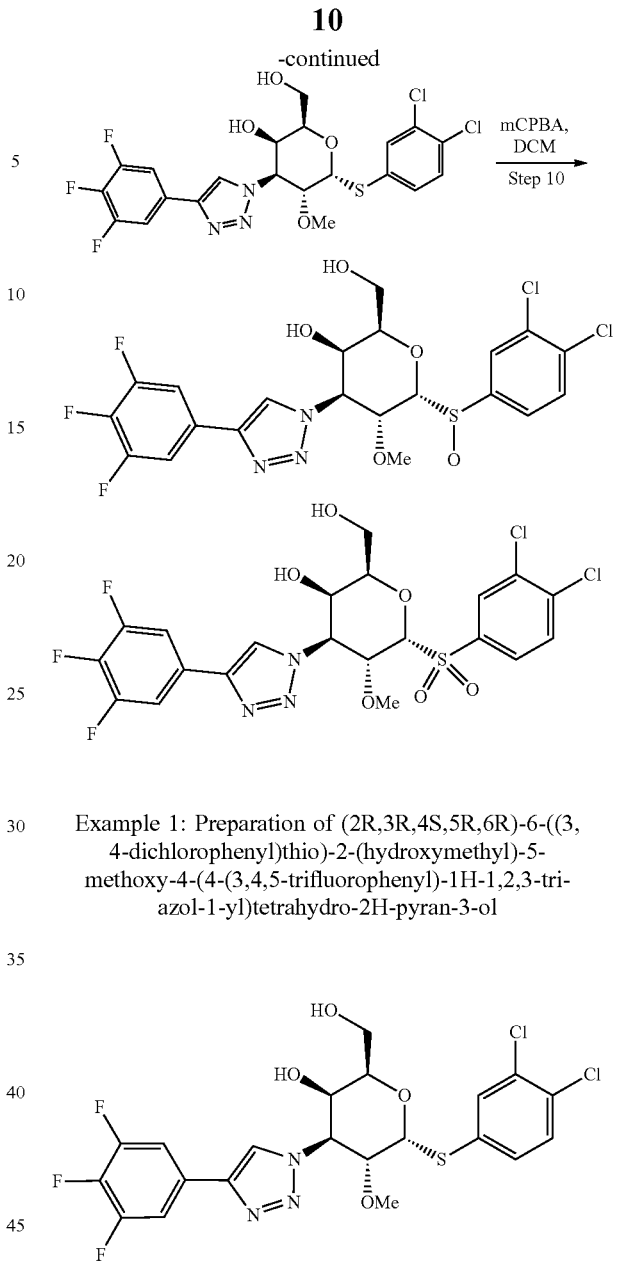

Example 1: Preparation of (2R,3R,4S,5R,6R)-6-((3,4-dichlorophenyl)thio)-2-(hydroxymethyl)-5-methoxy-4-(4-(3,4,5-trifluorophenyl)-1H-1,2,3-triazol-1-yl)tetrahydro-2H-pyran-3-ol Step 1: ((3R,4S,5R,6R)-6-(acetoxymethyl)-4-azidotetrahydro-2H-pyran-2,3,5-triyl triacetate from (3aR,5S,6S,6aR)-5-((R)-2,2-dimethyl-1,3-dioxolan-4-yl)-2,2-dimethyltetrahydrofuro[2,3-d][1,3]dioxol-6-ol as described in the literature. (Carbohydrate Res., 1994, 251, 33-67}.

Step 2: (2R,3R,4S,5R,6S)-2-(acetoxymethyl)-4-azido-6-(phenylthio)tetrahydro-2H-pyran-3,5-diyl diacetate from ((3R,4S,5R,6R)-6-(acetoxymethyl)-4-azidotetrahydro-2H-pyran-2,3,5-triyl triacetate as described in the literature. (ChemMedChem., 2009, 4, 1810-1815 and references cited therein).

Step 3: Synthesis of (2S,3R,4S,5R,6S)-6-(acetoxymethyl)-4-azidotetrahydro-2H-pyran-2,3,5-triyl triacetate: To a stirred solution of ((2R,3R,4S,5R,6S)-2-(acetoxymethyl)-4-azido-6-(phenylthio)tetrahydro-2Hpyran-3,5-diyl diacetate (500 mg, 1.181 mmol) in DCM (15 mL) at −15° C., Br₂ (0.091 mL, 1.77 mmol) in DCM (5 mL) was added drop wise. Then reaction mixture was slowly warmed to 0° C. and stirred for 15 min. Reaction mixture was quenched with cyclopentene (0.8 mL) and solvent was removed under reduced pressure to get the crude bromo derivative which was taken as such for next step without further purification. The bromo compound was dissolved in AcOH (15 mL), silver acetate (197 mg, 1.181 mmol) was added and suspension was stirred at rt for 1 h. Reaction mixture was diluted with DCM (3×100 mL), washed with water, aq.sodium bicarbonate, water, brine and dried over sodium sulphate. Solvent was removed under reduced pressure to get the crude residue which was purified via chromatography in silica gel (30-60% EtOAc in Hexane) to yield (2S,3R,4S, 5R,6R)-6-(acetoxymethyl)-4-azidotetrahydro-2H-pyran-2, 3,5-triyl triacetate (0.26 g, 0.68 mmol, 58%) as an off-white solid. 1H NMR (400 MHz, CHLOROFORM-d): δ 5.68 (d, J=8.5 Hz, 1H), 5.46 (dd, J=3.5, 1.0 Hz, 1H), 5.31-5.24 (m, 1H), 4.19-4.12 (m, 1H), 4.10-3.98 (m, 2H), 3.67 (dd, J=10.5, 3.5 Hz, 1H), 2.19 (s, 3H), 2.13 (s, 6H), 2.06 (s, 3H).

Step 4: (2R,3R,4S,5R,6R)-2-(acetoxymethyl)-4-azido-6-((3,4-dichlorophenyl)thio)tetrahydro-2H-pyran-3,5-diyl diacetate from (2S,3R,4S,5R,6R)-6-(acetoxymethyl)-4-azidotetrahydro-2H-pyran-2,3,5-triyltriacetate as described in WO2016120403.

Step 5: Synthesis of (2R,3R,4S,5R,6R)-4-azido-2-((3,4-dichlorophenyl)thio)-6-(hydroxymethyl)tetrahydro-2H-pyran-3,5-diol: To a stirred solution of (2R,3R,4S,5R,6R)-2-(acetoxymethyl)-4-azido-6-((3,4-dichlorophenyl)thio) tetrahydro-2Hpyran-3,5-diyl diacetate (2 g, 4.06 mmol) in MeOH (50 mL), 25% sodium methoxide in MeOH (0.088 g, 0.406 mmol) was added at rt and stirred at rt for 1 h. The reaction mixture was neutralized with Amberlite IR120 ($H^+$-resin), and concentrated to give (2R,3R,4S,5R,6R)-4-azido-2-((3,4-dichlorophenyl)thio)-6-(hydroxymethyl)tetrahydro-2H-pyran-3,5-diol (1.4 g, 3.75 mmol, 92%) as an off-white solid which was as such taken for next step without further purification. LC-MS, [M+23]+=388.4, {Method E: tR=0.96}. 1H NMR (400 MHz, METHANOL-d4): δ 7.75 (d, J=2.0 Hz, 1H), 7.52-7.42 (m, 2H), 5.69 (d, J=5.5 Hz, 1H), 4.40 (dd, J=11.0, 5.5 Hz, 1H), 4.30-4.24 (m, 1H), 4.08-4.04 (m, 1H), 3.75-3.62 (m, 2H), 3.54-3.47 (m, 1H).

Step 6: Synthesis of (4aR,6R,7R,8R,8aR)-8-azido-6-((3, 4-dichlorophenyl)thio)-2-phenylhexahydropyrano[3,2-d][1, 3]dioxin-7-ol: To a stirred solution (2R,3R,4S,5R,6R)-4-azido-2-((3,4-dichlorophenyl)thio)-6-(hydroxymethyl) tetrahydro-2Hpyran-3,5-diol (1.4 g, 3.82 mmol) and benzaldehyde dimethyl acetal (1.148 mL, 7.65 mmol) in ACN (50 mL), p-TSA (0.073 g, 0.382 mmol) was added at rt under nitrogen and stirred at rt for overnight. Then the solvent was removed under reduced pressure and purified via chromatography in silica gel (0-40% EtOAc in Hexane) to give (4aR,6R,7R,8R,8aR)-8-azido-6-((3,4-dichlorophenyl)thio)-2-phenylhexahydropyrano[3,2-d][1,3]dioxin-7-ol (1.7 g, 3.74 mmol, 98%) as an off-white solid. LC-MS, [M+1]+=454.0, {Method C: tR: 3.11 min}. 1H NMR (400 MHz, CHLOROFORM-d): δ 7.73 (d, J=2.5 Hz, 1H), 7.52-7.50 (m, 2H), 7.40-7.25 (m, 5H), 5.83 (d, J=5.2 Hz, 1H), 5.63 (s, 1H), 4.64-4.60 (m, 1H), 4.39 (d, J=3.2 Hz, 1H), 4.31 (d, J=10.7 Hz, 1H), 4.18-4.14 (m, 2H), 3.52 (dd, J=10.7, 3.2 Hz, 1H), 2.26 (d, J=7.6 Hz, 1H, —OH).

Step 7: Synthesis of (4aR,6R,7R,8S,8aR)-8-azido-6-((3, 4-dichlorophenyl)thio)-7-methoxy-2-phenylhexahydropyrano[3,2-d][1,3]dioxine: To a stirred solution of (4aR,6R, 7R,8R,8aR)-8-azido-6-((3,4-dichlorophenyl)thio)-2-phenylhexahydropyrano[3,2-d][1,3]dioxin-7-ol (180 mg, 0.396 mmol) in DMF (5 mL), NaH (31.7 mg, 0.792 mmol) was added at 0° C. under nitrogen and stirred for 5 min. methyl iodide (0.050 mL, 0.792 mmol) was added and allowed to reach rt and stirred for 1 h. Then the reaction mixture was diluted with EtOAc (2×50 mL), washed with water, brine solution, dried over sodium sulphate and concentrated to give (4aR,6R,7R,8S,8aR)-8-azido-6-((3,4-dichlorophenyl)thio)-7-methoxy-2-phenylhexahydropyrano [3,2-d][1,3]dioxine (180 mg, 0.36 mmol, 90%) as an off-white solid which was a such taken for next step without further purification. 1H NMR (400 MHz, CHLOROFORM-d): δ 7.59 (d, J=2.0 Hz, 1H), 7.55-7.49 (m, 2H), 7.41-7.33 (m, 4H), 7.33-7.28 (m, 1H), 6.02 (d, J=5.5 Hz, 1H), 4.32 (d, J=3.0 Hz, 1H), 4.27-4.20 (m, 2H), 4.12 (dd, J=14.8, 2.3 Hz, 2H), 3.69 (dd, J=10.5, 3.5 Hz, 1H), 3.55 (s, 3H).

Step 8: Synthesis of (1-((4aR,6R,7R,8S,8aR)-6-((3,4-dichlorophenyl)thio)-7-methoxy-2-phenylhexahydropyrano [3,2-d][1,3]dioxin-8-yl)-4-(3,4,5-trifluorophenyl)-1H-1,2,3-triazole: To a stirred solution of (4aR,6R,7R,8S,8aR)-8-azido-6-((3,4-dichlorophenyl)thio)-7-methoxy-2-phenylhexahydropyrano[3,2-d][1,3]dioxine (80 mg, 0.171 mmol) in DMF (3 mL) and Water (1 mL), sodium ascorbate (33.8 mg, 0.171 mmol), copper (II) sulfate pentahydrate (38.4 mg, 0.154 mmol) and 5-ethynyl-1,2,3-trifluorobenzene (0.042 mL, 0.342 mmol) were added at rt. Then the reaction mixture was heated at 85° C. for 1 h. Reaction mixture was cooled to rt, diluted with ice cold water (10 mL) and stirred for 15 min to get a solid. The solid was filtered, obtained solid was suspended in DCM (10 mL), filtered through celite pad and washed with excess DCM. Filtrate was dried over sodium sulphate and concentrated to afford (1-((4aR,6R,7R,8S,8aR)-6-((3,4-dichlorophenyl)thio)-7-methoxy-2-phenylhexahydropyrano[3,2-d][1,3]dioxin-8-yl)-4-(3,4,5-trifluorophenyl)-1H-1,2,3-triazole (100 mg, 0.16 mmol, 94%) as an off-white solid. LC-MS, [M+H]+= 624.0, {Method C: tR: 4.148 min}. 1H NMR (400 MHz, DMSO-d6): δ 8.94 (s, 1H), 7.87 (d, J=2.2 Hz, 1H), 7.77 (dd, J=9.0, 6.6 Hz, 2H), 7.66 (d, J=8.6 Hz, 1H), 7.56 (dd, J=8.4, 2.1 Hz, 1H), 7.39-7.31 (m, 5H), 6.64 (d, J=5.1 Hz, 1H), 5.58 (s, 1H), 5.15 (dd, J=11.5, 3.4 Hz, 1H), 4.66 (dd, J=11.5, 5.1 Hz, 1H), 4.58 (d, J=3.2 Hz, 1H), 4.31 (br. s., 1H), 4.14 (d, J=11.6 Hz, 1H), 3.98 (d, J=11.6 Hz, 1H), 3.36 (s, 3H, obscured with solvent moisture peak).

Step 9: Synthesis of (2R,3R,4S,5R,6R)-6-((3,4-dichlorophenyl)thio)-2-(hydroxymethyl)-5-methoxy-4-(4-(3,4,5-trifluorophenyl)-1H-1,2,3-triazol-1-yl)tetrahydro-2H-pyran-3-ol: To a stirred solution of 1-((4aR,6R,7R,8S,8aR)-6-((3,4-dichlorophenyl)thio)-7-methoxy-2-phenylhexahydropyrano [3,2-d][1,3]dioxin-8-yl)-4-(3,4,5-trifluorophenyl)-1H-1,2,3-triazole (75 mg, 0.120 mmol) in DCM (3 mL), TFA (0.5 mL, 6.49 mmol) was added at rt under nitrogen and stirred at rt for 4 h. Solvent was removed under reduced pressure and crude was purified by prep-HPLC Method D to afford Example 1 ((2R,3R,4S,5R,6R)-6-((3,4-dichlorophenyl) thio)-2-(hydroxymethyl)-5-methoxy-4-(4-(3,4,5-trifluorophenyl)-1H-1,2,3-triazol-1-yl)tetrahydro-2H-pyran-3-ol (14.5 mg, 0.026 mmol, 22%) as an off-white solid. LC-MS, [M+H]+=536.0, {Method C: tR=3.05 min}. 1H NMR (400 MHz, METHANOL-d4): δ 8.49 (s, 1H), 7.73 (d, J=2.0 Hz, 1H), 7.57 (dd, J=9.0, 6.6 Hz, 2H), 7.45 (d, J=2.0 Hz, 1H), 7.41-7.37 (m, 1H), 6.08 (d, J=5.1 Hz, 1H), 4.91 (dd, J=11.2, 2.9 Hz, 1H), 4.52 (dd, J=11.2, 5.4 Hz, 1H), 4.39-4.34 (m, 1H), 4.09 (d, J=2.2 Hz, 1H), 3.66-3.55 (m, 2H), 3.30 (s, 3H). hGal3 $IC_{50}$=0.7 uM.

Example 2 & Example 3: (2R,3R,4S,5R,6R)-6-((R)-(3,4-dichlorophenyl)sulfinyl)-2-(hydroxymethyl)-5-methoxy-4-(4-(3,4,5-trifluorophenyl)-1H-1,2,3-triazol-1-yl)tetrahydro-2H-pyran-3-ol and (2R,3R,4S,5R,6R)-6-((3,4-dichlorophenyl)sulfonyl)-2-(hydroxymethyl)-5-methoxy-4-(4-(3,4,5-trifluorophenyl)-1H-1,2,3-triazol-1-yl)tetrahydro-2H-pyran-3-ol

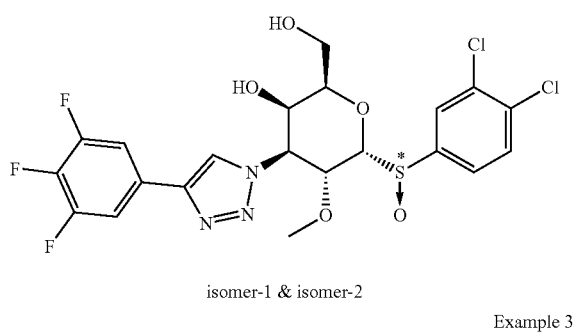

isomer-1 & isomer-2

Step 1: Synthesis of (2R,3R,4S,5R,6R)-6-((R)-(3,4-dichlorophenyl)sulfinyl)-2-(hydroxymethyl)-5-methoxy-4-(4-(3,4,5-trifluorophenyl)-1H-1,2,3-triazol-1-yl)tetrahydro-2H-pyran-3-ol and (2R,3R,4S,5R,6R)-6-((3,4-dichlorophenyl)sulfonyl)-2-(hydroxymethyl)-5-methoxy-4-(4-(3,4,5-trifluorophenyl)-1H-1,2,3-triazol-1-yl)tetrahydro-2H-pyran-3-ol: To a stirred solution of Example 1, (2R,3R,4S,5R,6R)-6-((3,4-dichlorophenyl)thio)-2-(hydroxymethyl)-5-methoxy-4-(4-(3,4,5-trifluorophenyl)-1H-1,2,3-triazol-1-yl)tetrahydro-2H-pyran-3-ol (85 mg, 0.158 mmol) in DCM (10 mL), mCPBA (39.1 mg, 0.158 mmol) was added at 0° C. Then reaction mixture was allowed to reach rt and stirred for 1 h. Then the reaction mixture was diluted with DCM (2×50 mL), washed with aq.NaHCO₃, water, brine solution, dried over sodium sulphate and concentrated. Crude residue was purified by prep-HPLC Method E to afford Example 2 (isomer-1) (2R,3R,4S,5R,6R)-6-((R)-(3,4-dichlorophenyl)sulfinyl)-2-(hydroxymethyl)-5-methoxy-4-(4-(3,4,5-trifluorophenyl)-1H-1,2,3-triazol-1-yl)tetrahydro-2H-pyran-3-ol (30 mg, 0.054 mmol, 34%) as an off-white solid, Example 2 (isomer-2) (2R,3R,4S,5R,6R)-6-((R)-(3,4-dichlorophenyl)sulfinyl)-2-(hydroxymethyl)-5-methoxy-4-(4-(3,4,5-trifluorophenyl)-1H-1,2,3-triazol-1-yl)tetrahydro-2H-pyran-3-ol (9 mg, 0.016 mmol, 10%) as an off-white solid and Example 3 (2R,3R,4S,5R,6R)-6-((3,4-dichlorophenyl)sulfonyl)-2-(hydroxymethyl)-5-methoxy-4-(4-(3,4,5-trifluorophenyl)-1H-1,2,3-triazol-1-yl)tetrahydro-2H-pyran-3-ol (22 mg, 0.038 mmol, 24%) as an off white solid.

Example 2 (Isomer-1)

LC-MS, [M+H]+=552.0, {Method C: tR=2.55 min}. 1H NMR (400 MHz, METHANOL-d4): δ 8.62 (s, 1H), 8.07-8.04 (m, 1H), 7.82-7.77 (m, 2H), 7.73-7.64 (m, 2H), 5.65-5.60 (m, 1H), 5.25 (d, J=5.0 Hz, 1H), 4.88 (d, J=5.5 Hz, 1H), 4.24 (d, J=2.0 Hz, 1H), 4.14 (t, J=5.8 Hz, 1H), 3.59-3.44 (m, 2H), 3.21 (s, 3H). hGal3 IC₅₀=0.029 uM.

Example 2 (Isomer-2)

LC-MS, [M+H]+=552.0, {Method C: tR=2.697 min}. 1H NMR (400 MHz, METHANOL-d4): δ 8.68 (s, 1H), 8.03 (d, J=2.0 Hz, 1H), 7.81 (d, J=8.5 Hz, 1H), 7.74 (d, J=2.0 Hz, 1H), 7.73-7.71 (m, 1H), 7.70-7.66 (m, 1H), 5.81 (dd, J=11.5, 2.5 Hz, 1H), 5.20 (d, J=6.5 Hz, 1H), 4.98-4.92 (m, 2H), 4.25 (d, J=2.0 Hz, 1H), 3.58-3.46 (m, 5H). hGal3 IC₅₀=0.155 uM.

Example 3

LC-MS, [M+H]+=568.0, {Method C: tR=2.72 min}. 1H NMR (400 MHz, METHANOL-d4): δ 8.64 (s, 1H), 8.19 (d, J=2.0 Hz, 1H), 7.95 (dd, J=8.4, 2.1 Hz, 1H), 7.84 (d, J=8.6 Hz, 1H), 7.68 (dd, J=8.8, 6.6 Hz, 2H), 5.78-5.71 (m, 2H), 4.91-4.87 (m, 1H), 4.58-4.51 (m, 1H), 4.27 (d, J=2.4 Hz, 1H), 3.64-3.51 (m, 2H), 3.35 (s, 3H). hGal3 IC₅₀=0.112 uM.

General Synthetic Scheme for C2-Modified Analogs

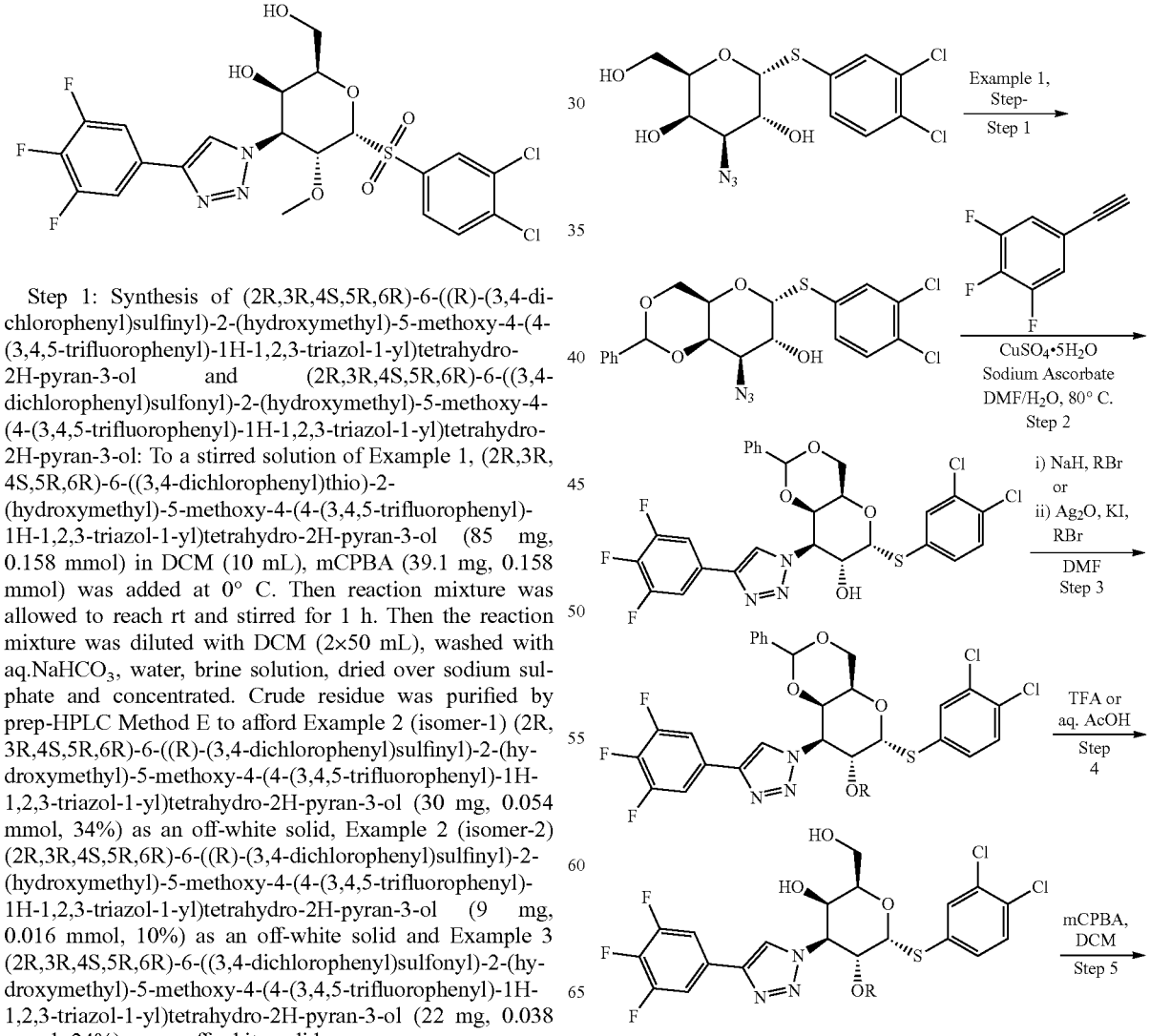

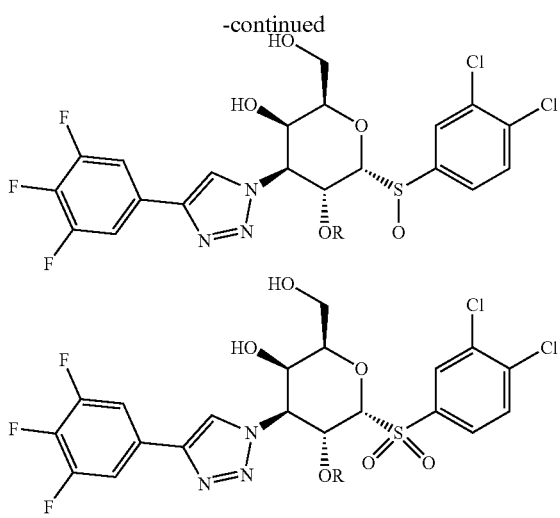

Example 4: Preparation of (2R,3R,4S,5R,6R)-6-((3,4-dichlorophenyl)thio)-5-ethoxy-2-(hydroxymethyl)-4-(4-(3,4,5-trifluorophenyl)-1H-1,2,3-triazol-1-yl)tetrahydro-2H-pyran-3-ol Step 1: ((4aR,6R,7R,8R,8aR)-8-azido-6-((3,4-dichlorophenyl)thio)-2-phenylhexahydropyrano[3,2-d][1,3]dioxin-7-ol from (2R,3R,4S,5R,6R)-4-azido-2-((3,4-dichlorophenyl)thio)-6-(hydroxymethyl)tetrahydro-2H-pyran-3,5-diol as described in Example 1.

Step 2: Synthesis of (4aR,6R,7R,8R,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-ol: Prepared in a similar fashion as described in Example 1, step 8 using ((4aR,6R,7R,8R,8aR)-8-azido-6-((3,4-dichlorophenyl)thio)-2-phenylhexahydropyrano[3,2-d][1,3]dioxin-7-ol (600 mg, 1.321 mmol) and 5-ethynyl-1,2,3-trifluorobenzene (0.403 mL, 3.30 mmol) to afford ((4aR,6R,7R,8R,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-ol (0.75 g, 1.23 mmol, 93%) as an off-white solid. LC-MS, [M+45]+=654.8, {Method C: tR: 3.63 min}. 1H NMR (400 MHz, DMSO-d6)): δ 8.84 (s, 1H), 7.84-7.75 (m, 3H), 7.67-7.61 (m, 1H), 7.53 (dd, J=8.5, 2.0 Hz, 1H), 7.41-7.26 (m, 5H), 6.17 (d, J=5.0 Hz, 1H), 6.11 (d, J=4.5 Hz, 1H), 5.56 (s, 1H), 5.10 (dd, J=11.3, 3.3 Hz, 1H), 4.92 (dd, J=10.8, 5.3 Hz, 1H), 4.57 (d, J=3.5 Hz, 1H), 4.30 (s, 1H), 4.18-4.08 (m, 1H), 4.01-3.90 (m, 1H).

Step 3: Synthesis of 1-((4aR,6R,7R,8S,8aR)-6-((3,4-dichlorophenyl)thio)-7-ethoxy-2-phenylhexahydropyrano[3,2-d][1,3]dioxin-8-yl)-4-(3,4,5-trifluorophenyl)-1H-1,2,3-triazole: Prepared in a similar fashion as described in Example 1, step 7 using (4aR,6R,7R,8R,8aR)-6-((3,4-dichlorophenyl)thio)-2-phenyl-8-(4-(3,4,5-trifluorophenyl)-1H-1,2,3-triazol-1-yl) hexahydropyrano[3,2-d][1,3]dioxin-7-ol (100 mg, 0.164 mmol) and iodoethane (0.040 mL, 0.491 mmol) to afford 1-((4aR,6R,7R,8S,8aR)-6-((3,4-dichlorophenyl)thio)-7-ethoxy-2-phenylhexahydropyrano[3,2-d][1,3]dioxin-8-yl)-4-(3,4,5-trifluorophenyl)-1H-1,2,3-triazole (90 mg, 0.139 mmol, 85%) as an off-white solid. LC-MS, [M+H]+=638.0, {Method C: tR: 4.018 min}.

Step 4: Synthesis of (2R,3R,4S,5R,6R)-6-((3,4-dichlorophenyl)thio)-5-ethoxy-2-(hydroxymethyl)-4-(4-(3,4,5-trifluorophenyl)-1H-1,2,3-triazol-1-yl)tetrahydro-2H-pyran-3-ol: A suspension of 1-((4aR,6R,7R,8S,8aR)-6-((3,4-dichlorophenyl)thio)-7-ethoxy-2-phenylhexahydropyrano[3,2-d][1,3]dioxin-8-yl)-4-(3,4,5-trifluorophenyl)-1H-1,2,3-triazole (90 mg, 0.141 mmol) in 70% aq.AcOH (50 mL, 873 mmol) was heated at 75° C. for 18 h. Solvent was removed under reduced pressure and purified by prep-HPLC Method F to afford Example 4 (2R,3R,4S,5R,6R)-6-((3,4-dichlorophenyl)thio)-5-ethoxy-2-(hydroxymethyl)-4-(4-(3,4,5-trifluorophenyl)-1H-1,2,3-triazol-1-yl)tetrahydro-2H-pyran-3-ol (41 mg, 0.073 mmol, 52%) as an off-white solid. LC-MS, [M+H]+=550.7, {Method C: tR=3.393 min}. 1H NMR (400 MHz, METHANOL-d4): δ 8.61-8.56 (m, 1H), 7.82 (d, J=2.0 Hz, 1H), 7.68 (dd, J=8.8, 6.8 Hz, 2H), 7.58-7.48 (m, 2H), 6.17 (d, J=5.5 Hz, 1H), 5.03 (dd, J=11.3, 2.8 Hz, 1H), 4.73 (dd, J=11.5, 5.5 Hz, 1H), 4.47 (t, J=6.3 Hz, 1H), 4.21 (d, J=2.5 Hz, 1H), 3.85-3.65 (m, 3H), 3.52-3.41 (m, 1H), 1.04 (t, J=7.0 Hz, 3H). hGal3 IC$_{50}$=1.05 uM The Examples in the table below were prepared in an analogous fashion to Example 4 [Step-2 and Step-3], substituting appropriate alkyl halides in the synthetic sequence.

| Ex. | hGal3 IC$_{50}$ (uM) | Structure | LCMS RT | M + H | Method |
|---|---|---|---|---|---|
| 2 | 0.046 | 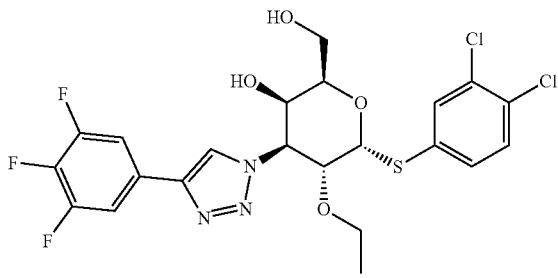 [SMILES: CCO[C@@H]1[C@@H](n2cc(-c3cc(F)c(F)c(F)c3)nn2)[C@@H](O)[C@@H](CO)O[C@@H]1Sc1ccc(Cl)c(Cl)c1] | 1.68 | 580.0 | B |

-continued

| Ex. | hGal3 IC$_{50}$ (uM) | Structure | LCMS RT | M + H | Method |
|---|---|---|---|---|---|
| 3 | 0.200 | 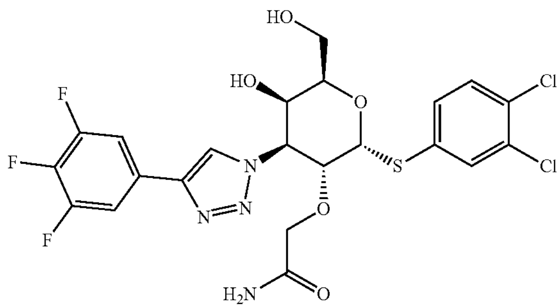 [SMILES: NC(=O)CO[C@@H]1[C@@H](n2cc(-c3cc(F)c(F)c(F)c3)nn2)[C@@H](O)[C@@H](CO)O[C@@H]1Sc1ccc(Cl)c(Cl)c1] | 1.54 | 579.1 | B |
| 4 | 0.224 | 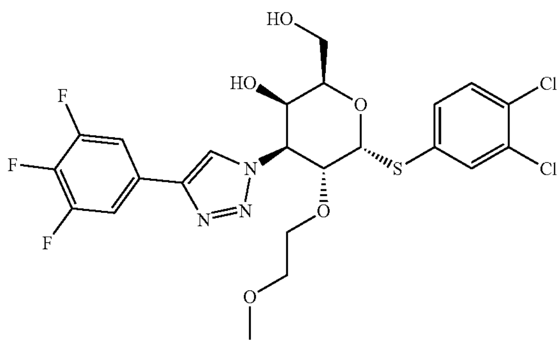 [SMILES: COCCO[C@@H]1[C@@H](n2cc(-c3cc(F)c(F)c(F)c3)nn2)[C@@H](O)[C@@H](CO)O[C@@H]1Sc1ccc(Cl)c(Cl)c1] | 3.045 | 580.0 | C |
| 5 | 0.195 | 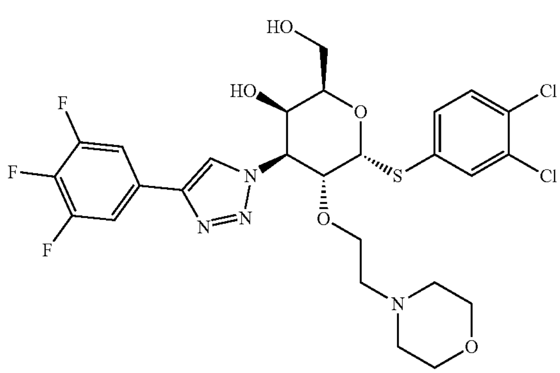 [SMILES: OC[C@H]1O[C@H](Sc2ccc(Cl)c(Cl)c2)[C@H](OCCN2CCOCC2)[C@@H](n2cc(-c3cc(F)c(F)c(F)c3)nn2)[C@H]1O] | 2.91 | 635.6 | C |

Example 9 & Example 10: (2R,3R,4S,5R,6R)-6-((S)-(3,4-dichlorophenyl)sulfinyl)-5-ethoxy-2-(hydroxymethyl)-4-(4-(3,4,5-trifluorophenyl)-1H-1,2,3-triazol-1-yl)tetrahydro-2H-pyran-3-ol and (2R,3R,4S,5R,6R)-6-((3,4-dichlorophenyl)sulfonyl)-5-ethoxy-2-(hydroxymethyl)-4-(4-(3,4,5-trifluorophenyl)-1H-1,2,3-triazol-1-yl)tetrahydro-2H-pyran-3-ol

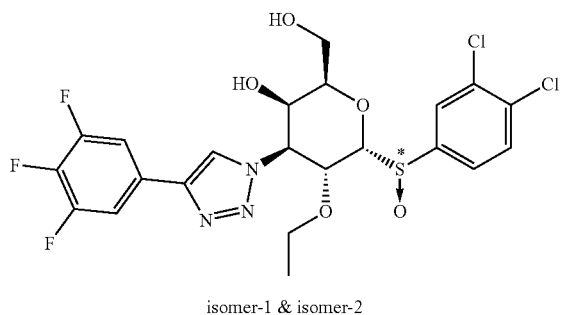

isomer-1 & isomer-2

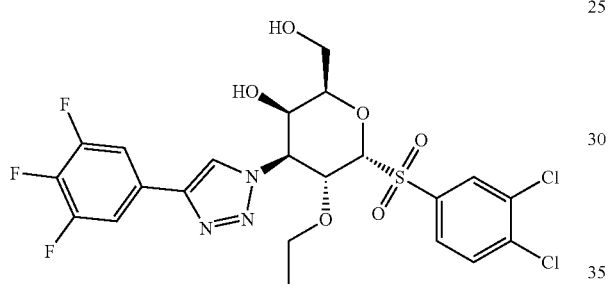

Example 10

Prepared in a similar fashion as described in Example-2 & Example-3, step 1 using Example 4 (2R,3R,4S,5R,6R)-6-((3,4-dichlorophenyl)thio)-5-ethoxy-2-(hydroxymethyl)-4-(4-(3,4,5-trifluorophenyl)-1H-1,2,3-triazol-1-yl)tetrahydro-2H-pyran-3-ol (38 mg, 0.069 mmol) and purified by prep-HPLC Method A to afford Example 9 (isomer-1) (2R,3R,4S,5R,6R)-6-((S)-(3,4-dichlorophenyl)sulfinyl)-5-ethoxy-2-(hydroxymethyl)-4-(4-(3,4,5-trifluorophenyl)-1H-1,2,3-triazol-1-yl)tetrahydro-2H-pyran-3-ol (9.4 mg, 0.016 mmol, 24%) as an off-white solid, Example 9 (isomer-2) (2R,3R,4S,5R,6R)-6-((S)-(3,4-dichlorophenyl)sulfinyl)-5-ethoxy-2-(hydroxymethyl)-4-(4-(3,4,5-trifluorophenyl)-1H-1,2,3-triazol-1-yl)tetrahydro-2H-pyran-3-ol (2 mg, 0.003 mmol, 5%) as an off-white solid and Example 10 (2R,3R,4S,5R,6R)-6-((3,4-dichlorophenyl)sulfonyl)-5-ethoxy-2-(hydroxymethyl)-4-(4-(3,4,5-trifluorophenyl)-1H-1,2,3-triazol-1-yl)tetrahydro-2H-pyran-3-ol (1.8 mg, 0.003 mmol, 4%) as an off-white solid.

Example 9 (Isomer-1)

LC-MS, [M+H]+=566.1, {Method A: tR=1.88 min}. 1H NMR (400 MHz, METHANOL-d4): δ 8.63 (s, 1H), 8.11-8.02 (m, 1H), 7.84-7.73 (m, 2H), 7.73-7.59 (m, 2H), 5.63 (dd, J=11.0, 3.0 Hz, 1H), 5.20 (d, J=5.5 Hz, 1H), 4.93 (dd, J=11.3, 5.3 Hz, 1H), 4.25 (d, J=1.5 Hz, 1H), 4.15 (t, J=6.0 Hz, 1H), 3.62-3.43 (m, 3H), 0.82 (t, J=7.0 Hz, 3H). hGal3 IC$_{50}$=0.1 uM.

Example 9 (Isomer-2)

LC-MS, [M+H]+=566.1, {Method A: tR=1.932 min}. 1H NMR (400 MHz, METHANOL-d4): δ 8.69 (s, 1H), 8.02 (d, J=2.0 Hz, 1H), 7.85-7.77 (m, 1H), 7.76-7.57 (m, 3H), 5.89-5.73 (m, 1H), 5.16 (d, J=6.5 Hz, 1H), 5.03 (dd, J=11.3, 6.3 Hz, 1H), 4.96 (t, J=6.5 Hz, 1H), 4.26 (d, J=1.5 Hz, 1H), 3.93-3.79 (m, 1H), 3.60-3.44 (m, 3H), 1.09 (t, J=7.0 Hz, 3H). hGal3 IC$_{50}$=0.34 uM.

Example 10

LC-MS, [M+H]+=582.1, {Method A: tR=2.01 min}. 1H NMR (400 MHz, METHANOL-d4): δ 8.65 (s, 1H), 8.19 (d, J=2.0 Hz, 1H), 7.95 (dd, J=8.5, 2.0 Hz, 1H), 7.84 (d, J=8.0 Hz, 1H), 7.76-7.60 (m, 2H), 5.75 (dd, J=11.5, 3.0 Hz, 1H), 5.69 (d, J=6.5 Hz, 1H), 4.95 (dd, J=11.5, 6.0 Hz, 1H), 4.54 (t, J=6.0 Hz, 1H), 4.28 (d, J=2.0 Hz, 1H), 3.81-3.68 (m, 1H), 3.62 (dd, J=11.8, 5.3 Hz, 1H), 3.55 (dd, J=11.5, 6.5 Hz, 1H), 3.41 (dq, J=9.0, 7.0 Hz, 1H), 0.91 (t, J=7.0 Hz, 3H). hGal3 IC$_{50}$=0.2 uM.

Example 11: Preparation of (2R,3R,4S,5R,6R)-6-((R)-(3,4-dichlorophenyl)sulfinyl)-2-(hydroxymethyl)-5-(2-methoxyethoxy)-4-(4-(3,4,5-trifluorophenyl)-1H-1,2,3-triazol-1-yl)tetrahydro-2H-pyran-3-ol

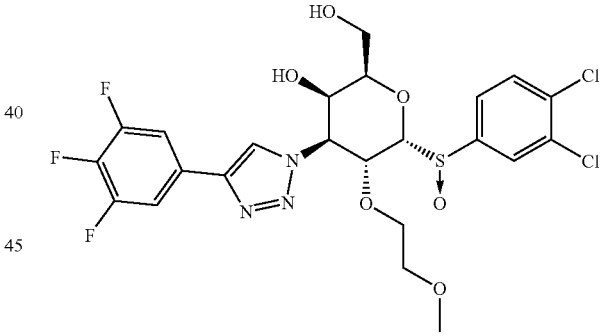

Prepared in a similar fashion as described in Example 2, step 1 using Example 7 (2R,3R,4S,5R,6R)-6-((3,4-dichlorophenyl)thio)-2-(hydroxymethyl)-5-(2-methoxyethoxy)-4-(4-(3,4,5-trifluorophenyl)-1H-1,2,3-triazol-1-yl)tetrahydro-2H-pyran-3-ol (20 mg, 0.034 mmol) and purified by prep-HPLC Method A to afford Example 11 (2R,3R,4S,5R,6R)-6-((R)-(3,4-dichlorophenyl)sulfinyl)-2-(hydroxymethyl)-5-(2-methoxyethoxy)-4-(4-(3,4,5-trifluorophenyl)-1H-1,2,3-triazol-1-yl)tetrahydro-2H-pyran-3-ol (5.2 mg, 0.009 mmol, 25%) as an off-white solid. LC-MS, [M+H]+=596.0, {Method A: tR=1.795 min}. 1H NMR (400 MHz, METHANOL-d4): δ 8.63 (s, 1H), 8.06 (s, 1H), 7.79 (d, J=1.0 Hz, 2H), 7.68 (dd, J=8.9, 6.7 Hz, 2H), 5.64 (dd, J=11.2, 2.7 Hz, 1H), 5.22 (d, J=5.6 Hz, 1H), 4.99 (dd, J=11.1, 5.3 Hz, 1H), 4.31 (d, J=2.4 Hz, 1H), 4.15 (t, J=6.2 Hz, 1H), 3.61-3.45 (m, 4H), 3.18 (t, J=4.6 Hz, 2H), 3.11 (s, 3H). hGal3 IC$_{50}$=0.056 uM.

Example 12: Preparation of (2R,3R,4S,5R,6R)-6-((3,4-dichlorophenyl)sulfonyl)-2-(hydroxymethyl)-5-(2-methoxy ethoxy)-4-(4-(3,4,5-trifluorophenyl)-1H-1,2,3-triazol-1-yl)tetrahydro-2H-pyran-3-ol

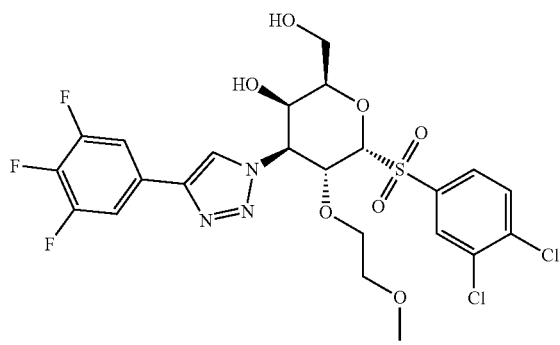 [SMILES: COCCO[C@@H]1[C@@H](n2cc(-c3cc(F)c(F)c(F)c3)nn2)[C@@H](O)[C@@H](CO)O[C@@H]1S(=O)(=O)c1ccc(Cl)c(Cl)c1]

To a stirred solution of Example 7 (2R,3R,4S,5R,6R)-6-((3,4-dichlorophenyl)thio)-2-(hydroxymethyl)-5-(2-methoxyethoxy)-4-(4-(3,4,5-trifluorophenyl)-1H-1,2,3-triazol-1-yl)tetrahydro-2H-pyran-3-ol (20 mg, 0.034 mmol) in DCM (5 mL), mCPBA (11.89 mg, 0.048 mmol) was added at 0° C. under nitrogen and stirred for 15 min. Then reaction mixture was diluted with DCM (40 mL), washed with aq.NaHCO 3 solution, water, brine and dried over sodium sulphate. Solvent was removed under reduced pressure to get the crude residue which was purified via prep-HPLC Method A to afford Example 12 (2R,3R,4S,5R,6R)-6-((3,4-dichlorophenyl)sulfonyl)-2-(hydroxymethyl)-5-(2-methoxyethoxy)-4-(4-(3,4,5-trifluorophenyl)-1H-1,2,3-triazol-1-yl)tetrahydro-2H-pyran-3-ol (5.7 mg, 0.009 mmol, 26%) as an off-white solid. LC-MS, [M+H]+=612.1, {Method B: tR=1.847 min}. 1H NMR (400 MHz, METHANOL-d4): δ 8.63 (s, 1H), 8.17 (d, J=2.2 Hz, 1H), 7.93 (dd, J=8.4, 2.1 Hz, 1H), 7.83 (d, J=8.3 Hz, 1H), 7.74-7.57 (m, 2H), 5.75 (dd, J=11.4, 2.8 Hz, 1H), 5.68 (d, J=6.1 Hz, 1H), 4.98 (dd, J=11.5, 6.4 Hz, 1H), 4.53 (t, J=5.9 Hz, 1H), 4.30 (d, J=2.0 Hz, 1H), 3.81-3.70 (m, 1H), 3.63-3.48 (m, 3H), 3.28-3.22 (m, 2H), 3.12 (s, 3H). hGal3 IC$_{50}$=0.13 uM.

Example 13: Preparation of (4-(2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)ethyl)morpholine 4-oxide

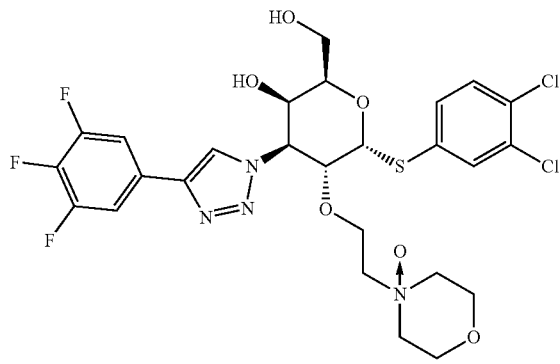 [SMILES: [O-][N+]1(CCO[C@@H]2[C@@H](n3cc(-c4cc(F)c(F)c(F)c4)nn3)[C@@H](O)[C@@H](CO)O[C@@H]2Sc2ccc(Cl)c(Cl)c2)CCOCC1]

To a stirred solution of Example 8 (2R,3R,4S,5R,6R)-6-((3,4-dichlorophenyl)thio)-2-(hydroxymethyl)-5-(2-morpholinoethoxy)-4-(4-(3,4,5-trifluorophenyl)-1H-1,2,3-triazol-1-yl)tetrahydro-2H-pyran-3-ol (18 mg, 0.028 mmol) in DCM (5 mL), mCPBA (6.28 mg, 0.025 mmol) was added at 0° C. under nitrogen and stirred for 15 min. Then reaction mixture was diluted with DCM (40 mL), washed with aq.NaHCO 3 solution, water, brine and dried over sodium sulphate. Solvent was removed under reduced pressure to get the crude residue which was purified via prep-HPLC Method A to afford Example 13 (4-(2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)ethyl)morpholine 4-oxide (7.5 mg, 0.011 mmol, 39%) as an off-white solid. LC-MS, [M+H]+=651.2, {Method A: tR=1.362 min}. 1H NMR (400 MHz, METHANOL-d4): δ 8.69 (s, 1H), 7.86 (d, J=2.2 Hz, 1H), 7.69 (dd, J=8.7, 7.0 Hz, 2H), 7.57 (dd, J=8.4, 2.1 Hz, 1H), 7.50 (d, J=8.6 Hz, 1H), 6.24 (d, J=5.4 Hz, 1H), 5.07 (dd, J=11.1, 2.8 Hz, 1H), 4.75 (dd, J=11.0, 5.4 Hz, 1H), 4.48 (t, J=6.0 Hz, 1H), 4.24 (dd, J=11.2, 4.9 Hz, 1H), 4.18 (d, J=2.2 Hz, 1H), 4.12-3.89 (m, 2H), 3.83 (t, J=10.8 Hz, 1H), 3.76-3.59 (m, 3H), 3.48 (dd, J=13.7, 7.3 Hz, 1H), 3.38-3.34 (m, 1H), 3.26 (d, J=3.9 Hz, 1H), 3.11-2.96 (m, 2H), 2.42 (d, J=13.9 Hz, 1H). hGal3 IC$_{50}$=0.05 uM.

Example 14: Preparation of ethyl 2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)acetate

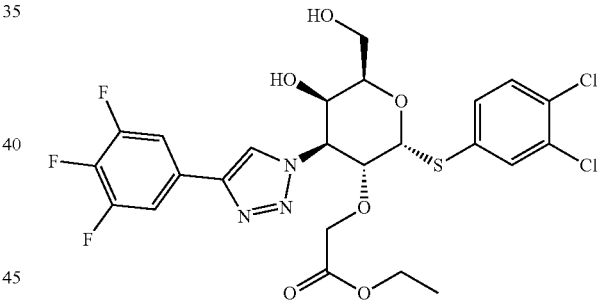

Step 1: Synthesis of ethyl 2-(((4aR,6R,7R,8S,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)acetate: To a stirred solution of (4aR,6R,7R,8R,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-ol (200 mg, 0.328 mmol) in DMF (5 mL), ethyl 2-bromoacetate (0.057 mL, 0.491 mmol), silver oxide (380 mg, 1.638 mmol) and potassium iodide (109 mg, 0.655 mmol) were added sequentially at rt and stirred for overnight. Then, reaction mixture was diluted with EtOAc (30 mL), filtered through celite pad and washed with excess EtOAc. Filtrate was washed with water, brine, dried over sodium sulphate and concentrated to afford ethyl 2-(((4aR,6R,7R,8S,8aR)-6-((3,4-dichlorophenyl)thio)-2-phenyl-8-(4-(3,4,5-trifluorophenyl)-1H-1,2,3-triazol-1-yl) hexahydropyrano[3,2-d][1,3]dioxin-7-yl)oxy)acetate (0.2 g, 0.29 mmol, 88%) as an off-white solid which as such taken for next step without further purification. LC-MS, [M+H]+=697.4, {Method C: tR: 3.926 min}.

Step 2: Synthesis of ethyl 2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)acetate: Prepared in a similar fashion as described in Example 1, step 9 using ethyl 2-(((4aR,6R,7R,8S,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)acetate (32 mg, 0.046 mmol) and purified by prep-HPLC Method A to afford Example 14 ethyl 2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)acetate (9.9 mg, 0.016 mmol, 35%) as an off-white solid. LC-MS, [M+H]+=608.1, {Method A: tR=2.166 min}. 1H NMR (400 MHz, METHANOL-d4): δ 8.75 (s, 1H), 7.85 (d, J=2.0 Hz, 1H), 7.66 (dd, J=9.0, 6.5 Hz, 2H), 7.58 (dd, J=8.5, 2.0 Hz, 1H), 7.51 (d, J=8.5 Hz, 1H), 6.27 (d, J=5.5 Hz, 1H), 5.09 (dd, J=11.3, 2.8 Hz, 1H), 4.96-4.93 (m, 1H), 4.57 (s, 1H), 4.50 (t, J=6.0 Hz, 1H), 4.31-4.20 (m, 3H), 4.16 (q, J=7.5 Hz, 2H), 3.83-3.63 (m, 2H), 1.27-1.16 (m, 3H). hGal3 IC$_{50}$=0.38 uM.

Example 15: Preparation of 2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)acetonitrile

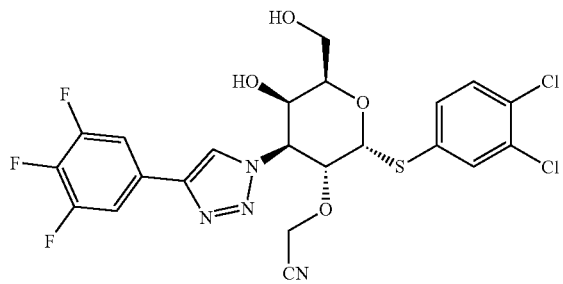 [SMILES: N#CCO[C@@H]1[C@@H](n2cc(-c3cc(F)c(F)c(F)c3)nn2)[C@@H](O)[C@@H](CO)O[C@@H]1Sc1ccc(Cl)c(Cl)c1]

Step 1: Synthesis of 2-(((4aR,6R,7R,8S,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)acetonitrile: Prepared in a similar fashion as described in Example 14, step 1 using (4aR,6R,7R,8R,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-ol (50 mg, 0.082 mmol) to afford 2-(((4aR,6R,7R,8S,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)acetonitrile (0.05 g, 0.077 mmol, 51%) as an off-white solid which was as such taken for next step without further purification. LC-MS, [M+2]+=651.0, {Method C: tR: 3.896 min, purity: 54%}.

Step 2: Synthesis of 2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)acetonitrile: Prepared in a similar fashion as described in Example 1, step 9 using 2-(((4aR,6R,7R,8S,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)acetonitrile (40 mg, 0.062 mmol) and purified by prep-HPLC Method A to afford Example 15 2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)acetonitrile (4.9 mg, 0.009 mmol, 14%) as an off-white solid. LC-MS, [M+H]+=561.1, {Method B: tR=1.986 min}. 1H NMR (400 MHz, METHANOL-d4): δ 8.58 (s, 1H), 7.87 (d, J=2.0 Hz, 1H), 7.71-7.61 (m, 2H), 7.59 (dd, J=8.3, 2.3 Hz, 1H), 7.52 (d, J=8.5 Hz, 1H), 6.25 (d, J=5.5 Hz, 1H), 5.11 (dd, J=11.3, 2.8 Hz, 1H), 4.95 (dd, J=11.5, 5.5 Hz, 1H), 4.57-4.47 (m, 3H), 4.24 (d, J=2.5 Hz, 1H), 3.82-3.65 (m, 2H). hGal3 IC$_{50}$=0.23 uM.

Example 16 and Example 17: Preparation of ethyl 2-(((2R,3R,4S,5R,6R)-2-((S)-(3,4-dichlorophenyl)sulfinyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetate and ethyl 2-(((2R,3R,4S,5R,6R)-2-((3,4-dichlorophenyl)sulfonyl)-5-hydroxy-6-(hydroxymethyl)-4-(4-(3,4,5-trifluorophenyl)-1H-1,2,3-triazol-1-yl)tetrahydro-2H-pyran-3-yl)oxy) acetate

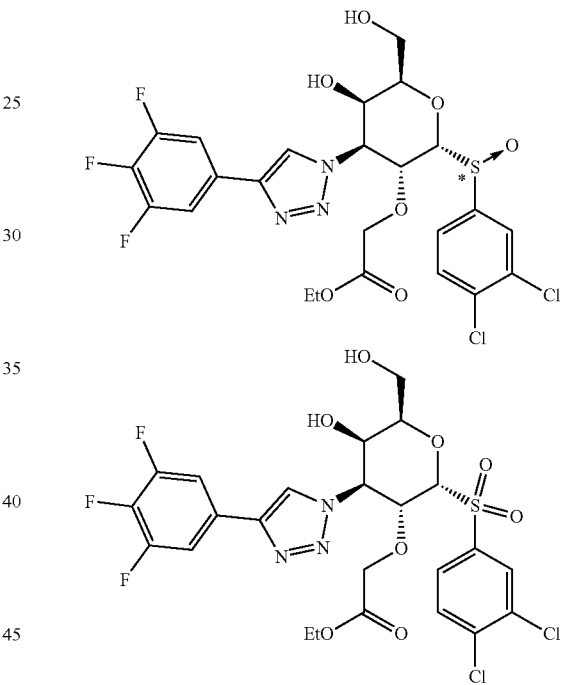

Prepared in a similar fashion as described in Example-2 & Example-3, step 1 using Example 14 ethyl 2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)acetate (85 mg, 0.140 mmol) and purified by prep-HPLC Method G to afford Example 16 ethyl 2-(((2R,3R,4S,5R,6R)-2-((S)-(3,4-dichlorophenyl)sulfinyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetate (14 mg, 0.022 mmol, 15%) as an off-white solid and Example 17 ethyl 2-(((2R,3R,4S,5R,6R)-2-((3,4-dichlorophenyl)sulfonyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetate (23 mg, 0.035 mmol, 24%) as an off-white solid.

Example 16

LC-MS, [M−H]+=624.4, {Method C: tR=2.634 min}. 1H NMR (400 MHz, METHANOL-d4): δ 8.73 (s, 1H), 8.05 (d, J=1.5 Hz, 1H), 7.80-7.77 (m, 2H), 7.66 (dd, J=9.0, 6.5 Hz, 2H), 5.73 (dd, J=11.0, 3.0 Hz, 1H), 5.39 (d, J=5.5 Hz, 1H), 5.15 (dd, J=11.0, 5.5 Hz, 1H), 4.31 (d, J=2.0 Hz, 1H), 4.23-4.16 (m, 1H), 4.14-3.94 (m, 4H), 3.62-3.47 (m, 2H), 1.17 (t, J=7.3 Hz, 2H). hGal3 IC$_{50}$=0.025 uM.

Example 17

LC-MS, [M−H]+=640.3, {Method C: tR=2.864 min}. 1H NMR (400 MHz, METHANOL-d4): δ 8.74 (s, 1H), 8.18 (d, J=2.0 Hz, 1H), 7.97-7.91 (m, 1H), 7.85-7.80 (m, 1H), 7.70-7.63 (m, 2H), 5.87-5.81 (m, 2H), 5.15 (dd, J=11.3, 6.3 Hz, 1H), 4.57 (t, J=5.8 Hz, 1H), 4.32 (d, J=2.0 Hz, 1H), 4.23-4.12 (m, 2H), 4.12-4.02 (m, 2H), 3.67-3.56 (m, 2H), 1.22-1.17 (t, J=7.2 Hz, 3H). hGal3 IC$_{50}$=0.19 uM.

Example 18: Preparation of 2-(((2R,3R,4S,5R,6R)-2-((S)-(3,4-dichlorophenyl)sulfinyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid

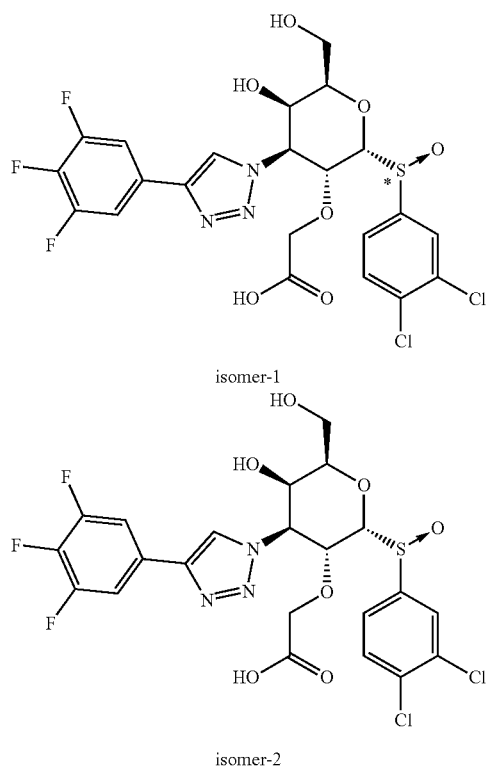

isomer-1 isomer-2

Prepared in a similar fashion as described in Example-2, step-1 using Example 5 2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid (160 mg, 0.276 mmol) and purified by prep-HPLC Method B to afford Example-18 (isomer-1) 2-(((2R,3R,4S,5R,6R)-2-((S)-(3,4-dichlorophenyl)sulfinyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid as an off-white solid (18 mg, 0.030 mmol, 10%) and Example-18 (isomer-2) 2-(((2R,3R,4S,5R,6R)-2-((S)-(3,4-dichlorophenyl)sulfinyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid as an off-white solid (3 mg, 0.005, 2%). Isomer-1: LC-MS, [M−H]+=594.0, {Method C: tR=1.242 min}. 1H NMR (400 MHz, DMSO-d6): δ 9.45 (s, 1H), 8.04 (d, J=1.5 Hz, 1H), 7.87-7.77 (m, 2H), 7.76-7.68 (m, 2H), 5.66 (dd, J=11.3, 2.8 Hz, 1H), 5.54 (d, J=5.0 Hz, 1H), 5.39 (d, J=5.5 Hz, 1H), 5.07-4.98 (m, 1H), 4.75-4.68 (m, 1H), 4.19-4.10 (m, 2H), 3.81 (br. s., 1H), 3.21 (d, J=5.0 Hz, 2H). hGal3 IC$_{50}$=0.017 uM.

Isomer-2: LC-MS, [M−H]+=596.1, {Method A: tR=1.062 min}. 1H NMR (400 MHz, METHANOL-d4): δ 8.82 (s, 1H), 8.04 (d, J=2.0 Hz, 1H), 7.80 (d, J=8.5 Hz, 1H), 7.75 (dd, J=8.5, 2.0 Hz, 1H), 7.69 (dd, J=9.0, 6.5 Hz, 2H), 5.83 (dd, J=11.3, 2.8 Hz, 1H), 5.36 (d, J=6.5 Hz, 1H), 5.16 (dd, J=11.0, 6.5 Hz, 1H), 5.09 (t, J=6.5 Hz, 1H), 4.31-4.20 (m, 2H), 4.06 (d, J=16.6 Hz, 1H), 3.59-3.46 (m, 2H). hGal3 IC$_{50}$=0.1 uM.

Example 19: Preparation of 2-(((2R,3R,4S,5R,6R)-2-((3,4-dichlorophenyl)sulfonyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid

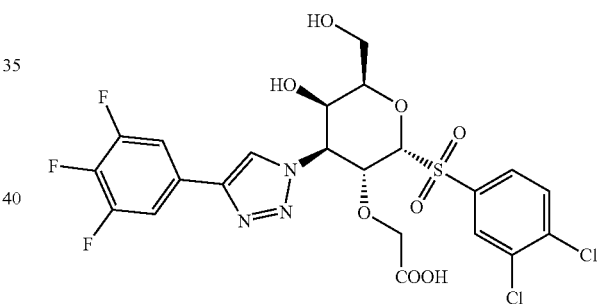

To a stirred suspension of Example 17 ethyl 2-(((2R,3R,4S,5R,6R)-2-((3,4-dichlorophenyl)sulfonyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetate (20 mg, 0.031 mmol) in THF (5 mL) and water (1 mL), lithium hydroxide (3.74 mg, 0.156 mmol) was added at rt and stirred at rt for 30 min. Solvent was removed under reduced pressure, neutralized with AcOH and purified by prep-HPLC Method F to afford Example 19 2-(((2R,3R,4S,5R,6R)-2-((3,4-dichlorophenyl)sulfonyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid (5.6 mg, 0.009 mmol, 28%) as an off-white solid. LC-MS, [M+H]+=612.0, {Method A: tR=1.17 min}. 1H NMR (400 MHz, METHANOL-d4): δ 9.10 (s, 1H), 8.18 (d, J=2.0 Hz, 1H), 8.01-7.91 (m, 1H), 7.80 (d, J=8.5 Hz, 1H), 7.69 (dd, J=9.0, 6.5 Hz, 2H), 5.93 (d, J=6.0 Hz, 1H), 5.87 (dd, J=11.5, 3.0 Hz, 1H), 5.26 (dd, J=11.3, 5.8 Hz, 1H), 4.58 (t, J=5.5 Hz, 1H), 4.33 (d, J=1.5 Hz, 1H), 3.97 (d, J=16.1 Hz, 1H), 3.75 (d, J=16.1 Hz, 1H), 3.67-3.55 (m, 2H). hGal3 IC$_{50}$=0.06 uM.

General Synthetic Scheme for C2-Acetic Acid Amide Series:

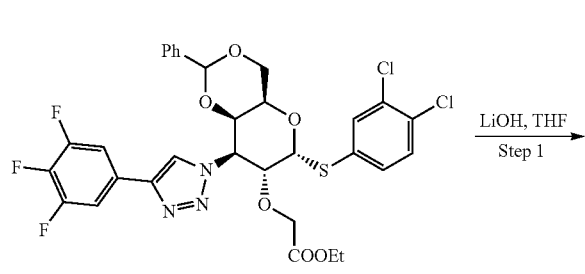

Example 20: Preparation of 2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)-1-(4-hydroxypiperidin-1-yl)ethan-1-one

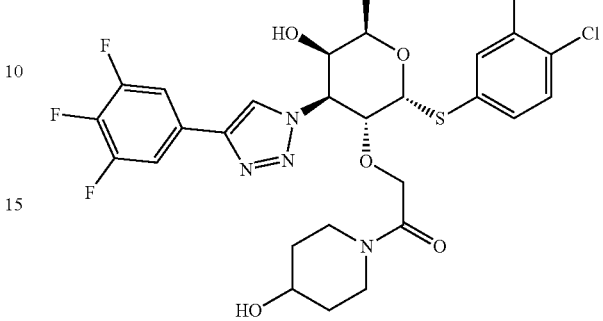

Step 1: Synthesis of 2-(((4aR,6R,7R,8S,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)acetic acid: To a stirred solution of ethyl 2-(((4aR,6R,7R,8S,8aR)-6-((3,4-dichlorophenyl)thio)-2-phenyl-8-(4-(3,4,5-trifluorophenyl)-1H-1,2,3-triazol-1-yl) hexahydropyrano[3,2-d][1,3]dioxin-7-yl)oxy)acetate (590 mg, 0.847 mmol) in THF (10 mL), LiOH (101 mg, 4.24 mmol) in water (5 mL) was added at rt and stirred for 30 min. Then the reaction mixture was concentrated to remove THF and diluted with Water (20 mL). Aqueous layer pH was adjusted to 2-3 using 1.5 N HCl solution and stirred for 10 min. Then the obtained solid was filtered, washed with excess water and dried to afford 2-(((4aR,6R,7R,8S,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)acetic acid (0.48 g, 0.718 mmol, 83%) as an off-white solid. LC-MS, [M+1]+=669.0, {Method C: tR: 2.588 min}

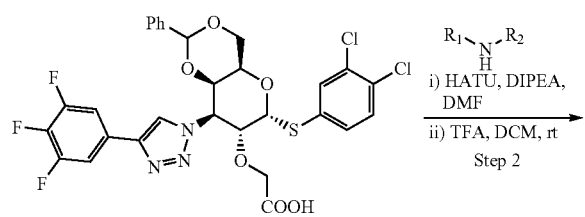

Step 2: Synthesis of 2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)-1-(4-hydroxypiperidin-1-yl)ethan-1-one:
To a stirred solution of 2-(((4aR,6R,7R,8S,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)acetic acid (14 mg, 0.021 mmol) and 4-hydroxy piperidine (2.5 mg, 0.023 mmol) in DMF (1.5 mL), HATU (19.91 mg, 0.052 mmol) was added followed by DIPEA (0.018 mL, 0.105 mmol) at rt and stirred for overnight. Then the solvent was removed under reduced pressure to give the crude residue which was dissolved in 20% TFA in DCM (1.5 mL, 19.47 mmol) and stirred at rt for 2 h. Solvent was removed under reduced pressure and purified by prep-HPLC Method A to afford Example 20 2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)-1-(4-hydroxypiperidin-1-yl)ethan-1-one (2.4 mg, 0.004 mmol, 17%). LC-MS, [M+H]+= 663.1, {Method A: tR=1.635 min. $^1$H NMR (400 MHz, METHANOL-d$_4$): δ ppm 8.71 (d, J=4.2 Hz, 1H), 7.86-7.83 (m, 1H), 7.69-7.63 (m, 2H), 7.59-7.54 (m, 1H), 7.52-7.46 (m, 1H), 6.25-6.21 (m, 1H), 5.09 (dd, J=2.8, 11.4 Hz, 1H), 4.89 (dd, J=4.9, 6.6 Hz, 1H), 4.52-4.45 (m, 1H), 4.38-4.31 (m, 1H), 4.28-4.20 (m, 2H), 3.93-3.81 (m, 1H), 3.76-3.66 (m, 3H), 3.54-3.42 (m, 1H), 3.15-2.96 (m, 2H), 1.78-1.58 (m, 2H), 1.41-1.27 (m, 2H). hGal3 IC$_{50}$=0.04 uM.

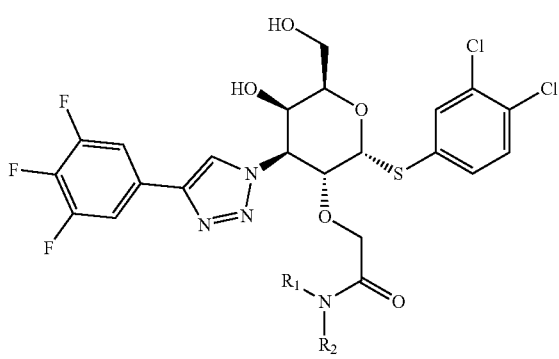

| Ex. | hGal3 IC$_{50}$ (uM) | Structure | LCMS RT | M + H | Method |
|---|---|---|---|---|---|
| 21 | 0.225 | 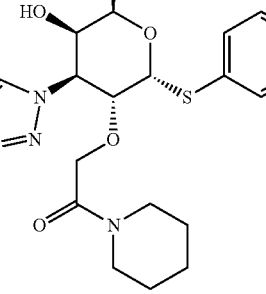 | 2.17 | 647.2 | A |
| 22 | 0.043 | 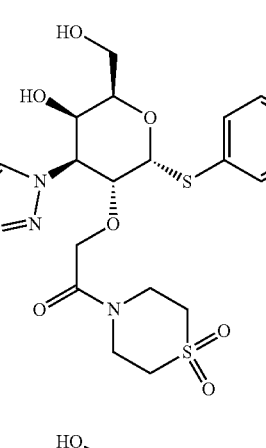 | 1.62 | 697 | A |
| 23 | 0.06 | 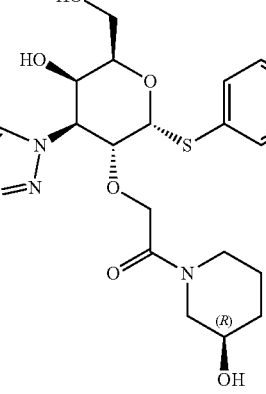 | 1.768 | 663.2 | A |
| 24 | 0.15 | 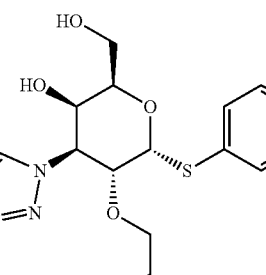 | 2.095 | 683.2 | A |

-continued

| Ex. | hGal3 IC$_{50}$ (uM) | Structure | LCMS RT | M + H | Method |
|---|---|---|---|---|---|
| 25 | 0.076 | 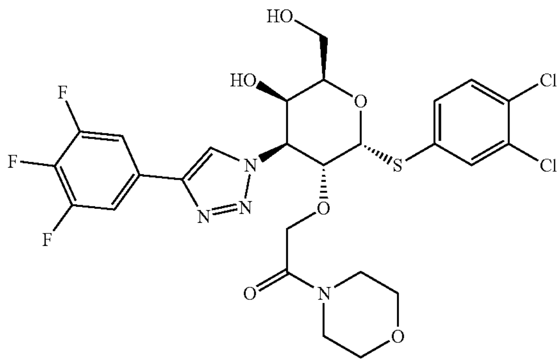 [SMILES: O=C(CO[C@@H]1[C@@H](n2cc(-c3cc(F)c(F)c(F)c3)nn2)[C@@H](O)[C@@H](CO)O[C@@H]1Sc1ccc(Cl)c(Cl)c1)N1CCOCC1] | 1.85 | 649.2 | A |
| 26 | 0.086 | 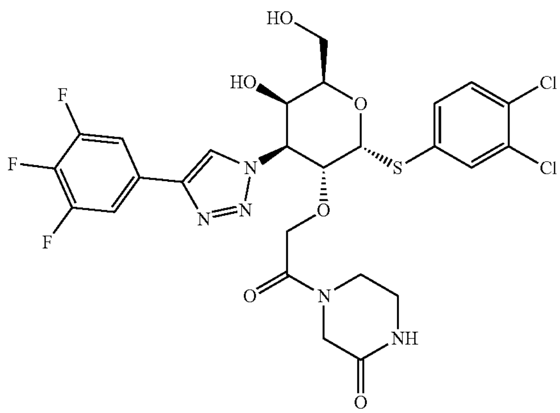 [SMILES: O=C1CN(C(=O)CO[C@@H]2[C@@H](n3cc(-c4cc(F)c(F)c(F)c4)nn3)[C@@H](O)[C@@H](CO)O[C@@H]2Sc2ccc(Cl)c(Cl)c2)CCN1] | 1.40 | 662.1 | A |
| 27 | 0.070 | 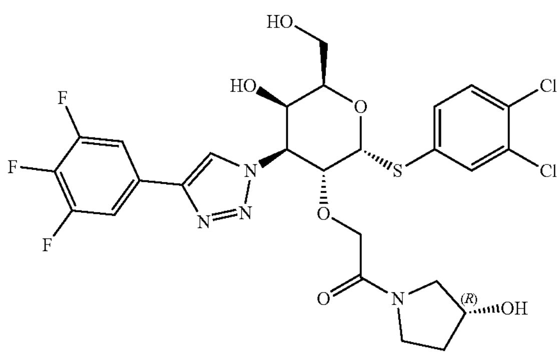 | 1.62 | 649.1 | B |
| 28 | 0.048 | 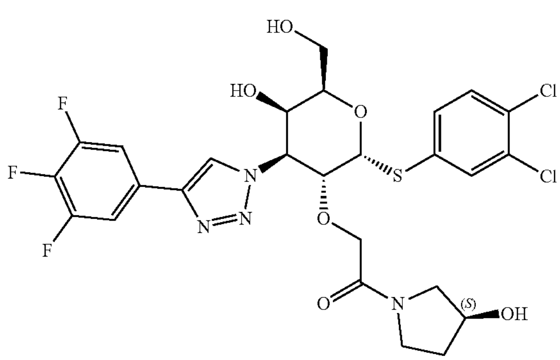 | 1.63 | 649.1 | B |

-continued
| Ex. | hGal3 IC$_{50}$ (uM) | Structure | LCMS RT | M + H | Method |
|---|---|---|---|---|---|
| 29 | 0.072 | 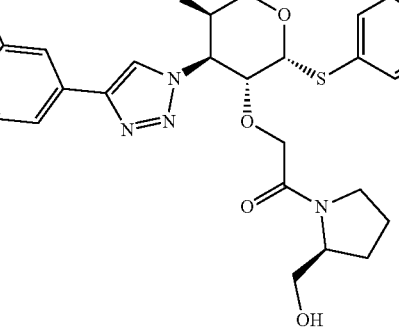 | 1.80 | 663.1 | B |
| 30 | 0.8 | 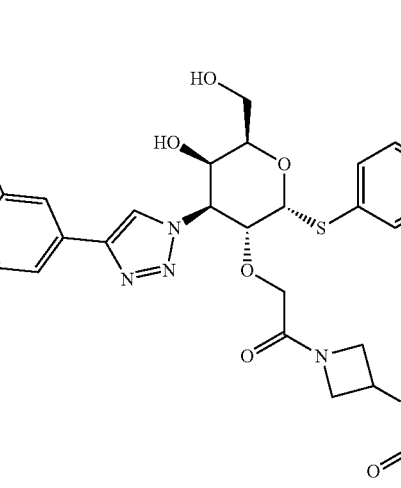 | 1.56 | 676.3 | B |
| 31 | 0.09 | 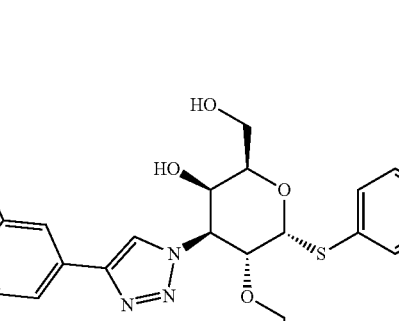 | 1.56 | 635.1 | B |

-continued
| Ex. | hGal3 IC$_{50}$ (uM) | Structure | LCMS RT | M + H | Method |
|---|---|---|---|---|---|
| 32 | 0.7 | 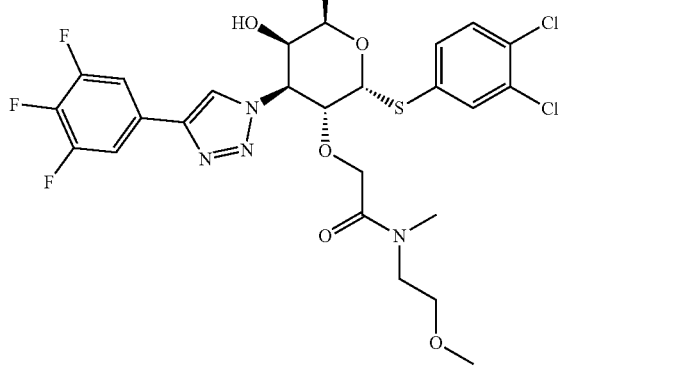 | 1.95 | 651.1 | B |
| 33 | 0.06 | 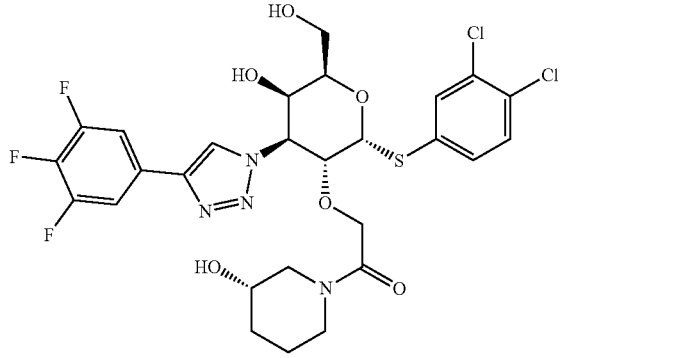 [SMILES: O=C(CO[C@@H]1[C@@H](n2cc(-c3cc(F)c(F)c(F)c3)nn2)[C@@H](O)[C@@H](CO)O[C@@H]1Sc1ccc(Cl)c(Cl)c1)N1CCC[C@H](O)C1] | 1.77 | 663.2 | A |
| 34 | 0.66 | 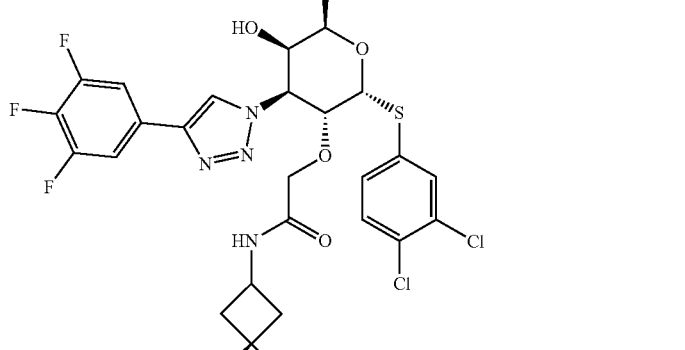 | 1.70 | 689.2 | A |

General Synthetic Scheme for Sulfoxide Synthesis:

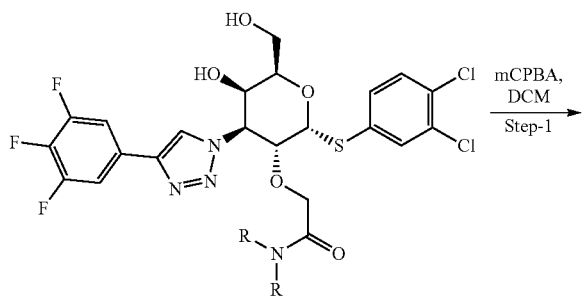

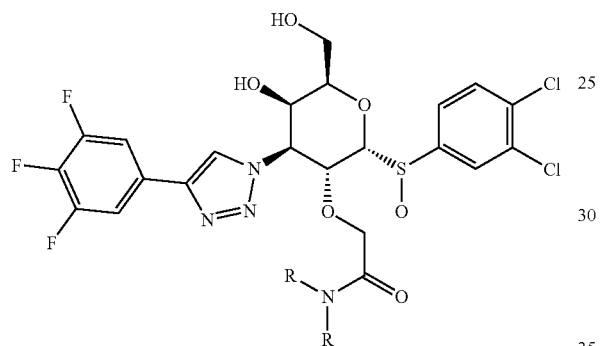

Example 35: Preparation of 2-(((2R,3R,4S,5R,6R)-2-((R)-(3,4-dichlorophenyl)sulfinyl)-5-hydroxy-6-(hydroxymethyl)-4-(4-(3,4,5-trifluorophenyl)-1H-1,2,3-triazol-1-yl)tetrahydro-2H-pyran-3-yl)oxy)-1-(1,1-dioxidothiomorpholino)ethan-1-one

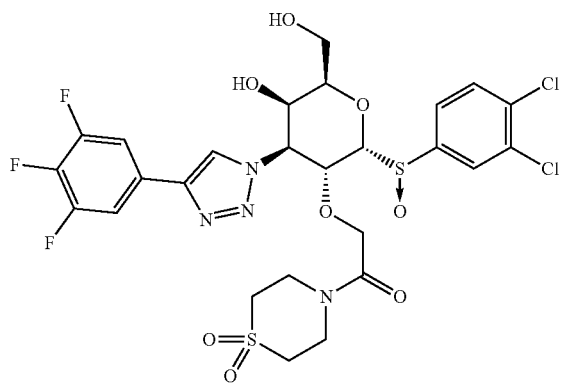 [SMILES: O=C(CO[C@@H]1[C@@H](n2cc(-c3cc(F)c(F)c(F)c3)nn2)[C@@H](O)[C@@H](CO)O[C@@H]1S(=O)c1ccc(Cl)c(Cl)c1)N1CCS(=O)(=O)CC1]

Prepared in a similar fashion as described in Example-2, step-1 using Example 22 2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)-1-(1,1-dioxidothiomorpholino)ethan-1-one (0.05 g, 0.072 mmol) as the reactant and purified by prep-HPLC Method A to afford Example 35 2-(((2R,3R,4S,5R,6R)-2-((S)-(3,4-dichlorophenyl)sulfinyl)-5-hydroxy-6-(hydroxymethyl)-4-(4-(3,4,5-trifluorophenyl)-1H-1,2,3-triazol-1-yl)tetrahydro-2H-pyran-3-yl)oxy)-1-(1,1-dioxidothiomorpholino)ethan-1-one (6.4 mg, 8.86 μmol, 12%). LC-MS, [M+H]$^+$=715.1, {Method A: tR=1.44 min}. hGal3 IC$_{50}$=0.05 uM. 1H NMR (400 MHz, METHANOL-d4) δ 8.73 (s, 1H), 8.07 (s, 1H), 7.80 (s, 2H), 7.69 (dd, J=8.8, 6.6 Hz, 2H), 5.71 (dd, J=11.1, 2.8 Hz, 1H), 5.32 (d, J=5.4 Hz, 1H), 5.13 (dd, J=11.1, 5.3 Hz, 1H), 4.37 (d, J=13.7 Hz, 1H), 4.29 (d, J=2.0 Hz, 1H), 4.20-4.19 (m, 1H), 4.16-4.04 (m, 1H), 3.90-4.87 (m, 1H), 3.80-3.79 (m, 1H), 3.69-3.66 (m, 2H), 3.55 (dd, J=11.6, 5.5 Hz, 1H), 3.46 (dd, J=11.6, 5.5 Hz, 1H), 3.10-3.07 (m, 2H), 3.1-2.9 (m, 2H).

Example 36: Preparation of 2-(((2R,3R,4S,5R,6R)-2-((S)-(3,4-dichlorophenyl)sulfinyl)-5-hydroxy-6-(hydroxymethyl)-4-(4-(3,4,5-trifluorophenyl)-1H-1,2,3-triazol-1-yl)tetrahydro-2H-pyran-3-yl)oxy)-1-((S)-3-hydroxypiperidin-1-yl)ethan-1-one

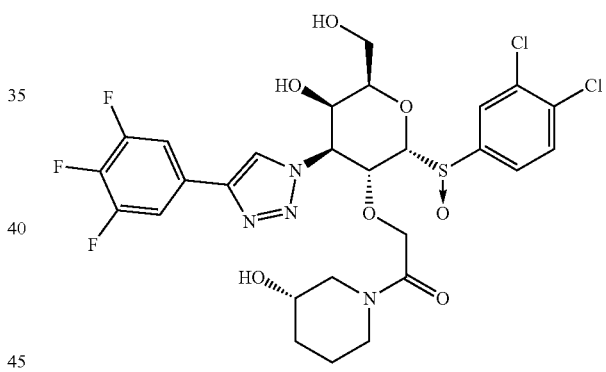

Prepared in a similar fashion as described in Example-2, step-1 using Example 33 2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)-1-((S)-3-hydroxypiperidin-1-yl)ethan-1-one (0.05 g, 0.075 mmol) and purified by prep-HPLC Method A to afford Example 36 2-(((2R,3R,4S,5R,6R)-2-((S)-(3,4-dichlorophenyl)sulfinyl)-5-hydroxy-6-(hydroxymethyl)-4-(4-(3,4,5-trifluorophenyl)-1H-1,2,3-triazol-1-yl)tetrahydro-2H-pyran-3-yl)oxy)-1-((S)-3-hydroxypiperidin-1-yl)ethan-1-one (7.8 mg, 10.89 μmol, 14%). LC-MS, [M+H]+=679.2, {Method A: tR=1.49 min}. 1H NMR (400 MHz, METHANOL-d4) δ 8.73 (d, J=3.4 Hz, 1H), 8.06 (d, J=12.2 Hz, 1H), 7.86-7.74 (m, 2H), 7.74-7.56 (m, 2H), 5.80-5.66 (m, 1H), 5.46-5.30 (m, 1H), 5.16-5.05 (m, 1H), 4.32-4.01 (d, J=9.5 Hz, 4H), 3.62-3.42 (m, 3H), 3.24 (d, J=13.0 Hz, 1H), 3.06 (dd, J=13.6, 6.5 Hz, 1H), 2.66 (d, J=14.4 Hz, 1H), 2.56-2.45 (m, 1H), 1.92-1.65 (m, 2H), 1.55-1.22 (m, 2H). hGal3 IC$_{50}$=0.07 uM.

Example 37: Preparation of 2-(((2R,3R,4S,5R,6R)-2-((S)-(3,4-dichlorophenyl)sulfinyl)-5-hydroxy-6-(hydroxymethyl)-4-(4-(3,4,5-trifluorophenyl)-1H-1,2,3-triazol-1-yl)tetrahydro-2H-pyran-3-yl)oxy)-1-morpholinoethan-1-one

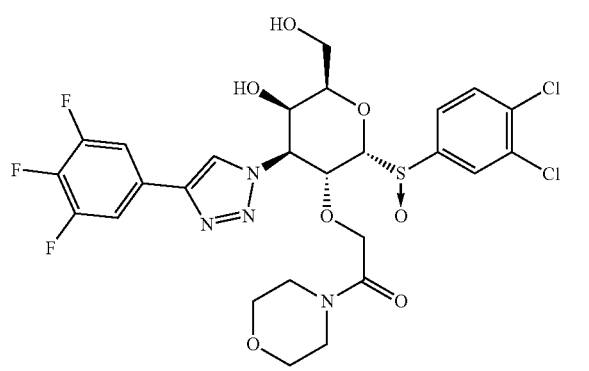 [SMILES: O=C(CO[C@@H]1[C@@H](n2cc(-c3cc(F)c(F)c(F)c3)nn2)[C@@H](O)[C@@H](CO)O[C@@H]1S(=O)c1ccc(Cl)c(Cl)c1)N1CCOCC1]

Prepared in a similar fashion as described in Example-2, step-1 using Example 25 2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)-1-morpholinoethan-1-one (0.05 g, 0.077 mmol) and purified by prep-HPLC Method A to afford Example 37 2-(((2R,3R,4S,5R,6R)-2-((S)-(3,4-dichlorophenyl)sulfinyl)-5-hydroxy-6-(hydroxymethyl)-4-(4-(3,4,5-trifluorophenyl)-1H-1,2,3-triazol-1-yl)tetrahydro-2H-pyran-3-yl)oxy)-1-morpholinoethan-1-one (77.2 mg, 10.22 µmol, 13%). LC-MS, [M+H]+=665.2, {Method A: tR=1.54 min}. 1H NMR (400 MHz, METHANOL-d4) δ 8.72 (s, 1H), 8.06 (s, 1H), 7.78 (s, 2H), 7.74-7.62 (m, 2H), 5.75 (dd, J=11.1, 2.8 Hz, 1H), 5.37 (d, J=5.4 Hz, 1H), 5.13 (dd, J=11.2, 5.1 Hz, 1H), 4.31-4.29 (m, 1H), 4.24-4.14 (m, 2H), 4.14-4.05 (m, 1H), 3.64-3.37 (m, 6H), 3.4-3.3 (m, 2H) (merged in-solvent peak) 3.19-3.17 (m, 2H). hGal3 IC$_{50}$=0.08 uM.

General Synthetic Scheme:

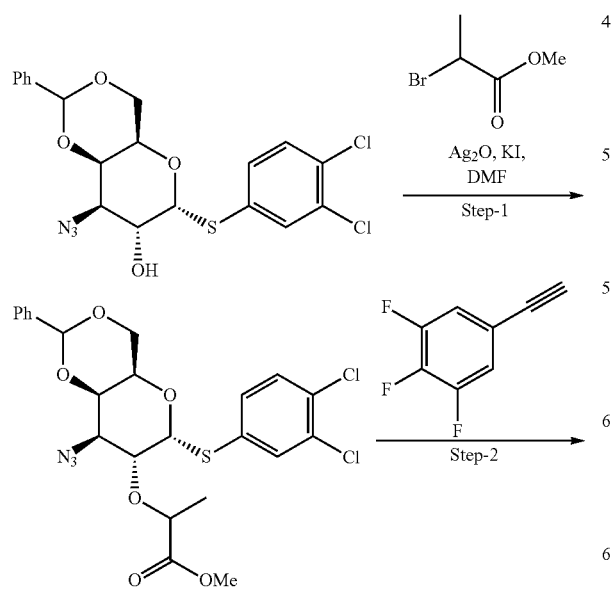

Example 38: Preparation of 2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)propanoic acid

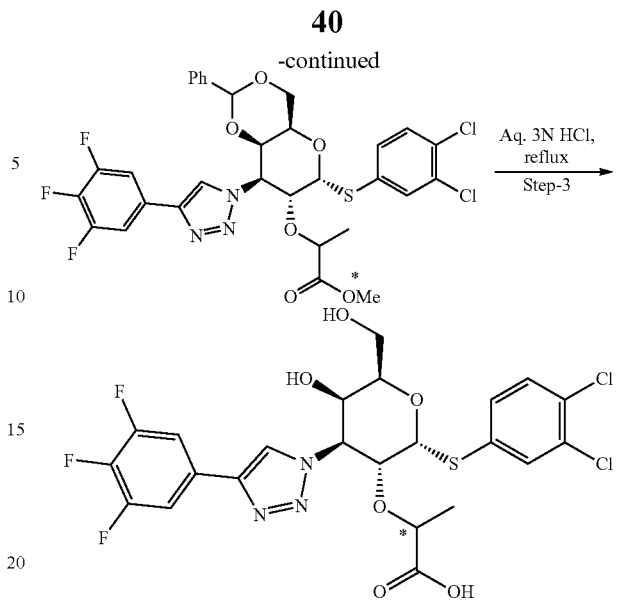

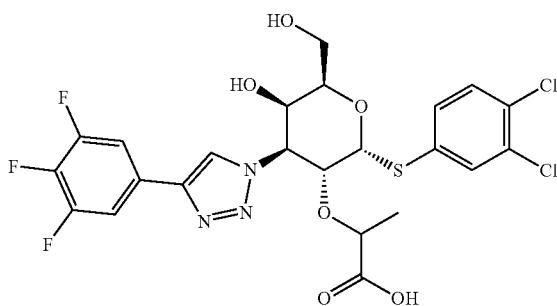 [SMILES: CC(O[C@@H]1[C@@H](n2cc(-c3cc(F)c(F)c(F)c3)nn2)[C@@H](O)[C@@H](CO)O[C@@H]1Sc1ccc(Cl)c(Cl)c1)C(=O)O]

Step 1: Synthesis of methyl 2-4(4aR,6R,7R,8S,8aR)-8-azido-6-((3,4-dichlorophenyl)thio)-2-phenylhexahydropyrano[3,2-d][1,3]dioxin-7-yl)oxy)propanoate: Prepared in a similar fashion as described in Example 14, step 1 using ((4aR,6R,7R,8S,8aR)-8-azido-6-((3,4-dichlorophenyl)thio)-2-phenylhexahydropyrano[3,2-d][1,3]dioxin-7-ol (100 mg, 0.220 mmol), and methyl 2-bromopropanoate (73.5 mg, 0.440 mmol) as the reactants to afford methyl 2-(((4aR,6R,7R,8S,8aR)-8-azido-6-((3,4-dichlorophenyl)thio)-2-phenylhexahydropyrano[3,2-d][1,3]dioxin-7-yl)oxy)propanoate (110 mg, 0.204 mmol, 92%, diastereomeric mixture) as an off-white solid. LC-MS, [M+18]+=557.4, {Method E: tR=1.72 min}.

Step 2: Synthesis of 2 methyl 2-(((4aR,6R,7R,8S,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)propanoate: Prepared in a similar fashion as described in Example 1, step 8 using methyl 2-(((4aR,6R,7R,8S,8aR)-8-azido-6-((3,4-dichlorophenyl)thio)-2-phenyl-hexahydropyrano[3,2-d][1,3]dioxin-7-yl)oxy)propanoate (0.1 g, 0.185 mmol) and 5-ethynyl-1,2,3-trifluorobenzene (57.8 mg, 0.370 mmol) to afford methyl 2-(((4aR,6R,7R,8S, 8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)propanoate (0.12 g, 0.172 mmol) as diastereomeric mixture. The diastereomeric mixture was further purified by prep-HPLC Method I to afford methyl 2-(((4aR,6R,7R,8S,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)propanoate (40 mg, 0.057 mmol, 31%, isomer-1) and methyl 2-(((4aR,6R,7R,8S,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)propanoate (30 mg, 0.043 mmol, 23%, isomer-2).

Isomer-1:
LC-MS, [M+H]+=697.2, {Method C: tR=1.45 min}.

Isomer-2:
LC-MS, [M+H]+=697.2, {Method C: tR=3.398 min}

Step 3: Synthesis of 2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)propanoic acid (isomer-1): methyl 2-(((4aR,6R,7R,8S,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)propanoate (30 mg, 0.043 mmol, isomer-1) and heated at 70° C. for 16 h. Then the water was removed under reduced pressure and crude was purified by prep-HPLC Method A to afford Example 38 (isomer-1) 2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)propanoic acid (17 mg, 0.029 mmol, 66%). LC-MS, [M+H]$^+$=594.1, {Method A: $t_R$=1.271 min}. $^1$H NMR (400 MHz, METHANOL-d4) δ 8.70 (s, 1H), 7.83 (d, J=2.0 Hz, 1H), 7.69 (dd, J=8.8, 6.6 Hz, 2H), 7.62-7.52 (m, 1H), 7.49 (d, J=8.6 Hz, 1H), 6.20 (d, J=5.1 Hz, 1H), 5.07 (dd, J=11.2, 2.9 Hz, 1H), 4.84-4.79 (m, 1H), 4.51 (t, J=6.2 Hz, 1H), 4.23 (d, J=1.7 Hz, 1H), 3.92 (q, J=6.7 Hz, 1H), 3.80-3.62 (m, 2H), 1.11-0.99 (m, 3H). hGal3 IC$_{50}$=0.15 uM.

Example 38 (Isomer-2)

Prepared in a similar fashion as described above using 2-(((4aR,6R,7R,8S,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)propanoic acid (30 mg, 0.044 mmol, isomer-2) as the reactant and the crude was purified by prep-HPLC Method A to afford Example 38 (isomer-2) 2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)propanoic acid (8.7 mg, 0.015 mmol, 33%). LC-MS, [M+H]$^+$=594.1, {Method A: $t_R$=1.328 min. 1H NMR (400 MHz, METHANOL-d4) δ 8.93 (s, 1H), 7.85 (d, J=2.0 Hz, 1H), 7.64 (dd, J=8.8, 6.6 Hz, 2H), 7.58 (dd, J=8.4, 2.1 Hz, 1H), 7.51 (d, J=8.3 Hz, 1H), 6.25 (d, J=4.9 Hz, 1H), 5.07 (dd, J=11.2, 2.7 Hz, 1H), 5.03-4.98 (m, 1H), 4.49 (t, J=5.9 Hz, 1H), 4.38 (q, J=6.8 Hz, 1H), 4.28 (d, J=2.0 Hz, 1H), 3.70 (qd, J=11.4, 6.2 Hz, 2H), 1.37 (d, J=6.8 Hz, 3H). hGal3 IC$_{50}$=0.04 uM.

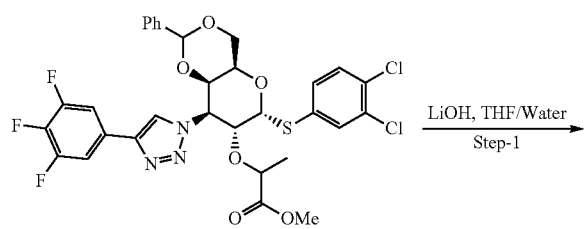

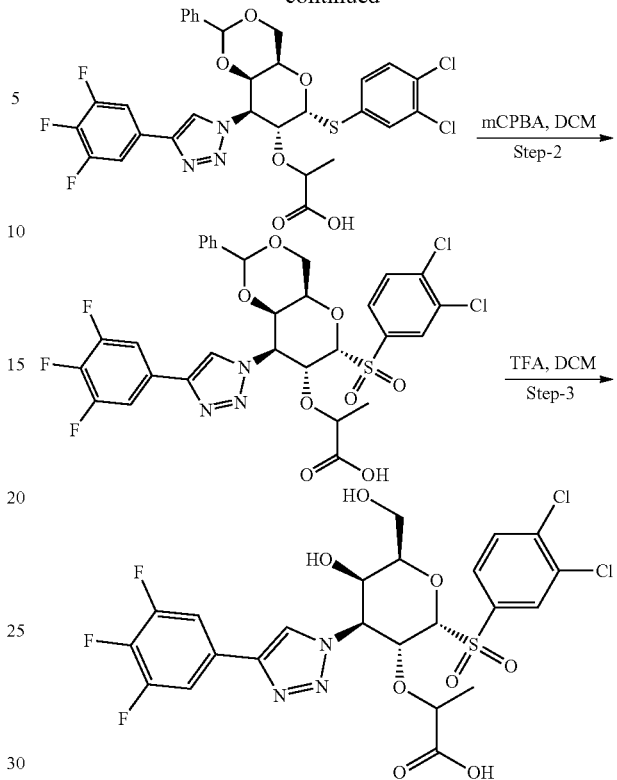

Example 39 (Isomer-1)

Preparation of 2-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)propanoic acid

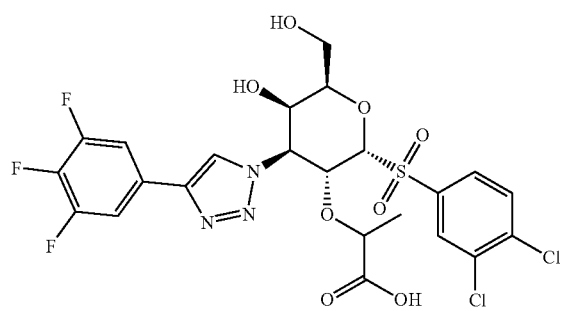 [SMILES: CC(O[C@@H]1[C@@H](n2cc(-c3cc(F)c(F)c(F)c3)nn2)[C@@H](O)[C@@H](CO)O[C@@H]1S(=O)(=O)c1ccc(Cl)c(Cl)c1)C(=O)O]

Step 1: Synthesis of 2-(((4aR,6R,7R,8S,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)propanoic acid: Prepared in a similar fashion as described in Example 20, step 1 using methyl 2-(((4aR,6R,7R,8S,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)propanoate (450 mg, 0.646 mmol, isomer-1) as the reactant to afford 2-(((4aR,6R,7R,8S,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)propanoic acid (380 mg, 0.557 mmol, 86%, isomer-1); LC-MS, [M+H]$^+$=682.3, {Method E: $t_R$=1.60 min}.

Step 2: Synthesis of 2-(((4aR,6R,7R,8S,8aR)-6-((3,4-dichlorophenyl)sulfonyl)-2-phenyl-8-(4-(3,4,5-trifluorophenyl)-1H-1,2,3-triazol-1-yl)hexahydropyrano[3,2-d][1,3]dioxin-7-yl)oxy)propanoic acid: Prepared in a similar fashion as described in Example-2 & Example-3, step 1 using 2-(((4aR,6R,7R,8S,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)propanoic acid (30 mg, 0.044 mmol, isomer-1) as the starting material to afford 2-(((4aR,6R,7R,8S,8aR)-6-((3,4-dichlorophenyl)sulfonyl)-2-phenyl-8-(4-(3,4,5-trifluorophenyl)-1H-1,2,3-triazol-1-yl)hexahydropyrano[3,2-d][1,3]dioxin-7-yl)oxy)propanoic acid (30 mg, 0.042 mmol, 96% isomer-1) which was as such taken for the next step without further purification LC-MS, [M+H]$^+$=714.1, {Method E: $t_R$=1.52 min}.

Step 3: Synthesis of 2-(((2R,3R,4S,5R,6R)-2-((3,4-dichlorophenyl)sulfonyl)-5-hydroxy-6-(hydroxymethyl)-4-(4-(3,4,5-trifluorophenyl)-1H-1,2,3-triazol-1-yl)tetrahydro-2H-pyran-3-yl)oxy)propanoic acid: Prepared in a similar fashion as described in Example-1, step 9 using 2-(((4aR,6R,7R,8S,8aR)-6-((3,4-dichlorophenyl)sulfonyl)-2-phenyl-8-(4-(3,4,5-trifluorophenyl)-1H-1,2,3-triazol-1-yl)hexahydropyrano[3,2-d][1,3]dioxin-7-yl)oxy)propanoic acid (30 mg, 0.042 mmol, isomer-1) as the starting material and purified by prep-HPLC Method A to afford Example 39 (isomer-1) 2-(((2R,3R,4S,5R,6R)-2-((3,4-dichlorophenyl)sulfonyl)-5-hydroxy-6-(hydroxymethyl)-4-(4-(3,4,5-trifluorophenyl)-1H-1,2,3-triazol-1-yl)tetrahydro-2H-pyran-3-yl)oxy)propanoic acid (7.1 mg, 0.011 mmol, 27%, isomer-1). LC-MS, [M+H]$^+$=626.1, {Method B: $t_R$=1.787 min}. 1H NMR (400 MHz, METHANOL-$d_4$) δ 8.65 (s, 1H), 8.00 (d, J=2.2 Hz, 1H), 7.77 (dd, J=8.4, 2.1 Hz, 1H), 7.64 (d, J=8.3 Hz, 1H), 7.62-7.49 (m, 2H), 5.84-5.71 (m, 2H), 4.83 (br. s., 1H), 4.44 (t, J=6.0 Hz, 1H), 4.19 (d, J=2.0 Hz, 1H), 3.70-3.55 (m, 2H), 3.43-3.34 (m, 1H), 0.80-0.69 (m, 3H). hGal3 IC$_{50}$=0.36 uM.

Example 39 (Isomer-2)

Prepared in a similar fashion as described for isomer-1 using isomer-2 as the starting material to afford Example 39 (isomer-2) 2-(((2R,3R,4S,5R,6R)-2-((3,4-dichlorophenyl)sulfonyl)-5-hydroxy-6-(hydroxymethyl)-4-(4-(3,4,5-trifluorophenyl)-1H-1,2,3-triazol-1-yl)tetrahydro-2H-pyran-3-yl)oxy)propanoic acid (10.8 mg, 0.017 mmol, 41%). LC-MS, [M+H]$^+$=626.1, {Method B: $t_R$=1.621 min}. 1H NMR (400 MHz, METHANOL-d4) δ 8.83 (s, 1H), 8.23 (d, J=2.0 Hz, 1H), 7.98 (dd, J=8.3, 2.2 Hz, 1H), 7.84 (d, J=8.3 Hz, 1H), 7.63 (dd, J=8.7, 6.7 Hz, 2H), 5.87 (dd, J=11.6, 2.6 Hz, 1H), 5.81 (d, J=6.1 Hz, 1H), 5.21 (dd, J=11.4, 6.0 Hz, 1H), 4.63-4.54 (m, 2H), 4.29 (s, 1H), 3.57 (dd, J=11.5, 5.1 Hz, 1H), 3.46 (dd, J=11.7, 6.6 Hz, 1H), 1.39-1.27 (m, 3H). hGal3 IC$_{50}$=0.02 uM.

General Synthetic Scheme:

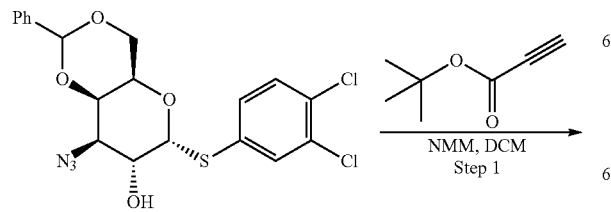

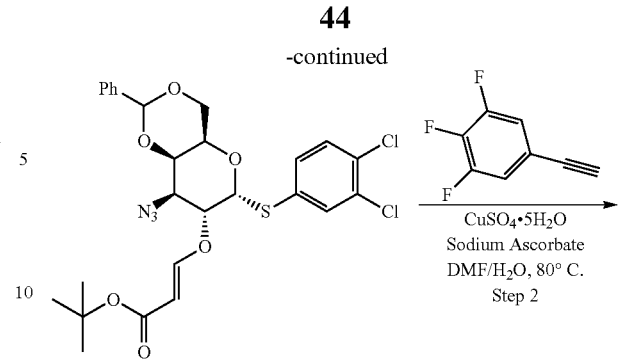

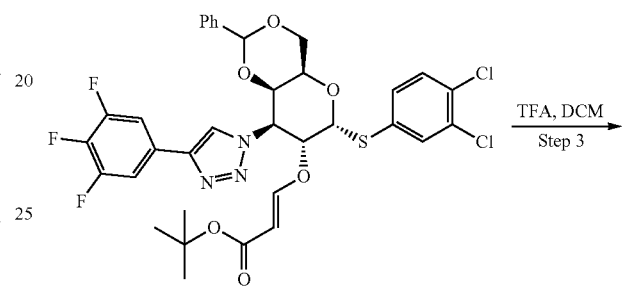

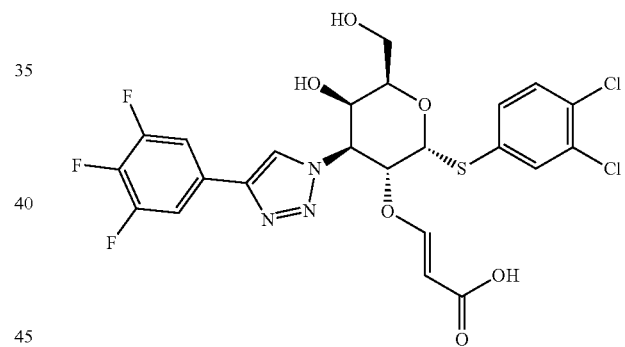

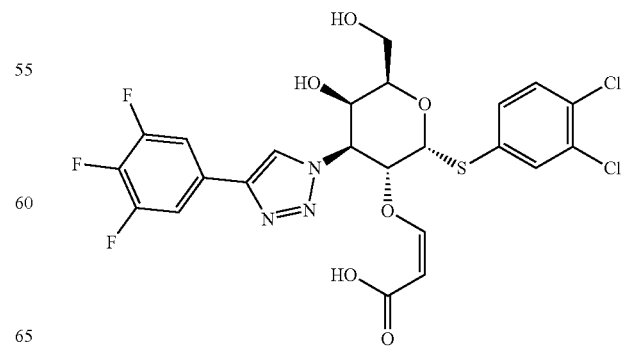

Example 40: Preparation of (E)-3-(((2R,3R,4S,5R, 6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)acrylic acid and (Z)-3-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)acrylic acid

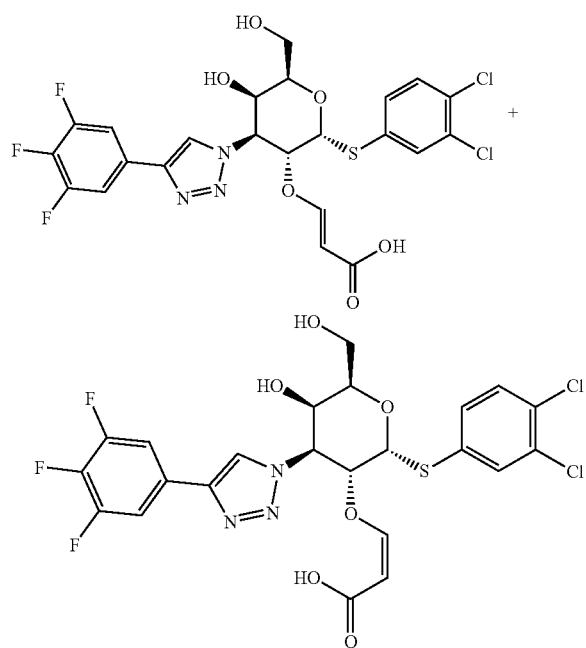

Step 1: Synthesis of tert-butyl (E)-3-(((4aR,6R,7R,8S, 8aR)-8-azido-6-((3,4-dichlorophenyl)thio)-2-phenylhexahydropyrano[3,2-d][1,3]dioxin-7-yl)oxy)acrylate: To a stirred solution of (4aR,6R,7R,8R,8aR)-8-azido-6-((3,4-dichlorophenyl)thio)-2-phenylhexahydropyrano[3,2-d][1,3]dioxin-7-ol (150 mg, 0.330 mmol) in DCM (4 mL), N-methylmorpholine (0.073 mL, 0.660 mmol) and tert-butyl propiolate (125 mg, 0.990 mmol) were added sequentially at rt under Argon and stirred for 4 h. The solvent was removed under reduced pressure and the crude residue was purified via chromatography in silica gel (0-20% EtOAc in Hexane) to afford tert-butyl (E)-3-(((4aR,6R,7R,8S,8aR)-8-azido-6-((3,4-dichlorophenyl)thio)-2-phenylhexahydropyrano[3,2-d][1,3]dioxin-7-yl)oxy)acrylate (130 mg, 0.224 mmol, 67.8% yield) [mixture of cis and trans, major trans]. LC-MS, [M+1]+=524.3, {Method E: $t_R$: 1.59 min (major) and 1.40 min (minor)}.

Step 2: Synthesis of tert-butyl (E)-3-(((4aR,6R,7R,8S, 8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)acrylate: Prepared in a similar fashion as described in Example-1, step-8 using tert-butyl (E)-3-(((4aR,6R,7R,8S,8aR)-8-azido-6-((3,4-dichlorophenyl)thio)-2-phenylhexahydropyrano[3,2-d][1,3]dioxin-7-yl)oxy)acrylate (50 mg, 0.086 mmol) 5-ethynyl-1,2,3-trifluorobenzene (0.013 mL, 0.112 mmol) as the reactants to afford tert-butyl (E)-3-(((4aR,6R,7R,8S,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)acrylate [mixture of cis and trans, major trans isomer] which was as such taken for the next step without further purification. LC-MS [M−56]+=680.4, {Method E: $t_R$=1.85 (major) and 1.64 (minor) min}.

Step 3: Synthesis of (E)-3-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)acrylic acid and (Z)-3-(((2R,3R,4S,5R, 6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)acrylic acid: Prepared in a similar fashion as described in Example-1, step-9 using tert-butyl (E)-3-(((4aR,6R,7R,8S,8aR)-6-((3,4-dichlorophenyl)thio)-2-phenyl-8-(4-(3,4,5-trifluorophenyl)-1H-1,2,3-triazol-1-yl)hexahydropyrano[3,2-d][1,3]dioxin-7-yl)oxy)acrylate (55 mg, 0.075 mmol) as the reactant and the crude was purified by prep-HPLC Method H to afford Example 40 (trans-isomer) (E)-3-(((2R,3R,4S,5R,6R)-2-((3, 4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)acrylic acid (13 mg, 27% yield). LC-MS, [M+H]+=592.1, {Method A: $t_R$=1.262 min}. 1H NMR (400 MHz, METHANOL-d4) δ 8.68 (s, 1H), 7.82 (d, J=2.0 Hz, 1H), 7.66 (dd, J=8.9, 6.5 Hz, 2H), 7.58-7.42 (m, 3H), 6.11 (d, J=5.4 Hz, 1H), 5.43 (dd, J=11.5, 5.4 Hz, 1H), 5.31-5.19 (m, 2H), 4.55 (t, J=6.4 Hz, 1H), 4.28 (d, J=2.2 Hz, 1H), 3.75 (dd, J=6.1, 2.7 Hz, 2H); hGal3 IC$_{50}$=0.06 uM; Example 40 (cis-isomer) (Z)-3-(((2R,3R,4S,5R,6R)-2-((3,4-dichlorophenyl)thio)-5-hydroxy-6-(hydroxymethyl)-4-(4-(3,4,5-trifluorophenyl)-1H-1,2,3-triazol-1-yl)tetrahydro-2H-pyran-3-yl)oxy)acrylic acid (2 mg, 4% yield). LC-MS, [M+H]+=592.1. 1H NMR (400 MHz, METHANOL-d4) δ 8.64 (s, 1H), 7.83 (d, J=2.0 Hz, 1H), 7.65 (dd, J=9.0, 6.6 Hz, 2H), 7.58-7.53 (m, 1H), 7.50 (d, J=8.3 Hz, 1H), 6.79 (d, J=7.1 Hz, 1H), 6.08 (d, J=5.4 Hz, 1H), 5.43-5.34 (m, 1H), 5.30 (dd, J=11.2, 2.7 Hz, 1H), 4.83 (d, J=7.1 Hz, 1H), 4.54 (t, J=6.1 Hz, 1H), 4.33 (d, J=1.5 Hz, 1H), 3.82-3.68 (m, 2H). {Method A: $t_R$=1.246 min}; hGal3 IC$_{50}$=0.68 uM.

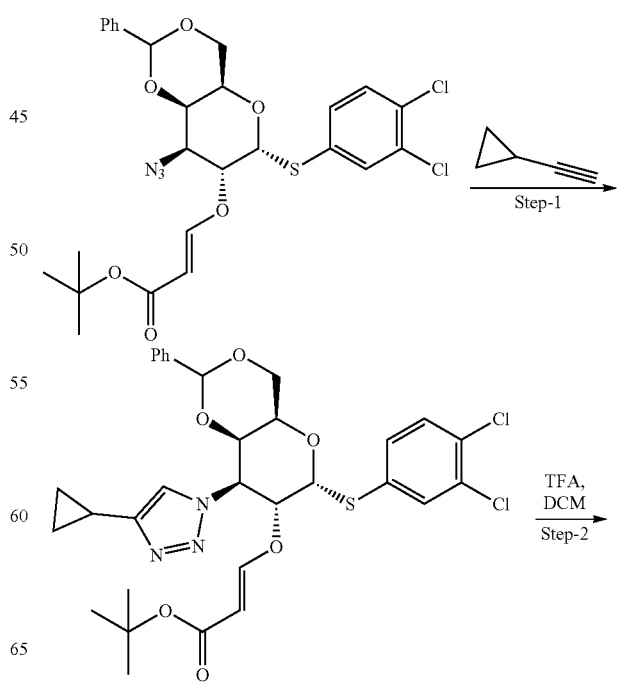

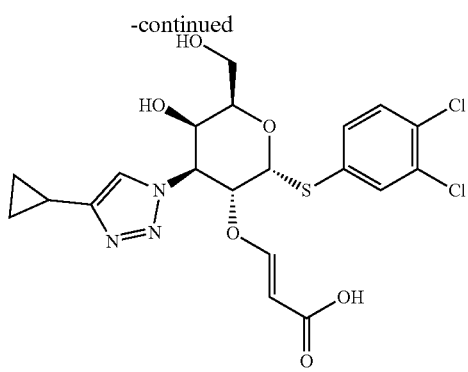

Example 41: Preparation of (E)-3-(((2R,3R,4S,5R, 6R)-4-(4-cyclopropyl-1H-1,2,3-triazol-1-yl)-2-((3,4-dichlorophenyl)thio)-5-hydroxy-6-(hydroxymethyl) tetrahydro-2H-pyran-3-yl)oxy)acrylic acid

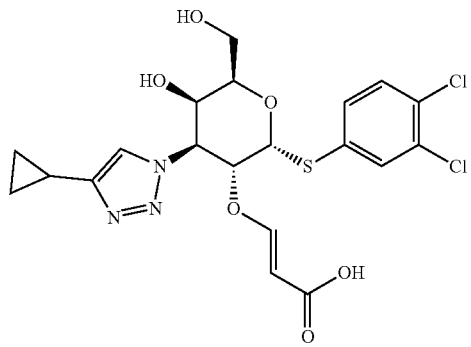 [SMILES: O=C(O)/C=C/O[C@@H]1[C@@H](n2cc(C3CC3)nn2)[C@@H](O)[C@@H](CO)O[C@@H]1Sc1ccc(Cl)c(Cl)c1]

Step 1: Synthesis of tert-butyl (E)-3-(((4aR,6R,7R,8S,8aR)-8-(4-cyclopropyl-1H-1,2,3-triazol-1-yl)-6-((3,4-dichlorophenyl)thio)-2-phenylhexahydropyrano[3,2-d][1,3]dioxin-7-yl)oxy)acrylate: To a stirred solution of tert-butyl (E)-3-(((4aR,6R,7R,8S,8aR)-8-azido-6-((3,4-dichlorophenyl)thio)-2-phenylhexahydropyrano[3,2-d][1,3]dioxin-7-yl)oxy)acrylate (50 mg, 0.086 mmol) in acetonitrile (3 mL), ethynylcyclopropane (in toluene) (0.102 mL, 0.861 mmol), copper(I) iodide (4.10 mg, 0.022 mmol) and DIPEA (0.045 mL, 0.258 mmol) were added sequentially at rt and heated at 80° C. for 14 h. Then reaction mixture was allowed to reach rt, solvent was removed under reduced pressure and the crude residue was purified via chromatography in silica gel (25-35% EtOAc in Hexane) to afford tert-butyl (E)-3-(((4aR,6R,7R,8S,8aR)-8-(4-cyclopropyl-1H-1,2,3-triazol-1-yl)-6-((3,4-dichlorophenyl)thio)-2-phenylhexahydropyrano[3,2-d][1,3]dioxin-7-yl)oxy)acrylate (30 mg, 0.046 mmol, 54%) as an off-white solid. LC-MS, [M+H]$^+$=647.3, {Method E: $t_R$=1.39 min}. $^1$H NMR (400 MHz, CHLOROFORM-d) δ 7.59 (d, J=2.0 Hz, 1H), 7.43-7.38 (m, 7H), 7.33-7.28 (m, 1H), 7.14-7.11 (m, 1H), 6.01 (d, J=5.3 Hz, 1H), 5.53 (s, 1H), 5.38 (dd, J=11.5, 3.3 Hz, 1H), 5.25 (d, J=12.3 Hz, 1H), 5.02 (dd, J=11.3, 5.3 Hz, 1H), 4.50 (d, J=2.5 Hz, 1H), 4.34 (s, 1H), 4.33-4.28 (m, 1H), 4.15 (dd, J=12.8, 1.5 Hz, 1H), 1.98-1.90 (m, 1H), 1.43 (s, 9H), 1.00-0.92 (m, 2H), 0.90-0.79 (m, 2H)

Step 2: Synthesis of (E)-3-(((2R,3R,4S,5R,6R)-4-(4-cyclopropyl-1H-1,2,3-triazol-1-yl)-2-((3,4-dichlorophenyl)thio)-5-hydroxy-6-(hydroxymethyl)tetrahydro-2H-pyran-3-yl)oxy)acrylic acid: Prepared in a similar fashion as described in Example-1, step-9 using tert-butyl (E)-3-(((4aR,6R,7R,8S,8aR)-8-(4-cyclopropyl-1H-1,2,3-triazol-1-yl)-6-((3,4-dichlorophenyl)thio)-2-phenylhexahydropyrano[3,2-d][1,3]dioxin-7-yl)oxy)acrylate (30 mg, 0.046 mmol) as the reactant and the crude material was purified by Method H to afford Example 41 (E)-3-(((2R,3R,4S,5R,6R)-4-(4-cyclopropyl-1H-1,2,3-triazol-1-yl)-2-((3,4-dichlorophenyl)thio)-5-hydroxy-6-(hydroxymethyl)tetrahydro-2H-pyran-3-yl)oxy)acrylic acid (7.4 mg, 31%). LC-MS, [M+H]$^+$=502.1, {Method A: $t_R$=0.984 min}. 1H NMR (400 MHz, METHANOL-d4) δ 7.94 (s, 1H), 7.81 (d, J=2.0 Hz, 1H), 7.58-7.48 (m, 2H), 7.44 (d, J=12.2 Hz, 1H), 6.06 (d, J=5.6 Hz, 1H), 5.34 (dd, J=11.4, 5.5 Hz, 1H), 5.24 (d, J=12.2 Hz, 1H), 5.11 (dd, J=11.4, 2.8 Hz, 1H), 4.50 (t, J=5.7 Hz, 1H), 4.21 (d, J=2.7 Hz, 1H), 3.73 (dd, J=6.1, 2.7 Hz, 2H), 2.05-1.93 (m, 1H), 1.01-0.94 (m, 2H), 0.80 (ddd, J=7.2, 4.8, 2.0 Hz, 2H). hGal3 IC$_{50}$=2.74 uM.

General Synthetic Scheme:

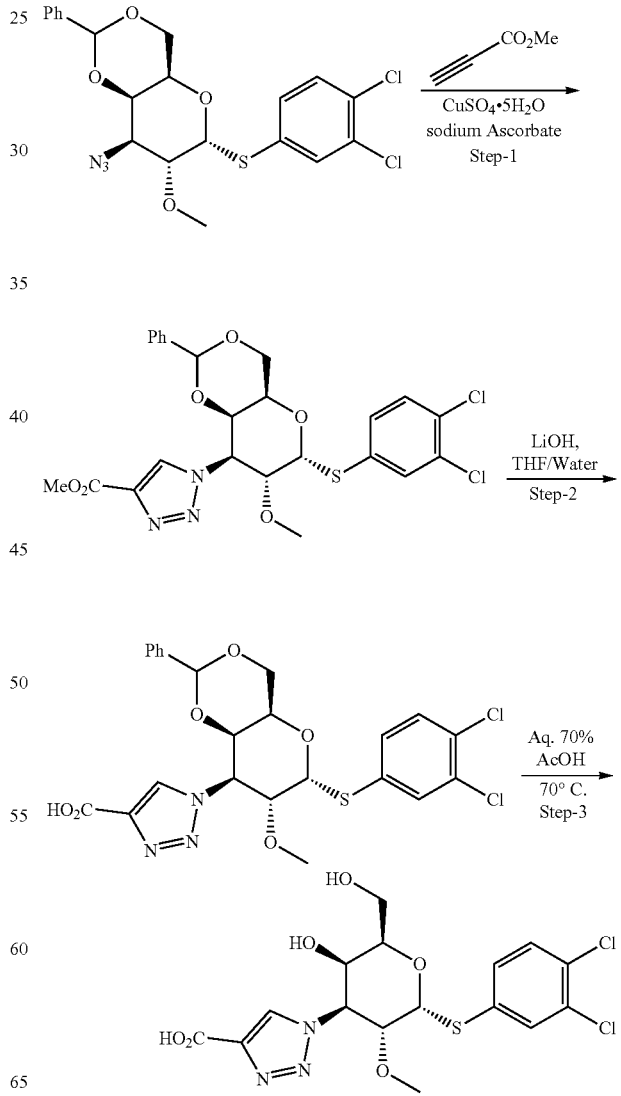

Example 42: Preparation of 1-((2R,3R,4S,5R,6R)-2-((3,4-dichlorophenyl)thio)-5-hydroxy-6-(hydroxymethyl)-3-methoxytetrahydro-2H-pyran-4-yl)-1H-1,2,3-triazole-4-carboxylic acid

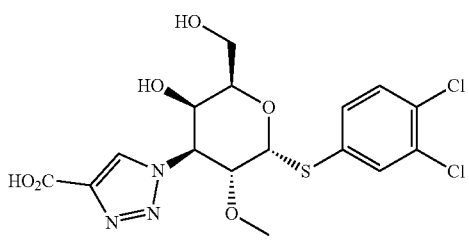 [SMILES: CO[C@@H]1[C@@H](n2cc(C(=O)O)nn2)[C@@H](O)[C@@H](CO)O[C@@H]1Sc1ccc(Cl)c(Cl)c1]

Step 1: Synthesis of methyl 1-((4aR,6R,7R,8S,8aR)-6-((3,4-dichlorophenyl)thio)-7-methoxy-2-phenylhexahydropyrano[3,2-d][1,3]dioxin-8-yl)-1H-1,2,3-triazole-4-carboxylate: Prepared in a similar fashion as described in Example 1, Step-8 using (4aR,6R,7R,8S,8aR)-8-azido-6-((3,4-dichlorophenyl)thio)-7-methoxy-2-phenylhexahydropyrano[3,2-d][1,3]dioxine (50 mg, 0.107 mmol) and methyl propiolate (26.9 mg, 0.320 mmol) as the reactants to afford methyl 1-((4aR,6R,7R,8S,8aR)-6-((3,4-dichlorophenyl)thio)-7-methoxy-2-phenylhexahydropyrano[3,2-d][1,3]dioxin-8-yl)-1H-1,2,3-triazole-4-carboxylate (60 mg, 0.100 mmol, 94%) as an off-white solid. LC-MS, [M+H]+=552.3, {Method E: $t_R$=1.98 min}.

Step 2: Synthesis of 1-((4aR,6R,7R,8S,8aR)-6-((3,4-dichlorophenyl)thio)-7-methoxy-2-phenylhexahydropyrano[3,2-d][1,3]dioxin-8-yl)-1H-1,2,3-triazole-4-carboxylic acid: Prepared in a similar fashion as described in Example 20, step 1 using methyl 1-((4aR,6R,7R,8S,8aR)-6-((3,4-dichlorophenyl)thio)-7-methoxy-2-phenylhexahydropyrano[3,2-d][1,3]dioxin-8-yl)-1H-1,2,3-triazole-4-carboxylate as the starting material to afford 1-((4aR,6R,7R,8S,8aR)-6-((3,4-dichlorophenyl)thio)-7-methoxy-2-phenylhexahydropyrano[3,2-d][1,3]dioxin-8-yl)-1H-1,2,3-triazole-4-carboxylic acid (140 mg, 0.226 mmol, 78%) as a white solid. LC-MS, [M+H]+=477, {Method E: $t_R$=1.34 min}.

Step 3: Synthesis of 1-((2R,3R,4S,5R,6R)-2-((3,4-dichlorophenyl)thio)-5-hydroxy-6-(hydroxymethyl)-3-methoxytetrahydro-2H-pyran-4-yl)-1H-1,2,3-triazole-4-carboxylic acid: Prepared in a similar fashion as described in Example 4, step 4 using To1-((4aR,6R,7R,8S,8aR)-6-((3,4-dichlorophenyl)thio)-7-methoxy-2-phenylhexahydropyrano[3,2-d][1,3]dioxin-8-yl)-1H-1,2,3-triazole-4-carboxylic acid (40 mg, 0.074 mmol) as the starting material. The crude material was purified via prep-HPLC Method A to afford Example 42 1-((2R,3R,4S,5R,6R)-2-((3,4-dichlorophenyl)thio)-5-hydroxy-6-(hydroxymethyl)-3-methoxytetrahydro-2H-pyran-4-yl)-1H-1,2,3-triazole-4-carboxylic acid (11.5 mg, 0.026 mmol, 34%) LC-MS, [M+H]+=450.0, {Method A: $t_R$=1.01 min}. 1H NMR (400 MHz, METHANOL-$d_4$) δ 8.62 (s, 1H), 7.83 (d, J=2.0 Hz, 1H), 7.56 (dd, J=8.4, 2.1 Hz, 1H), 7.50 (d, J=8.6 Hz, 1H), 6.18 (d, J=5.4 Hz, 1H), 5.05 (dd, J=11.2, 2.9 Hz, 1H), 4.61 (dd, J=11.5, 5.4 Hz, 1H), 4.47 (t, J=6.4 Hz, 1H), 4.18 (d, J=2.7 Hz, 1H), 3.77-3.64 (m, 2H), 3.40 (s, 3H). hGal3 $IC_{50}$=5 uM.

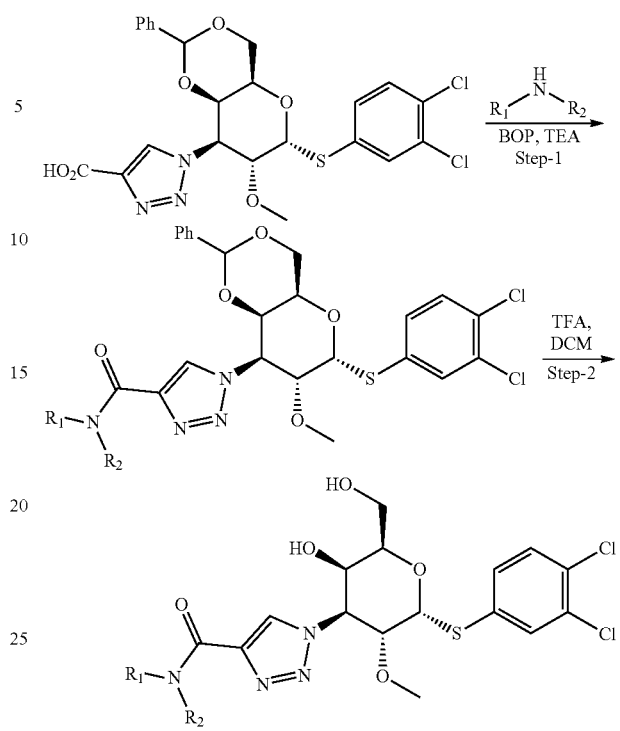

Example 43: Preparation of N-cyclopropyl-1-((2R,3R,4S,5R,6R)-2-((3,4-dichlorophenyl)thio)-5-hydroxy-6-(hydroxymethyl)-3-methoxytetrahydro-2H-pyran-4-yl)-1H-1,2,3-triazole-4-carboxamide.

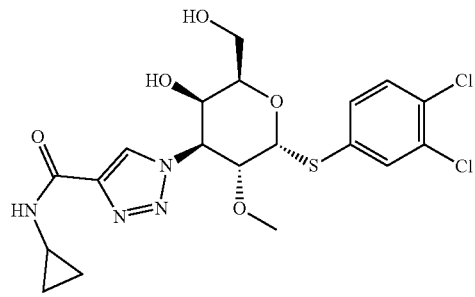 [SMILES: CO[C@@H]1[C@@H](n2cc(C(=O)NC3CC3)nn2)[C@@H](O)[C@@H](CO)O[C@@H]1Sc1ccc(Cl)c(Cl)c1]

Step 1: Synthesis of N-cyclopropyl-1-((4aR,6R,7R,8S,8aR)-6-((3,4-dichlorophenyl)thio)-7-methoxy-2-phenylhexahydropyrano[3,2-d][1,3]dioxin-8-yl)-1H-1,2,3-triazole-4-carboxamide: To a stirred solution of 1-((4aR,6R,7R,8S,8aR)-6-((3,4-dichlorophenyl)thio)-7-methoxy-2-phenylhexahydropyrano[3,2-d][1,3]dioxin-8-yl)-1H-1,2,3-triazole-4-carboxylic acid (55 mg, 0.102 mmol) in DMF (2 mL), triethylamine (0.028 mL, 0.204 mmol), BOP (67.8 mg, 0.153 mmol) and cyclopropanamine (17.50 mg, 0.306 mmol) were added sequentially at rt and stirred for 3 hours. Then reaction mixture was diluted with ice-cold water (10 mL) and stirred 10 min. The resultant solid was filtered and dried under vacuum to get N-cyclopropyl-1-((4aR,6R,7R,8S,8aR)-6-((3,4-dichlorophenyl)thio)-7-methoxy-2-phenylhexahydropyrano[3,2-d][1,3]dioxin-8-yl)-1H-1,2,3-triazole-4-carboxamide (45 mg, 0.070 mmol, 69%) as an off-white solid. LC-MS, [M+H]+=577.1, {Method E: $t_R$=2.05 min}.

Step 2: Synthesis of N-cyclopropyl-1-((2R,3R,4S,5R,6R)-2-((3,4-dichlorophenyl)thio)-5-hydroxy-6-(hydroxymethyl)-3-methoxytetrahydro-2H-pyran-4-yl)-1H-1,2,3-triazole-4-carboxamide: Prepared in a similar fashion as described in Example 1, step 9 using N-cyclopropyl-1-((4aR,6R,7R,8S,8aR)-6-((3,4-dichlorophenyl)thio)-7-methoxy-2-phenylhexahydropyrano[3,2-d][1,3]dioxin-8-yl)-1H-1,2,3-triazole-4-carboxamide (50 mg, 0.087 mmol) as the reactant and the crude material was purified via prep-HPLC Method A to afford Example 43 N-cyclopropyl-1-((2R,3R,4S,5R,6R)-2-((3,4-dichlorophenyl)thio)-5-hydroxy-6-(hydroxymethyl)-3-methoxytetrahydro-2H-pyran-4-yl)-1H-1,2,3-triazole-4-carboxamide (22.4 mg, 0.046 mmol, 53%). LC-MS, [M+H]$^+$=489.1, {Method A: $t_R$=1.56 min}. 1H NMR (400 MHz, METHANOL-d$_4$) δ 8.52 (s, 1H), 7.83 (d, J=2.0 Hz, 1H), 7.56 (dd, J=8.4, 2.1 Hz, 1H), 7.50 (d, J=8.3 Hz, 1H), 6.17 (d, J=5.4 Hz, 1H), 5.03 (dd, J=11.5, 2.9 Hz, 1H), 4.57 (dd, J=11.4, 5.3 Hz, 1H), 4.46 (t, J=6.4 Hz, 1H), 4.17 (d, J=2.0 Hz, 1H), 3.79-3.63 (m, 2H), 3.43 (s, 3H), 2.88 (tt, J=7.3, 3.7 Hz, 1H), 0.89-0.80 (m, 2H), 0.73-0.63 (m, 2H). hGal3 IC$_{50}$=2.90 uM.

Example 44: Preparation of N-cyclopropyl-1-((2R,3R,4S,5R,6R)-2-((3,4-dichlorophenyl)thio)-5-hydroxy-6-(hydroxymethyl)-3-methoxytetrahydro-2H-pyran-4-yl)-N-methyl-1H-1,2,3-triazole-4-carboxamide

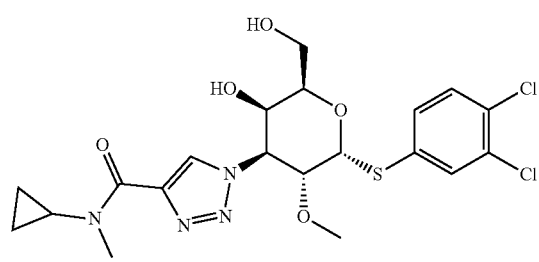 [SMILES: CO[C@@H]1[C@@H](n2cc(C(=O)N(C)C3CC3)nn2)[C@@H](O)[C@@H](CO)O[C@@H]1Sc1ccc(Cl)c(Cl)c1]

This was prepared in an analogous fashion to Example 43 [Step-1 and Step-2], substituting appropriate amine in the synthetic sequence to afford Example 44 N-cyclopropyl-1-((2R,3R,4S,5R,6R)-2-((3,4-dichlorophenyl)thio)-5-hydroxy-6-(hydroxymethyl)-3-methoxytetrahydro-2H-pyran-4-yl)-N-methyl-1H-1,2,3-triazole-4-carboxamide (17.9 mg, 0.035 mmol, 52%). LC-MS, [M+H]$^+$=503.1, {Method B: $t_R$=1.52 min}. $^1$H NMR (400 MHz, METHANOL-d4) δ ppm 8.50 (s, 1H), 7.83 (d, J=2.0 Hz, 1H), 7.44-7.63 (m, 2H), 6.18 (d, J=5.4 Hz, 1H), 5.05 (dd, J=11.4, 3.1 Hz, 1H), 4.56-4.65 (m, 1H), 4.42-4.51 (m, 1H), 4.18-4.24 (m, 1H), 3.63-3.79 (m, 2H), 3.39 (s, 3H), 3.08-3.27 (m, 4H), 0.83 (br s, 2H), 0.50-0.72 (m, 2H). hGal3 IC$_{50}$=5 uM.

Synthetic Scheme:

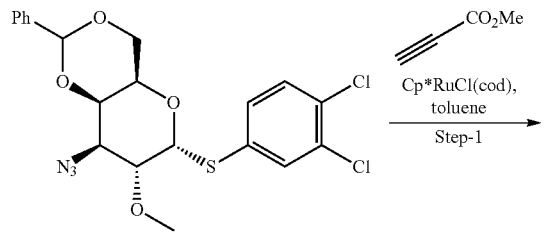

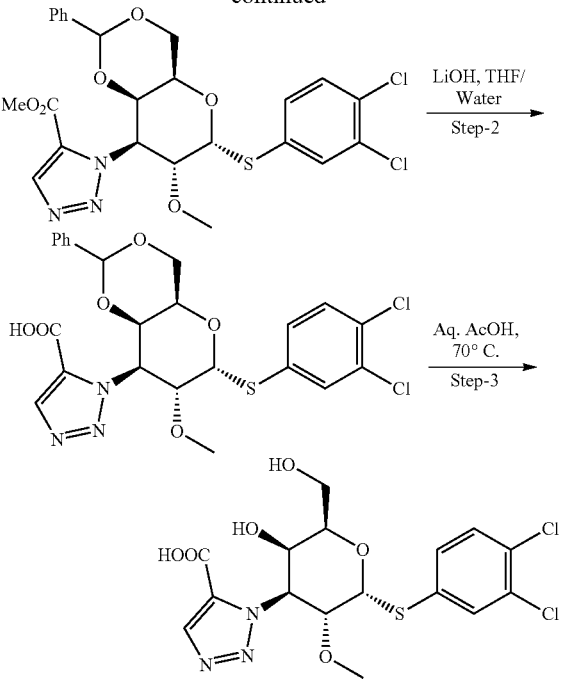

Example 45: Preparation of 1-((2R,3R,4S,5R,6R)-2-((3,4-dichlorophenyl)thio)-5-hydroxy-6-(hydroxymethyl)-3-methoxytetrahydro-2H-pyran-4-yl)-1H-1,2,3-triazole-5-carboxylic acid

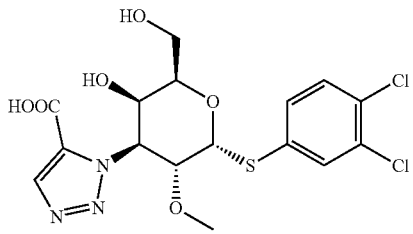 [SMILES: CO[C@@H]1[C@@H](n2nncc2C(=O)O)[C@@H](O)[C@@H](CO)O[C@@H]1Sc1ccc(Cl)c(Cl)c1]

Step 1: Synthesis of methyl 1-((4aR,6R,7R,8S,8aR)-6-((3,4-dichlorophenyl)thio)-7-methoxy-2-phenylhexahydropyrano[3,2-d][1,3]dioxin-8-yl)-1H-1,2,3-triazole-5-carboxylate: To a stirred solution of (4aR,6R,7R,8S,8aR)-8-azido-6-((3,4-dichlorophenyl)thio)-7-methoxy-2-phenylhexahydropyrano[3,2-d][1,3]dioxine (50 mg, 0.107 mmol) in toluene (4 mL), was added methyl propiolate (17.95 mg, 0.214 mmol) and the reaction mixture was degassed with argon for 5 min. Then chloro(1,5-cyclooctadiene)(pentamethylcyclopentadienyl)ruthenium (4.06 mg, 10.68 μmol) was added and heated at 100° C. for 1 hour under microwave. Solvent was removed under reduced pressure and crude residue was purified via chromatography in silica gel (2-5% MeOH in CHCl$_3$) to yield methyl 1-((4aR,6R,7R,8S,8aR)-6-((3,4-dichlorophenyl)thio)-7-methoxy-2-phenylhexahydropyrano[3,2-d][1,3]dioxin-8-yl)-1H-1,2,3-triazole-5-carboxylate (60 mg, 0.043 mmol, 41%) as brown gummy solid. LC-MS, [M+H]$^+$=552.2, {Method E: $t_R$=2.16 min}.

Step 2: Synthesis of 1-((4aR,6R,7R,8S,8aR)-6-((3,4-dichlorophenyl)thio)-7-methoxy-2-phenylhexahydropyrano

[3,2-d][1,3]dioxin-8-yl)-1H-1,2,3-triazole-5-carboxylic acid: Prepared in a similar fashion as described in Example 20, step 1 using methyl 1-((4aR,6R,7R,8S,8aR)-6-((3,4-dichlorophenyl)thio)-7-methoxy-2-phenylhexahydropyrano [3,2-d][1,3]dioxin-8-yl)-1H-1,2,3-triazole-5-carboxylate (60 mg, 0.109 mmol) as the reactant to afford 1-((4aR,6R, 7R,8S,8aR)-6-((3,4-dichlorophenyl)thio)-7-methoxy-2-phenylhexahydropyrano[3,2-d][1,3]dioxin-8-yl)-1H-1,2,3-triazole-5-carboxylic acid (40 mg, 0.047 mmol, 43%) as white solid. LC-MS, [M–H]$^+$=536.1, {Method E: $t_R$=1.35 min}.

Step 3: Synthesis of 1-((2R,3R,4S,5R,6R)-2-((3,4-dichlorophenyl)thio)-5-hydroxy-6-(hydroxymethyl)-3-methoxytetrahydro-2H-pyran-4-yl)-1H-1,2,3-triazole-5-carboxylic acid: Prepared in a similar fashion as described in Example 4, step 4 using 1-((4aR,6R,7R,8S,8aR)-6-((3,4-dichlorophenyl)thio)-7-methoxy-2-phenylhexahydropyrano [3,2-d][1,3]dioxin-8-yl)-1H-1,2,3-triazole-5-carboxylic acid (40 mg, 0.074 mmol) as the starting material. The crude material was purified via prep-HPLC Method A to afford Example 45 1-((2R,3R,4S,5R,6R)-2-((3,4-dichlorophenyl)thio)-5-hydroxy-6-(hydroxymethyl)-3-methoxytetrahydro-2H-pyran-4-yl)-1H-1,2,3-triazole-5-carboxylic acid (3.3 mg, 7.33 μmol, 10%). LC-MS, [M+H]$^+$=450.0, {Method A: $t_R$=1.01 min}. 1H NMR (400 MHz, METHANOL-d4) δ 8.13 (s, 1H), 7.82 (d, J=2.0 Hz, 1H), 7.55 (dd, J=8.4, 2.1 Hz, 1H), 7.49 (d, J=8.3 Hz, 1H), 6.19 (d, J=5.4 Hz, 1H), 5.77 (dd, J=11.4, 2.8 Hz, 1H), 5.00 (dd, J=11.1, 5.3 Hz, 1H), 4.48 (t, J=6.1 Hz, 1H), 4.28 (s, 1H), 3.75-3.64 (m, 2H), 3.34 (s, 3H). hGal3 IC$_{50}$=1.52 uM.

General Synthetic Scheme:

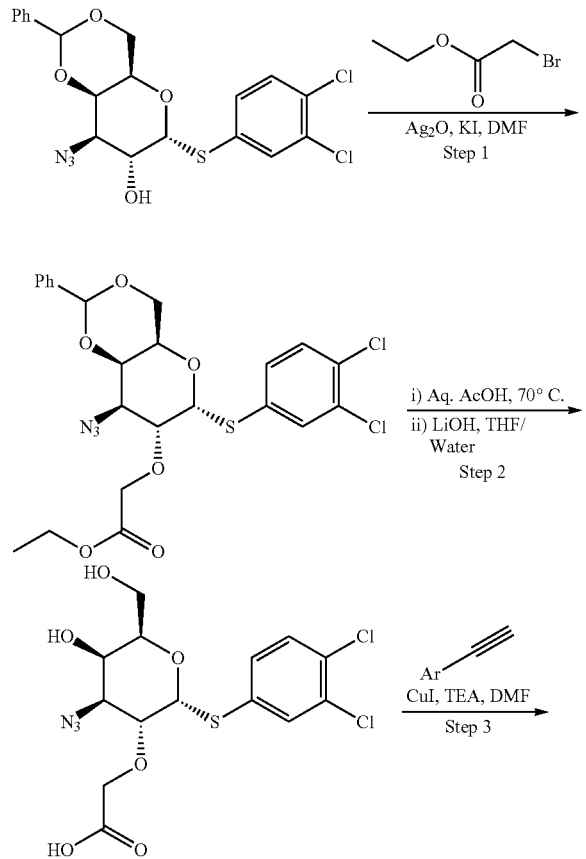

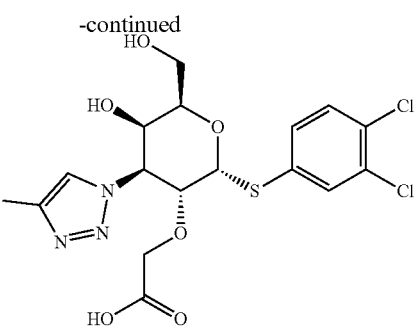

Example 46: Preparation of 2-(((2R,3R,4S,5R,6R)-2-((3,4-dichlorophenyl)thio)-5-hydroxy-6-(hydroxymethyl)-4-(4-phenyl-1H-1,2,3-triazol-1-yl) tetrahydro-2H-pyran-3-yl)oxy)acetic acid

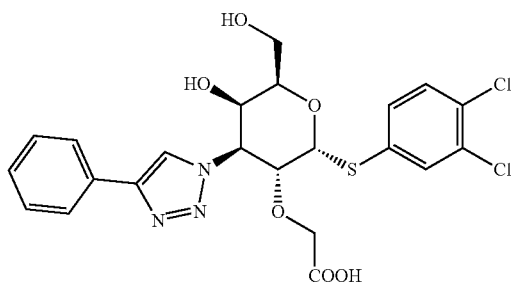 [SMILES: O=C(O)CO[C@@H]1[C@@H](n2cc(-c3ccccc3)nn2)[C@@H](O)[C@@H](CO)O[C@@H]1Sc1ccc(Cl)c(Cl)c1]

Step 1: Synthesis of ethyl 2-(((4aR,6R,7R,8S,8aR)-8-azido-6-((3,4-dichlorophenyl)thio)-2-phenylhexahydropyrano[3,2-d][1,3]dioxin-7-yl)oxy)acetate: Prepared in a similar fashion as described in Example 14, step 1 using (4aR, 6R,7R,8R,8aR)-8-azido-6-((3,4-dichlorophenyl)thio)-2-phenylhexahydropyrano[3,2-d][1,3]dioxin-7-ol (1 g, 2.201 mmol) and ethyl 2-bromoacetate (0.380 mL, 3.30 mmol) as the starting materials. The crude was purified purified via chromatography in silica gel (50-100% EtOAc in Hexane) to yield ethyl 2-(((4aR,6R,7R,8S,8aR)-8-azido-6-((3,4-dichlorophenyl)thio)-2-phenylhexahydropyrano[3,2-d][1,3]dioxin-7-yl)oxy)acetate (0.80 g, 1.462 mmol, 66%) as an off-white solid. LC-MS, [M+18]$^+$=558.3 {Method C: $t_R$=3.848 min}.

Step 2: Synthesis of 2-(((2R,3R,4S,5R,6R)-4-azido-2-((3, 4-dichlorophenyl)thio)-5-hydroxy-6-(hydroxymethyl)tetrahydro-2H-pyran-3-yl)oxy)acetic acid: ethyl 2-(((4aR,6R, 7R,8S,8aR)-8-azido-6-((3,4-dichlorophenyl)thio)-2-phenylhexahydropyrano[3,2-d][1,3]dioxin-7-yl)oxy)acetate (300 mg, 0.555 mmol) was suspended in Aq. 70% AcOH (100 mL, 1.747 mol) and heated at 80° C. for overnight. The solvent was removed under reduced pressure to give crude residue. The crude residue was dissolved in THF (10 mL) and water (3 mL), lithium hydroxide (66.5 mg, 2.78 mmol) was added and stirred for 1 h. The reaction mixture was acidified with aq. 1.5N HCl solution (pH 2-3) and extracted with 10% Methanol in DCM (3×20 mL). The combined organic extracts were washed with water, brine, dried over sodium sulphate to give crude residue. The crude residue was triturated with hexane to afford 2-(((2R,3R,4S,5R,6R)-4-azido-2-((3,4-dichlorophenyl)thio)-5-hydroxy-6-(hydroxymethyl)tetrahydro-2H-pyran-3-yl)oxy)acetic acid (160 mg, 0.38 mmol, 68%) as an off-white solid. LC-MS, [M−1]+=422.0 {Method E: $t_R$=1.00 min}.

Step 3: Synthesis of 2-(((2R,3R,4S,5R,6R)-2-((3,4-dichlorophenyl)thio)-5-hydroxy-6-(hydroxymethyl)-4-(4-phenyl-1H-1,2,3-triazol-1-yl)tetrahydro-2H-pyran-3-yl) oxy)acetic acid: To a solution of 2-(((2R,3R,4S,5R,6R)-4-azido-2-((3,4-dichlorophenyl)thio)-5-hydroxy-6-(hydroxymethyl)tetrahydro-2H-pyran-3 yl)oxy)acetic acid (10 mg, 0.024 mmol) in DMF (0.5 mL), copper(I) iodide (1.347 mg, 7.07 μmol), ethynylbenzene (7.08 mg, 0.059 mmol) and trimethylamine (0.016 mL, 0.118 mmol) were added sequentially at rt and heated at 85° C. for 2 h. Then the solvent was removed under reduced pressure and purified by prep-HPLC Method A to afford Example 46 2-(((2R,3R,4S,5R,6R)-2-((3,4-dichlorophenyl)thio)-5-hydroxy-6-(hydroxymethyl)-4-(4-phenyl-1H-1,2,3-triazol-1-yl)tetrahydro-2H-pyran-3-yl)oxy)acetic acid (3.5 mg, 0.008 mmol, 30%). LC-MS, [M+H]+=527.0, {Method A: $t_R$=0.952 min}. 1H NMR (400 MHz, METHANOL-d4) δ 9.00 (br. s., 1H), 7.91 (br. s., 2H), 7.85 (s, 1H), 7.59 (d, J=8.5 Hz, 1H), 7.54-7.41 (m, 3H), 7.41-7.31 (m, 1H), 6.28 (br. s., 1H), 5.13 (br. s., 2H), 4.52 (br. s., 1H), 4.32 (s, 1H), 3.94 (s, 1H), 3.80-3.66 (m, 3H), 2.17 (br. s., 1H). hGal3 IC$_{50}$=1.36 uM.

The Examples in the table below were prepared in an analogous fashion to Example 46 [Step-3], substituting appropriate alkyl halides in the synthetic sequence.

| Example | hGal3 IC$_{50}$ (uM) | Structure | LCMS RT | M + H | Method |
|---|---|---|---|---|---|
| 47 | 1.53 | 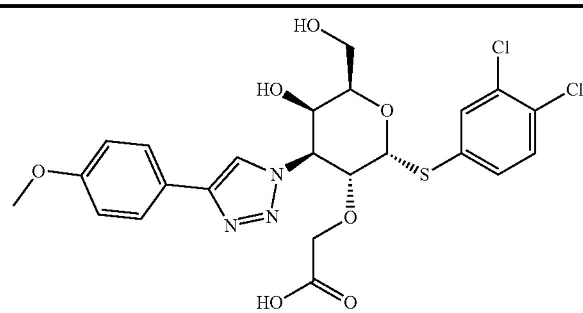 | 0.971 | 558.1 | A |
| 48 | 0.74 | 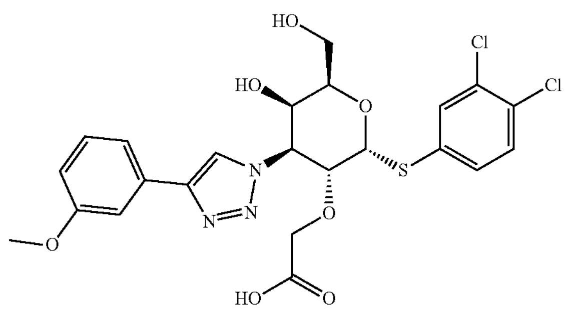 [SMILES: COc1cccc(-c2cn([C@H]3[C@@H](O)[C@@H](CO)O[C@H](Sc4ccc(Cl)c(Cl)c4)[C@@H]3OCC(=O)O)nn2)c1] | 0.991 | 558.1 | A |
| 49 | 1.34 | 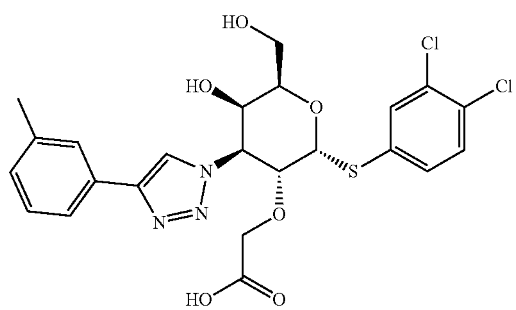 [SMILES: Cc1cccc(-c2cn([C@H]3[C@@H](O)[C@@H](CO)O[C@H](Sc4ccc(Cl)c(Cl)c4)[C@@H]3OCC(=O)O)nn2)c1] | 1.037 | 542 | A |
| 50 | 0.62 | 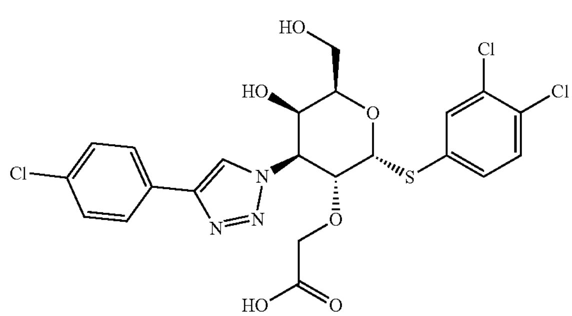 [SMILES: O=C(O)CO[C@@H]1[C@@H](n2cc(-c3ccc(Cl)cc3)nn2)[C@@H](O)[C@@H](CO)O[C@@H]1Sc1ccc(Cl)c(Cl)c1] | 1.084 | 562 | A |

-continued

| Example | hGal3 IC$_{50}$ (uM) | Structure | LCMS RT | M + H | Method |
|---|---|---|---|---|---|
| 51 | 1.61 | 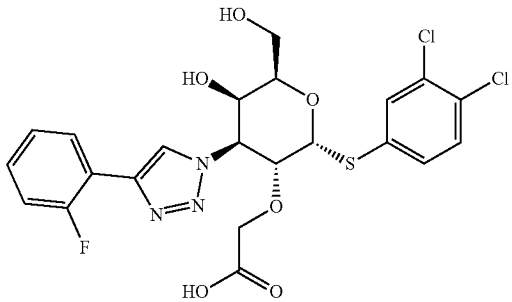 [SMILES: O=C(O)CO[C@@H]1[C@@H](n2cc(-c3ccccc3F)nn2)[C@@H](O)[C@@H](CO)O[C@@H]1Sc1ccc(Cl)c(Cl)c1] | 0.993 | 546 | A |
| 52 | 0.25 | 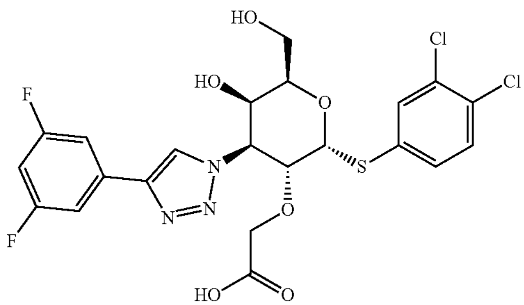 [SMILES: O=C(O)CO[C@@H]1[C@@H](n2cc(-c3cc(F)cc(F)c3)nn2)[C@@H](O)[C@@H](CO)O[C@@H]1Sc1ccc(Cl)c(Cl)c1] | 1.067 | 564 | A |
| 53 | 1.75 | 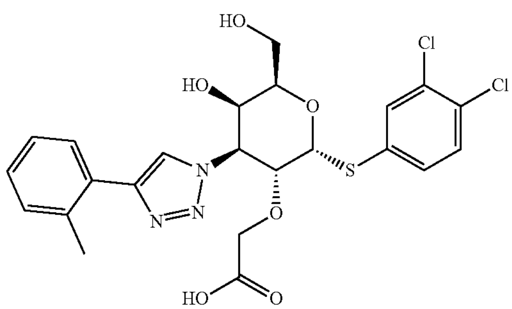 [SMILES: Cc1ccccc1-c1cn([C@H]2[C@@H](O)[C@@H](CO)O[C@H](Sc3ccc(Cl)c(Cl)c3)[C@@H]2OCC(=O)O)nn1] | 1.006 | 542.1 | A |
| 54 | 0.23 | 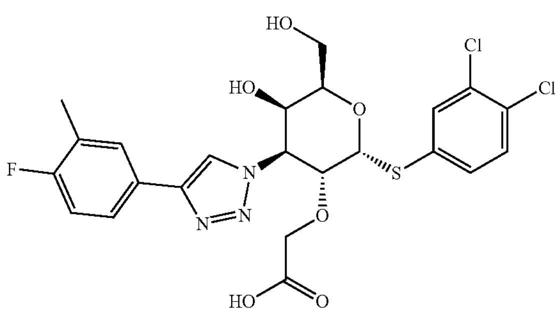 [SMILES: Cc1cc(-c2cn([C@H]3[C@@H](O)[C@@H](CO)O[C@H](Sc4ccc(Cl)c(Cl)c4)[C@@H]3OCC(=O)O)nn2)ccc1F] | 1.08 | 560.1 | A |
| 55 | 0.07 | 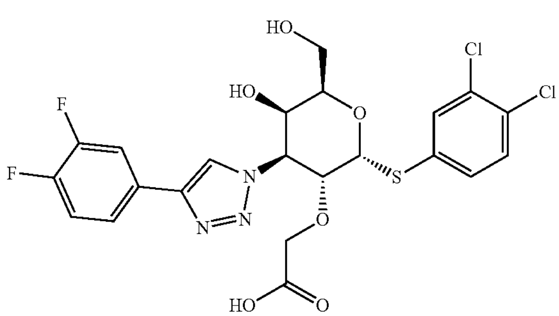 [SMILES: O=C(O)CO[C@@H]1[C@@H](n2cc(-c3ccc(F)c(F)c3)nn2)[C@@H](O)[C@@H](CO)O[C@@H]1Sc1ccc(Cl)c(Cl)c1] | 1.059 | 564 | A |

-continued

| Example | hGal3 IC$_{50}$ (uM) | Structure | LCMS RT | M + H | Method |
|---|---|---|---|---|---|
| 56 | 7.43 | 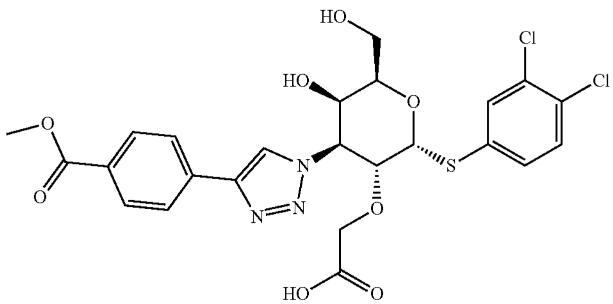 [SMILES: COC(=O)c1ccc(-c2cn([C@H]3[C@@H](O)[C@@H](CO)O[C@H](Sc4ccc(Cl)c(Cl)c4)[C@@H]3OCC(=O)O)nn2)cc1] | 1.036 | 586 | A |
| 57 | 0.31 | 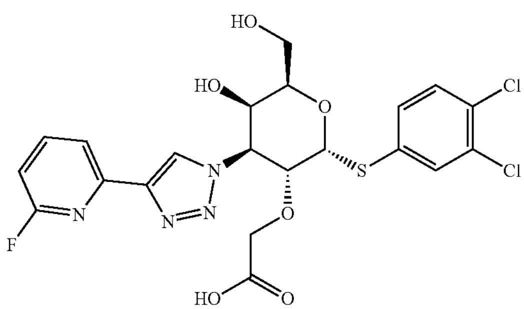 [SMILES: O=C(O)CO[C@@H]1[C@@H](n2cc(-c3cccc(F)n3)nn2)[C@@H](O)[C@@H](CO)O[C@@H]1Sc1ccc(Cl)c(Cl)c1] | 1.029 | 547 | A |
| 58 | 0.84 | 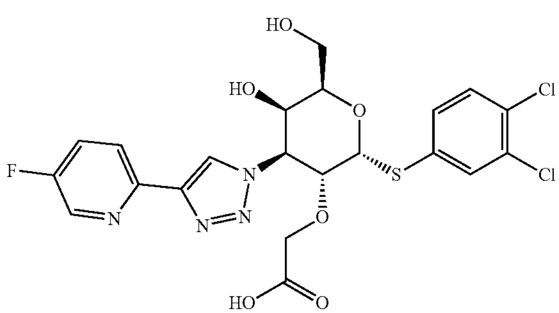 [SMILES: O=C(O)CO[C@@H]1[C@@H](n2cc(-c3ccc(F)cn3)nn2)[C@@H](O)[C@@H](CO)O[C@@H]1Sc1ccc(Cl)c(Cl)c1] | 1.015 | 547.1 | A |
| 59 | 5.55 | 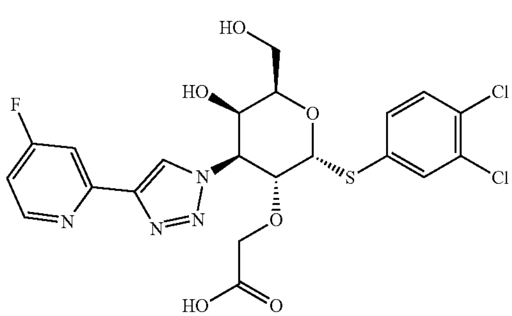 [SMILES: O=C(O)CO[C@@H]1[C@@H](n2cc(-c3cc(F)ccn3)nn2)[C@@H](O)[C@@H](CO)O[C@@H]1Sc1ccc(Cl)c(Cl)c1] | 0.914 | 547 | A |

General Synthetic Scheme for C2-Deoxy Compound:

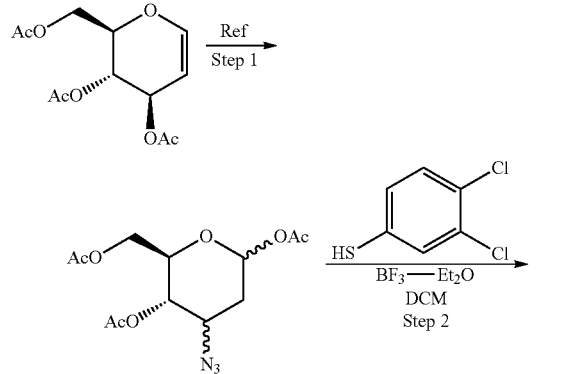

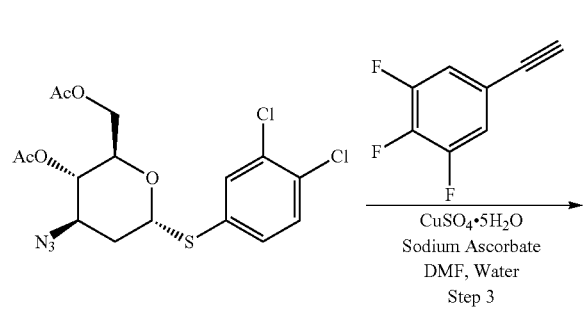

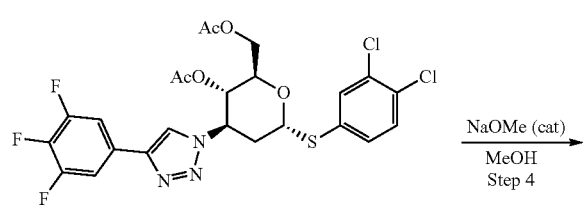

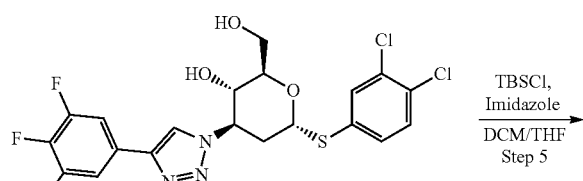

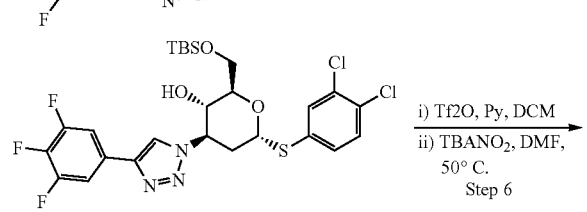

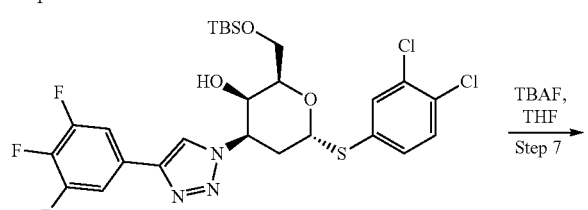

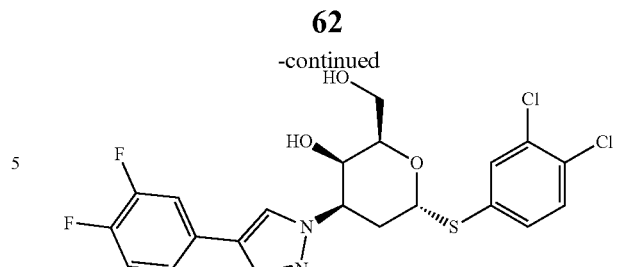

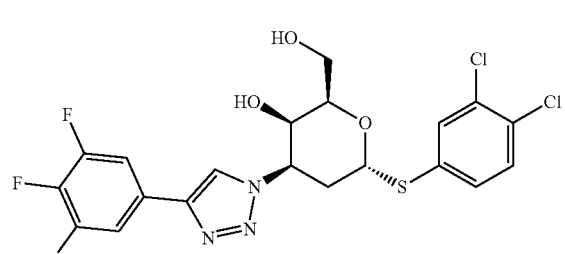

Example 60: Preparation of 2R,3R,4R,6R)-6-((3,4-dichlorophenyl)thio)-2-(hydroxymethyl)-4-(4-(3,4,5-trifluorophenyl)-1H-1,2,3-triazol-1-yl)tetrahydro-2H-pyran-3-ol

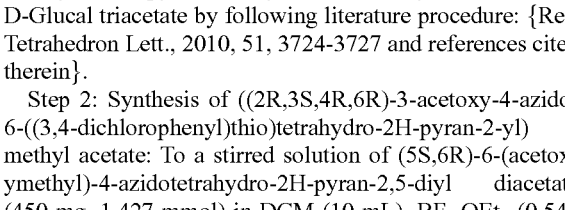

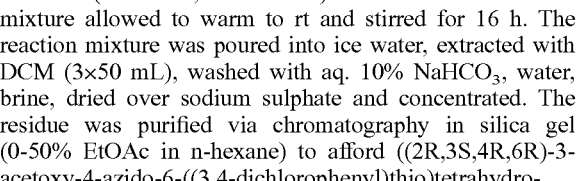

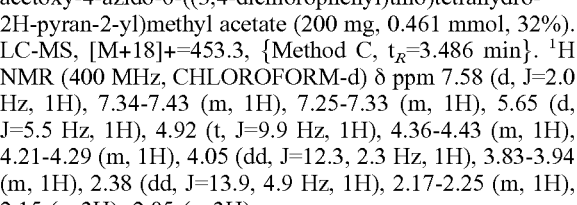

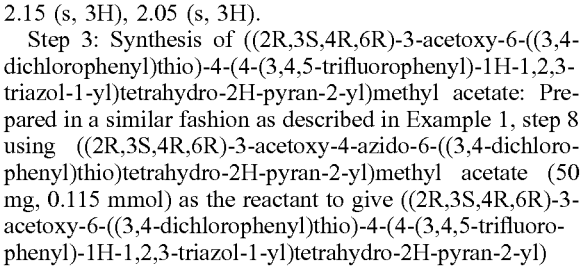

Step 1: Synthesis of (5S,6R)-6-(acetoxymethyl)-4-azido-tetrahydro-2H-pyran-2,5-diyl diacetate: Synthesized from D-Glucal triacetate by following literature procedure: {Ref: Tetrahedron Lett., 2010, 51, 3724-3727 and references cited therein}.

Step 2: Synthesis of ((2R,3S,4R,6R)-3-acetoxy-4-azido-6-((3,4-dichlorophenyl)thio)tetrahydro-2H-pyran-2-yl) methyl acetate: To a stirred solution of (5S,6R)-6-(acetoxymethyl)-4-azidotetrahydro-2H-pyran-2,5-diyl diacetate (450 mg, 1.427 mmol) in DCM (10 mL), $BF_3 \cdot OEt_2$ (0.543 mL, 4.28 mmol), was added followed by 3,4-dichlorobenzenethiol (0.236 mL, 1.855 mmol) at 0° C. Then the reaction mixture allowed to warm to rt and stirred for 16 h. The reaction mixture was poured into ice water, extracted with DCM (3×50 mL), washed with aq. 10% $NaHCO_3$, water, brine, dried over sodium sulphate and concentrated. The residue was purified via chromatography in silica gel (0-50% EtOAc in n-hexane) to afford ((2R,3S,4R,6R)-3-acetoxy-4-azido-6-((3,4-dichlorophenyl)thio)tetrahydro-2H-pyran-2-yl)methyl acetate (200 mg, 0.461 mmol, 32%). LC-MS, [M+18]+=453.3, {Method C, $t_R$=3.486 min}. $^1$H NMR (400 MHz, CHLOROFORM-d) δ ppm 7.58 (d, J=2.0 Hz, 1H), 7.34-7.43 (m, 1H), 7.25-7.33 (m, 1H), 5.65 (d, J=5.5 Hz, 1H), 4.92 (t, J=9.9 Hz, 1H), 4.36-4.43 (m, 1H), 4.21-4.29 (m, 1H), 4.05 (dd, J=12.3, 2.3 Hz, 1H), 3.83-3.94 (m, 1H), 2.38 (dd, J=13.9, 4.9 Hz, 1H), 2.17-2.25 (m, 1H), 2.15 (s, 3H), 2.05 (s, 3H).

Step 3: Synthesis of ((2R,3S,4R,6R)-3-acetoxy-6-((3,4-dichlorophenyl)thio)-4-(4-(3,4,5-trifluorophenyl)-1H-1,2,3-triazol-1-yl)tetrahydro-2H-pyran-2-yl)methyl acetate: Prepared in a similar fashion as described in Example 1, step 8 using ((2R,3S,4R,6R)-3-acetoxy-4-azido-6-((3,4-dichlorophenyl)thio)tetrahydro-2H-pyran-2-yl)methyl acetate (50 mg, 0.115 mmol) as the reactant to give ((2R,3S,4R,6R)-3-acetoxy-6-((3,4-dichlorophenyl)thio)-4-(4-(3,4,5-trifluorophenyl)-1H-1,2,3-triazol-1-yl)tetrahydro-2H-pyran-2-yl)

methyl acetate (60 mg, 0.102 mmol, 88% yield) as an off-white solid. LC-MS, [M+H]$^+$=590.3, {Method E: $t_R$=1.69 min}.

Step 4: Synthesis of (2R,3S,4R,6R)-6-((3,4-dichlorophenyl)thio)-2-(hydroxymethyl)-4-(4-(3,4,5-trifluorophenyl)-1H-1,2,3-triazol-1-yl)tetrahydro-2H-pyran-3-ol: Prepared in a similar fashion as described in Example 1, step-5 using ((2R,3S,4R,6R)-3-acetoxy-6-((3,4-dichlorophenyl)thio)-4-(4-(3,4,5-trifluorophenyl)-1H-1,2,3-triazol-1-yl)tetrahydro-2H-pyran-2-yl)methyl acetate (60 mg, 0.102 mmol) as the reactant to give (2R,3S,4R,6R)-6-((3,4-dichlorophenyl)thio)-2-(hydroxymethyl)-4-(4-(3,4,5-trifluorophenyl)-1H-1,2,3-triazol-1-yl)tetrahydro-2H-pyran-3-ol (55 mg, crude). LC-MS, [M+H]$^+$=506.0, {Method A: $t_R$=2.041 min}. $^1$H NMR (400 MHz, METHANOL-d$_4$) δ ppm 8.40 (s, 1H), 7.72-7.79 (m, 1H), 7.57-7.66 (m, 2H), 7.48-7.50 (m, 2H), 5.93 (dd, J=11.5, 2.5 Hz, 1H), 5.03-5.11 (m, 1H), 3.96-4.09 (m, 1H), 3.79-3.90 (m, 2H), 3.63-3.72 (m, 1H), 2.61-2.71 (m, 1H), 2.35-2.49 (m, 1H).

Step 5: Synthesis of ((2R,3S,4R,6R)-2-(((tert-butyldimethylsilyl)oxy)methyl)-6-((3,4-dichlorophenyl)thio)-4-(4-(3,4,5-trifluorophenyl)-1H-1,2,3-triazol-1-yl)tetrahydro-2H-pyran-3-ol: To a solution of (2R,3S,4R,6R)-6-((3,4-dichlorophenyl)thio)-2-(hydroxymethyl)-4-(4-(3,4,5-trifluorophenyl)-1H-1,2,3-triazol-1-yl)tetrahydro-2H-pyran-3-ol (40 mg, 0.079 mmol) in DCM (5 mL), imidazole (16.13 mg, 0.237 mmol), 4-dimethylaminopyridine (0.965 mg, 7.90 μmol), TBDMS-Cl (14.29 mg, 0.095 mmol) were added sequentially at 0° C. under nitrogen. Then the reaction mixture was allowed to warm to rt and stirred for 16 h. The reaction mixture was diluted with DCM (2×50 mL), washed with water (50 mL), brine solution (50 mL), dried over sodium sulphate and concentrated. The crude residue was purified by via chromatography in silica gel (0-30% EtOAc in n-hexane) to yield (2R,3S,4R,6R)-2-(((tert-butyldimethylsilyl)oxy)methyl)-6-((3,4-dichlorophenyl)thio)-4-(4-(3,4,5-trifluorophenyl)-1H-1,2,3-triazol-1-yl)tetrahydro-2H-pyran-3-ol (30 mg, 0.048 mmol, 60%) as a colourless liquid. LC-MS, [M+H]$^+$=621.0, {Method C: $t_R$=2.495 min}.

Step 6: Synthesis of 2R,3R,4R,6R)-2-(((tert-butyldimethylsilyl)oxy)methyl)-6-((3,4-dichlorophenyl)thio)-4-(4-(3,4,5-trifluorophenyl)-1H-1,2,3-triazol-1-yl)tetrahydro-2H-pyran-3-ol: To a solution of ((2R,3S,4R,6R)-2-(((tert-butyldimethylsilyl)oxy)methyl)-6-((3,4-dichlorophenyl)thio)-4-(4-(3,4,5-trifluorophenyl)-1H-1,2,3-triazol-1-yl)tetrahydro-2H-pyran-3-ol (30 mg, 0.048 mmol) in DCM (5 mL), pyridine (0.012 mL, 0.145 mmol) was added followed by Tf$_2$O (0.012 mL, 0.073 mmol) at −15° C. and the mixture was stirred for 1 h. Then, the reaction mixture was diluted with DCM (30 mL), washed with 0.7 N HCl (20 mL) followed by 10% NaHCO$_3$ (20 mL) and brine solution (20 mL). The organic layer was dried over Na$_2$SO$_4$ and concentrated to give the crude triflate (20 mg, 0.027 mmol) as a yellow liquid. This was dissolved in DMF (2 mL), treated with tetrabutylammonium nitrite (23.00 mg, 0.080 mmol) at rt under argon and heated at 50° C. for 16 h. The reaction mixture was quenched with ice cold water, extracted with EtOAc (2×20 mL); washed with water, brine solution, dried over sodium sulphate and concentrated to yield (2R,3R,4R,6R)-2-(((tert-butyldimethylsilyl)oxy)methyl)-6-((3,4-dichlorophenyl)thio)-4-(4-(3,4,5-trifluorophenyl)-1H-1,2,3-triazol-1-yl)tetrahydro-2H-pyran-3-ol (12 mg, 0.019 mmol, 73%) as a yellow liquid. LC-MS, [M+H]$^+$=618.2, {Method E: $t_R$=1.48 min}.

Step 7: To a solution of (2R,3R,4R,6R)-2-(((tert-butyldimethylsilyl)oxy)methyl)-6-((3,4-dichlorophenyl)thio)-4-(4-(3,4,5-trifluorophenyl)-1H-1,2,3-triazol-1-yl)tetrahydro-2H-pyran-3-ol (12 mg, 0.019 mmol) in THF (2 mL) was added TBAF (0.058 mL, 0.058 mmol, 1M in THF) and stirred at rt for 1 h. Then the reaction mixture was concentrated under reduced pressure and purified by prep-HPLC Method A to afford Example 60 (2R,3R,4R,6R)-6-((3,4-dichlorophenyl)thio)-2-(hydroxymethyl)-4-(4-(3,4,5-trifluorophenyl)-1H-1,2,3-triazol-1-yl)tetrahydro-2H-pyran-3-ol (5.7 mg, 0.011 mmol, 58%). LC-MS, [M+H]$^+$=508.0, {Method A: $t_R$=2.049 min}. $^1$H NMR (400 MHz, METHANOL-d$_4$) δ ppm 8.52 (s, 1H), 7.80 (d, J=1.7 Hz, 1H), 7.66 (dd, J=8.6, 6.8 Hz, 2H), 7.47-7.56 (m, 2H), 5.96 (d, J=5.6 Hz, 1H), 5.13-5.21 (m, 1H), 4.50 (t, J=6.2 Hz, 1H), 4.21 (d, J=0.7 Hz, 1H), 3.71-3.81 (m, 2H), 3.16 (td, J=13.4, 5.6 Hz, 1H), 2.36 (dd, J=13.9, 4.6 Hz, 1H). hGal3 IC$_{50}$=2.20 uM.

General Synthetic Scheme for C2-Deoxy Sulfone Analog

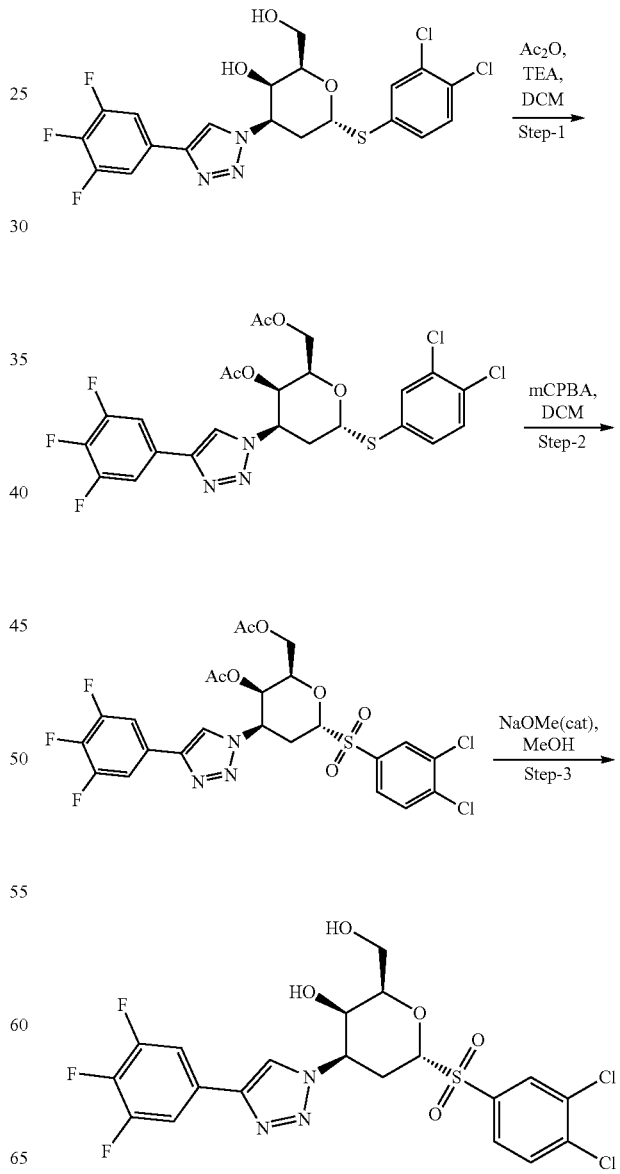

Example 61: Preparation of ((2R,3R,4R,6R)-6-((3,4-dichlorophenyl)sulfonyl)-2-(hydroxymethyl)-4-(4-(3,4,5-trifluorophenyl)-1H-1,2,3-triazol-1-yl)tetrahydro-2H-pyran-3-ol

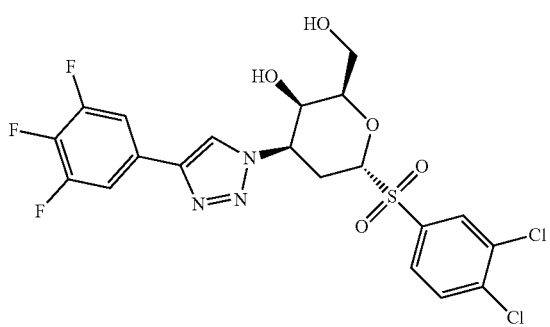 [SMILES: O=S(=O)(c1ccc(Cl)c(Cl)c1)[C@@H]1C[C@@H](n2cc(-c3cc(F)c(F)c(F)c3)nn2)[C@@H](O)[C@@H](CO)O1]

Step 1: Synthesis of ((2R,3R,4R,6R)-3-acetoxy-6-((3,4-dichlorophenyl)thio)-4-(4-(3,4,5-trifluorophenyl)-1H-1,2,3-triazol-1-yl)tetrahydro-2H-pyran-2-yl)methyl acetate: To a solution of Example 60 (2R,3R,4R,6R)-6-((3,4-dichlorophenyl)thio)-2-(hydroxymethyl)-4-(4-(3,4,5-trifluorophenyl)-1H-1,2,3-triazol-1-yl)tetrahydro-2H-pyran-3-ol (150 mg, 0.296 mmol) in DCM (5 mL), TEA (0.206 mL, 1.481 mmol), Ac$_2$O (0.140 mL, 1.481 mmol) and catalytic DMAP were added at 0° C. Then reaction mixture was allowed to reach rt and stirred for 1 h. The reaction mixture was extracted with DCM (3×50 mL), washed with sat NH$_4$Cl (50 mL), brine solution (50 mL), dried over Na$_2$SO$_4$ and concentrated to give ((2R,3R,4R,6R)-3-acetoxy-6-((3,4-dichlorophenyl)thio)-4-(4-(3,4,5-trifluorophenyl)-1H-1,2,3-triazol-1-yl)tetrahydro-2H-pyran-2-yl)methyl acetate (170 mg, 0.283 mmol, 96%) as a yellow solid. LC-MS, [M+H]$^+$=592.0, {Method C: t$_R$=3.827 min}. $^1$H NMR (400 MHz, CHLOROFORM-d) δ 7.78 (s, 1H), 7.65 (d, J=2.3 Hz, 1H), 7.47-7.39 (m, 3H), 7.38-7.32 (m, 1H), 5.92 (d, J=5.3 Hz, 1H), 5.53 (s, 1H), 5.19-5.10 (m, 1H), 4.80 (t, J=6.0 Hz, 1H), 4.21-4.05 (m, 2H), 3.33-3.31 (m, 1H), 2.46 (dd, J=13.6, 4.1 Hz, 1H), 2.02 (d, J=6.8 Hz, 6H).

Step 2: Synthesis of ((2R,3R,4R,6R)-3-acetoxy-6-((3,4-dichlorophenyl)sulfonyl)-4-(4-(3,4,5-trifluorophenyl)-1H-1,2,3-triazol-1-yl)tetrahydro-2H-pyran-2-yl)methyl acetate: To a stirred solution of ((2R,3R,4R,6R)-3-acetoxy-6-((3,4-dichlorophenyl)thio)-4-(4-(3,4,5-trifluorophenyl)-1H-1,2,3-triazol-1-yl)tetrahydro-2H-pyran-2-yl)methyl acetate (180 mg, 0.305 mmol) in DCM (5 mL), was added mCPBA (225 mg, 0.915 mmol) at 0° C. Then reaction mixture was allowed to reach rt and stirred for 1 h. Then the reaction mixture was diluted with DCM (2×50 mL), washed with aq.NaHCO$_3$, water, brine solution, dried over sodium sulphate and concentrated. Crude residue was purified via chromatography in silica gel (0-10% MeOH in CHCl$_3$) to yield ((2R,3R,4R,6R)-3-acetoxy-6-((3,4-dichlorophenyl)sulfonyl)-4-(4-(3,4,5-trifluorophenyl)-1H-1,2,3-triazol-1-yl)tetrahydro-2H-pyran-2-yl)methyl acetate (120 mg, 0.185 mmol, 61%) as a yellow solid. LC-MS, [M+H]$^+$=622.0, {Method C: t$_R$=3.515 min}.

Step 3: Synthesis of ((2R,3R,4R,6R)-6-((3,4-dichlorophenyl)sulfonyl)-2-(hydroxymethyl)-4-(4-(3,4,5-trifluorophenyl)-1H-1,2,3-triazol-1-yl)tetrahydro-2H-pyran-3-ol: Prepared in a similar fashion as described in Example 1, step-5 using ((2R,3R,4R,6R)-3-acetoxy-6-((3,4-dichlorophenyl)sulfonyl)-4-(4-(3,4,5-trifluorophenyl)-1H-1,2,3-triazol-1-yl)tetrahydro-2H-pyran-2-yl)methyl acetate (40 mg, 0.064 mmol) as the reactant and the crude residue was purified by prep-HPLC Method A to afford Example 61 (2R,3R,4R,6R)-6-((3,4-dichlorophenyl)sulfonyl)-2-(hydroxymethyl)-4-(4-(3,4,5-trifluorophenyl)-1H-1,2,3-triazol-1-yl)tetrahydro-2H-pyran-3-ol (18.0 mg, 0.032 mmol, 50%). LC-MS, [M+H]$^+$=538.0, {Method C: t$_R$=2.816 min}. $^1$H NMR (400 MHz, METHANOL-d$_4$) δ 8.58 (s, 1H), 8.18 (d, J=2.0 Hz, 1H), 7.94-7.91 (m, 1H), 7.84 (d, J=8.4 Hz, 1H), 7.68-7.63 (m, 2H), 5.54-5.49 (m, 1H), 5.27 (d, J=6.8 Hz, 1H), 4.77-4.72 (m, 1H), 4.22 (s, 1H), 3.68-3.61 (m, 2H), 3.13-3.05 (m, 1H), 2.93-2.89 (m, 1H). hGal3 IC$_{50}$=0.16 uM.

General Synthetic Scheme for C2-Fluoro Compounds:

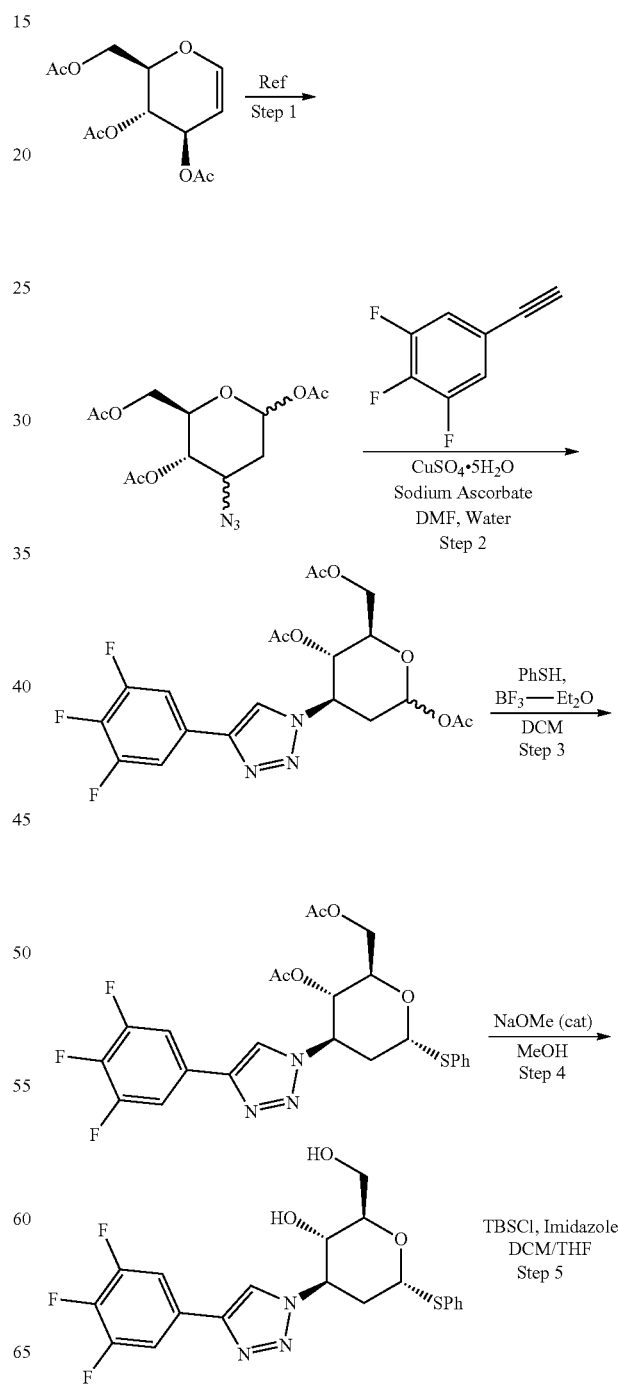

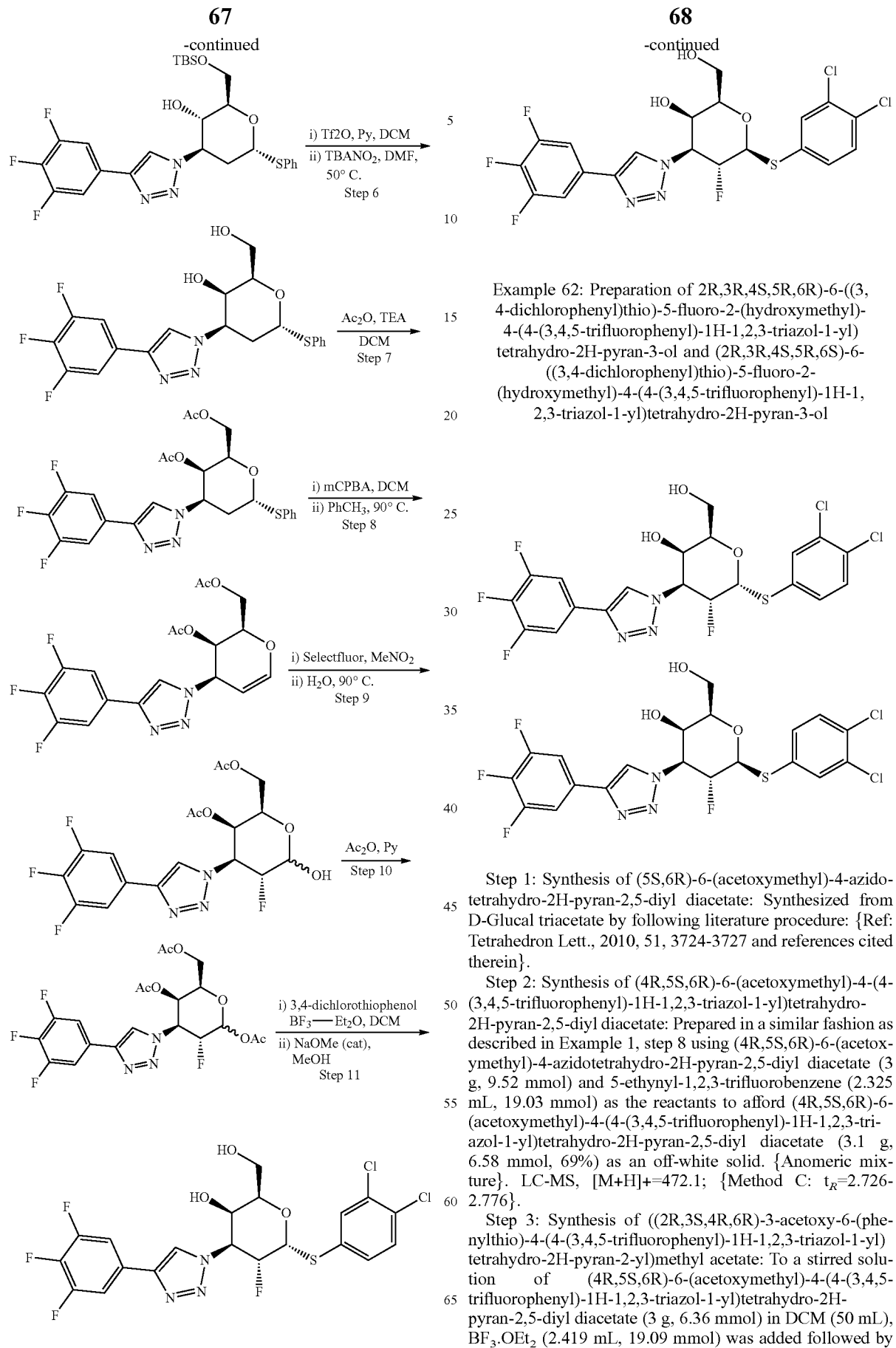

Example 62: Preparation of 2R,3R,4S,5R,6R)-6-((3,4-dichlorophenyl)thio)-5-fluoro-2-(hydroxymethyl)-4-(4-(3,4,5-trifluorophenyl)-1H-1,2,3-triazol-1-yl)tetrahydro-2H-pyran-3-ol and (2R,3R,4S,5R,6S)-6-((3,4-dichlorophenyl)thio)-5-fluoro-2-(hydroxymethyl)-4-(4-(3,4,5-trifluorophenyl)-1H-1,2,3-triazol-1-yl)tetrahydro-2H-pyran-3-ol Step 1: Synthesis of (5S,6R)-6-(acetoxymethyl)-4-azido-tetrahydro-2H-pyran-2,5-diyl diacetate: Synthesized from D-Glucal triacetate by following literature procedure: {Ref: Tetrahedron Lett., 2010, 51, 3724-3727 and references cited therein}.

Step 2: Synthesis of (4R,5S,6R)-6-(acetoxymethyl)-4-(4-(3,4,5-trifluorophenyl)-1H-1,2,3-triazol-1-yl)tetrahydro-2H-pyran-2,5-diyl diacetate: Prepared in a similar fashion as described in Example 1, step 8 using (4R,5S,6R)-6-(acetoxymethyl)-4-azidotetrahydro-2H-pyran-2,5-diyl diacetate (3 g, 9.52 mmol) and 5-ethynyl-1,2,3-trifluorobenzene (2.325 mL, 19.03 mmol) as the reactants to afford (4R,5S,6R)-6-(acetoxymethyl)-4-(4-(3,4,5-trifluorophenyl)-1H-1,2,3-triazol-1-yl)tetrahydro-2H-pyran-2,5-diyl diacetate (3.1 g, 6.58 mmol, 69%) as an off-white solid. {Anomeric mixture}. LC-MS, [M+H]+=472.1; {Method C: $t_R$=2.726-2.776}.

Step 3: Synthesis of ((2R,3S,4R,6R)-3-acetoxy-6-(phenylthio)-4-(4-(3,4,5-trifluorophenyl)-1H-1,2,3-triazol-1-yl)tetrahydro-2H-pyran-2-yl)methyl acetate: To a stirred solution of (4R,5S,6R)-6-(acetoxymethyl)-4-(4-(3,4,5-trifluorophenyl)-1H-1,2,3-triazol-1-yl)tetrahydro-2H-pyran-2,5-diyl diacetate (3 g, 6.36 mmol) in DCM (50 mL), $BF_3 \cdot OEt_2$ (2.419 mL, 19.09 mmol) was added followed by benzenethiol (0.912 g, 8.27 mmol) at 0° C. The reaction mixture allowed to warm to rt and stirred for 16 h. The reaction mixture was poured into ice water, extracted with DCM (3×50 mL), washed with aq. 10% NaHCO$_3$, water, brine, dried over sodium sulphate and concentrated. The residue was purified via chromatography in silica gel (0-50% EtOAc in n-hexane) to afford ((2R,3S,4R,6R)-3-acetoxy-6-(phenylthio)-4-(4-(3,4,5-trifluorophenyl)-1H-1,2,3-triazol-1-yl)tetrahydro-2H-pyran-2-yl)methyl acetate (2.1 g, 4.03 mmol, 63%) as an off-white solid. LC-MS, [M+H]+= 522.1, {Method C, t$_R$=3.475 min}.

Step 4: Synthesis of (2R,3S,4R,6R)-2-(hydroxymethyl)-6-(phenylthio)-4-(4-(3,4,5-trifluorophenyl)-1H-1,2,3-triazol-1-yl)tetrahydro-2H-pyran-3-ol: Prepared in a similar fashion as described in Example 1, step 5 using ((2R,3S,4R)-3-acetoxy-6-(phenylthio)-4-(4-(3,4,5-trifluorophenyl)-1H-1,2,3-triazol-1-yl)tetrahydro-2H-pyran-2-yl)methyl acetate (2.1 g, 4.03 mmol) as the reactant to give (2R,3S,4R)-2-(hydroxymethyl)-6-(phenylthio)-4-(4-(3,4,5-trifluorophenyl)-1H-1,2,3-triazol-1-yl)tetrahydro-2H-pyran-3-ol (1.3 g, 2.58 mmol, 64%) as an off-white solid. LC-MS, [M+H]+=438.2, {t$_R$=2.55 min, Method C}.

Step 5: Synthesis of (2R,3S,4R,6R)-2-(((tert-butyldimethylsilyl)oxy)methyl)-6-(phenylthio)-4-(4-(3,4,5-trifluorophenyl)-1H-1,2,3-triazol-1-yl)tetrahydro-2H-pyran-3-ol: Prepared in a similar fashion as described in Example 60, step-5 using (2R,3S,4R)-2-(hydroxymethyl)-6-(phenylthio)-4-(4-(3,4,5-trifluorophenyl)-1H-1,2,3-triazol-1-yl)tetrahydro-2H-pyran-3-ol (1.3 g, 2.97 mmol) as the reactant to give (2R,3S,4R,6R)-2-(((tertbutyldimethylsilyl)oxy)methyl)-6-(phenylthio)-4-(4-(3,4,5-trifluorophenyl)-1H-1,2,3-triazol-1-yl)tetrahydro-2H-pyran-3-ol (750 mg, 1.317 mmol, 44%) as an off-white solid. LC-MS, [M+H]+=552.2 {t$_R$=1.607 min, Method C}. $^1$H NMR (400 MHz, CHLOROFORM-d): δ 7.94 (s, 1H), 7.53-7.43 (m, 4H), 7.39-7.28 (m, 3H), 5.77 (d, J=4.8 Hz, 1H), 4.79 (ddd, J=13.3, 9.4, 4.4 Hz, 1H), 4.34 (ddd, J=9.1, 7.4, 4.5 Hz, 1H), 4.08 (td, J=9.4, 1.8 Hz, 1H), 3.98-3.91 (m, 2H), 3.84 (dd, J=10.3, 7.5 Hz, 1H), 3.00 (td, J=13.4, 5.8 Hz, 1H), 2.64 (dd, J=13.1, 4.4 Hz, 1H), 0.94 (s, 9H), 0.09 (s, 6H).

Step 6: Synthesis of (2R,3R,4R,6R)-2-(hydroxymethyl)-6-(phenylthio)-4-(4-(3,4,5-trifluorophenyl)-1H-1,2,3-triazol-1-yl)tetrahydro-2H-pyran-3-ol: Prepared in a similar fashion as described in Example 60, step 6 using (2R,3S,4R,6R)-2-(((tert-butyldimethylsilyl)oxy)methyl)-6-(phenylthio)-4-(4-(3,4,5-trifluorophenyl)-1H-1,2,3-triazol-1-yl)tetrahydro-2H-pyran-3-ol (800 mg, 1.450 mmol) as the reactant to give (2R,3R,4R,6R)-2-(hydroxymethyl)-6-(phenylthio)-4-(4-(3,4,5-trifluorophenyl)-1H-1,2,3-triazol-1-yl)tetrahydro-2Hpyran-3-ol (300 mg, 0.683 mmol, 58%) as an off-white solid. LC-MS, [M+H]+=438.2, {Method C: t$_R$=2.59 min}. 1H NMR (400 MHz, METHANOL-d4): δ 8.42 (s, 1H), 7.56-7.48 (m, 4H), 7.26-7.19 (m, 3H), 5.76 (d, J=5.2 Hz, 1H), 5.09-5.05 (m, 1H), 4.46-4.43 (m, 1H), 4.10 (s, 1H), 3.68-3.57 (m, 2H), 3.04-2.97 (m, 1H), 2.24 (dd, J=13.2, 4.0 Hz, 1H).

Step 7: Synthesis of ((2R,3R,4R,6R)-3-acetoxy-6-(phenylthio)-4-(4-(3,4,5-trifluorophenyl)-1H-1,2,3-triazol-1-yl)tetrahydro-2H-pyran-2-yl)methyl acetate: Prepared in a similar fashion as described in Example 61, step 1 using (2R,3R,4R,6R)-2-(hydroxymethyl)-6-(phenylthio)-4-(4-(3,4,5-trifluorophenyl)-1H-1,2,3-triazol-1-yl)tetrahydro-2H-pyran-3-ol (360 mg, 0.823 mmol) as the starting material to afford to give ((2R,3R,4R,6R)-3-acetoxy-6-(phenylthio)-4-(4-(3,4,5-trifluorophenyl)-1H-1,2,3-triazol-1-yl)tetrahydro-2H-pyran-2-yl)methyl acetate (350 mg, 0.642 mmol, 78%) as a pale yellow solid. LC-MS, [M+H]+=522.2, {t$_R$=3.275 min, Method C}.

Step 8: Synthesis of ((2R,3R,4R)-3-acetoxy-4-(4-(3,4,5-trifluorophenyl)-1H-1,2,3-triazol-1-yl)-3,4-dihydro-2H-pyran-2-yl)methyl acetate: To a solution of ((2R,3R,4R,6R)-3-acetoxy-6-(phenylthio)-4-(4-(3,4,5-trifluorophenyl)-1H-1,2,3-triazol-1-yl)tetrahydro-2H-pyran-2-yl)methyl acetate (300 mg, 0.575 mmol) in DCM (20 mL), m-CPBA (142 mg, 0.575 mmol) in DCM (0.5 mL) was added at 0° C. and stirred at the same temperature for 30 min. The reaction mixture was diluted with DCM (20 mL), washed with sat NaHCO$_3$, sat NaCl, dried over sodium sulphate and concentrated to give crude residue which was taken as such for next step without further purification. The crude sulfoxid (300 mg, 0.558 mmol) thus obtained was dissolved in toluene (20 mL) and heated at 90° C. for 12 h. The solvent was removed under reduced pressure to get the crude residue which was purified via chromatography in silica gel (0-50% EtOAc in n-hexane) to afford ((2R,3R,4R)-3-acetoxy-4-(4-(3,4,5-trifluorophenyl)-1H-1,2,3-triazol-1-yl)-3,4-dihydro-2H-pyran-2-yl)methyl acetate (180 mg, 0.392 mmol, 70%) as an off-white solid. LC-MS, [M+H]+=412.0, {Method C: t$_R$=2.639 min}. 1H NMR (400 MHz, CHLOROFORM-d): δ 7.79 (s, 1H), 7.48-7.40 (m, 2H), 6.74 (dd, J=6.3, 2.3 Hz, 1H), 5.82-5.78 (m, 1H), 5.65 (d, J=5.0 Hz, 1H), 4.92 (dt, J=6.1, 1.9 Hz, 1H), 4.50 (t, J=6.5 Hz, 1H), 4.27-4.18 (m, 2H), 2.10 (s, 3H), 1.91 (s, 3H).

Step 9: Synthesis of ((2R,3R,4S,5R)-3-acetoxy-5-fluoro-6-hydroxy-4-(4-(3,4,5-trifluorophenyl)-1H-1,2,3-triazol-1-yl)tetrahydro-2H-pyran-2-yl)methyl acetate: To a solution of ((2R,3R,4R)-3-acetoxy-4-(4-(3,4,5-trifluorophenyl)-1H-1,2,3-triazol-1-yl)-3,4-dihydro-2Hpyran-2-yl)methyl acetate (100 mg, 0.243 mmol) in nitromethane (2 mL), 1-chloromethyl-4-fluoro-1,4-diazoniabicyclo[2.2.2]octane bis(tetrafluoroborate) (103 mg, 0.292 mmol) was added at rt and stirred for 12 h. Then, Water (0.4 mL) was added and heated at 90° C. for 5 h. Solvent was removed under reduced pressure, crude was extracted with with EtOAc (2×20 mL), washed with water, brine, dried over Na$_2$SO$_4$ and concentrated. The crude residue was purified via chromatography in silica gel (0-60% EtOAc in n-hexane) to afford ((2R,3R,4S,5R)-3-acetoxy-5-fluoro-6-hydroxy-4-(4-(3,4,5-trifluorophenyl)-1H-1,2,3-triazol-1-yl)tetrahydro-2H-pyran-2-yl)methyl acetate (100 mg, 0.210 mmol, 86%) as an off-white solid. LC-MS, [M+1]=448.1, {Method C: t$_R$=2.377 & 2.469 min}.

Step 10: Synthesis of (3R,4S,5R,6R)-6-(acetoxymethyl)-3-fluoro-4-(4-(3,4,5-trifluorophenyl)-1H-1,2,3-triazol-1-yl)tetrahydro-2H-pyran-2,5-diyl diacetate: To a stirred solution of ((2R,3R,4S,5R)-3-acetoxy-5-fluoro-6-hydroxy-4-(4-(3,4,5-trifluorophenyl)-1H-1,2,3-triazol-1-yl)tetrahydro-2H-pyran-2-yl)methyl acetate (100 mg, 0.224 mmol) in pyridine (5 mL) was added acetic anhydride (0.105 mL, 1.118 mmol) at rt and stirred for 2 h. Solvent was removed under reduced pressure and the crude residue was purified via chromatography in silica gel (0-60% EtOAc in n-hexane) to afford (3R,4S,5R,6R)-6-(acetoxymethyl)-3-fluoro-4-(4-(3,4,5-trifluorophenyl)-1H-1,2,3-triazol-1-yl)tetrahydro-2H-pyran-2,5-diyl diacetate (65 mg, 0.126 mmol, 56%) as an off-white solid. LC-MS, [M+1]=490.0, {Method C: t$_R$=2.846 min}.

Step 11: Synthesis of (2R,3R,4S,5R,6R)-6-((3,4-dichlorophenyl)thio)-5-fluoro-2-(hydroxymethyl)-4-(4-(3,4,5-trifluorophenyl)-1H-1,2,3-triazol-1-yl)tetrahydro-2H-pyran-3-ol: To a stirred solution of (3R,4S,5R,6R)-6-(acetoxymethyl)-3-fluoro-4-(4-(3,4,5-trifluorophenyl)-1H-1,2,3-triazol-1-yl)tetrahydro-2H-pyran-2,5-diyl diacetate (50 mg, 0.102 mmol) in DCM (5 mL), BF$_3$-OEt$_2$ (0.129 mL, 1.022 mmol) and 3,4-dichlorobenzenethiol (0.026 mL, 0.204 mmol) were added at 0° C. under Argon. Then the reaction mixture was allowed to reach rt and stirred for 72 h. Solvent was removed under reduced pressure, crude residue was dissolved in MeOH (2 mL), treated with sodium methoxide (25% solution in Methanol) (4.42 mg, 0.020 mmol) at rt and stirred for 30 min. Then the solvent was removed under reduced pressure, crude was purified by prep-HPLC Method D to get product as anomeric mixture.

Anomeric mixture was further purified by prep-HPLC Method J to afford Example 62 (isomer-1) (2R,3R,4S,5R,6R)-6-((3,4-dichlorophenyl)thio)-5-fluoro-2-(hydroxymethyl)-4-(4-(3,4,5-trifluorophenyl)-1H-1,2,3-triazol-1-yl) tetrahydro-2H-pyran-3-ol (1 mg, 2%, isomer-1). LC-MS, [M+H]$^+$=524.1, {Method A: $t_R$=2.057 min}. $^1$H NMR (400 MHz, METHANOL-d4) δ 8.69 (s, 1H), 7.83 (d, J=2.0 Hz, 1H), 7.75-7.62 (m, 2H), 7.60-7.48 (m, 2H), 6.06 (d, J=5.9 Hz, 1H), 5.86-5.74 (m, 1H), 5.32-5.18 (m, 1H), 4.61-4.51 (m, 2H), 4.30 (br. s., 1H), 3.75 (d, J=5.9 Hz, 2H). hGal3 IC$_{50}$=2.2 uM.

Example 62 (Isomer-2)

(2R,3R,4S,5R,6S)-6-((3,4-dichlorophenyl)thio)-5-fluoro-2-(hydroxymethyl)-4-(4-(3,4,5-trifluorophenyl)-1H-1,2,3-triazol-1-yl)tetrahydro-2H-pyran-3-ol (1 mg, 2%, isomer-2). LC-MS, [M+H]$^+$=524.1, {Method A: $t_R$=2.074 min}. 1H NMR (400 MHz, METHANOL-d4) δ 8.67 (s, 1H), 7.84 (d, J=1.5 Hz, 1H), 7.68 (dd, J=9.0, 6.5 Hz, 2H), 7.59-7.51 (m, 2H), 5.33-5.07 (m, 3H), 4.27-4.23 (m, 1H), 3.97 (t, J=6.0 Hz, 1H), 3.87-3.81 (m, 1H), 3.75 (dd, J=11.5, 5.5 Hz, 1H) (one proton might be obscured with moisture peak). hGal3 IC$_{50}$=10 uM.

Synthetic Scheme for Imidazole Analog

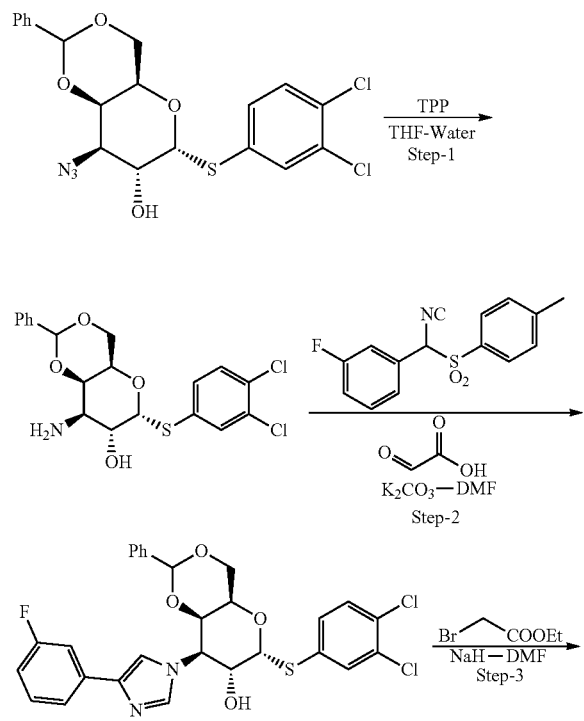

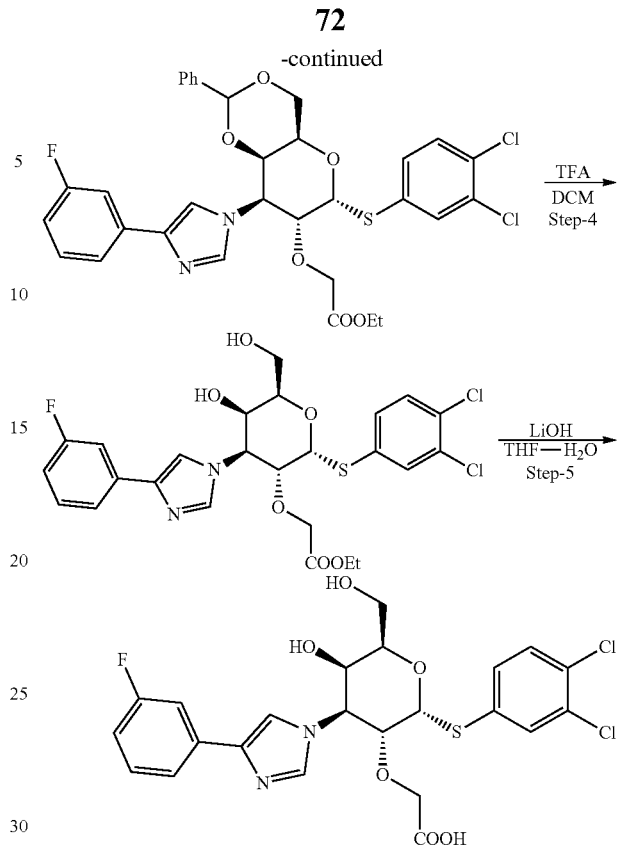

Example 63: Preparation of 2-(((2R,3R,4S,5R,6R)-2-((3,4-dichlorophenyl)thio)-4-(4-(3-fluorophenyl)-1H-imidazol-1-yl)-5-hydroxy-6-(hydroxymethyl)tetrahydro-2H-pyran-3-yl)oxy)acetic acid

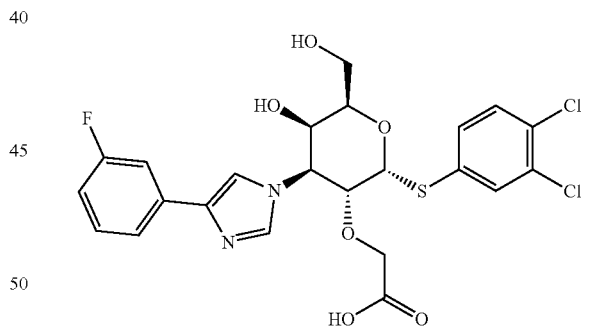

Step 1: Synthesis of (4aR,6R,7R,8R,8aR)-8-amino-6-((3,4-dichlorophenyl)thio)-2-phenylhexahydropyrano[3,2-d][1,3]dioxin-7-ol: To a stirred solution of (4aR,6R,7R,8R,8aR)-8-azido-6-((3,4-dichlorophenyl)thio)-2-phenylhexahydropyrano[3,2-d][1,3]dioxin-7-ol (300 mg, 0.660 mmol) and triphenylphosphine (346 mg, 1.321 mmol) in tetrahydrofuran (10 mL) was added water (0.297 mL, 16.51 mmol) and the reaction mixture was refluxed for overnight. The reaction mixture was concentrated to dryness, 30% EtOAc in Hexane (15 mL) was added and stirred for 15 minutes. Then the solid was filtered, washed with 10% EtOAc in hexane and dried to afford (4aR,6R,7R,8R,8aR)-8-amino-6-((3,4-dichlorophenyl)thio)-2-phenylhexahydropyrano[3,2-d][1,3]dioxin-7-ol (230 mg, 0.537 mmol, 81%) as an off-white solid. $^1$H NMR (400 MHz, DMSO-$d_6$) δ 7.71 (d, J=2.5 Hz, 1H), 7.57 (d, J=8.5 Hz, 1H), 7.47-7.42 (m, 3H), 7.41-7.35 (m, 3H), 5.87 (d, J=5.0 Hz, 1H), 5.61 (s, 1H), 5.52 (d, J=4.5 Hz, 1H), 4.19 (d, J=3.0 Hz, 1H), 4.11-4.08 (m, 1H), 3.99 (s, 1H), 3.93-3.83 (m, 2H), 2.79 (dd, J=10.5, 3.0 Hz, 1H), 1.56 (br. s., 2H). LC-MS, [M+H]$^+$= 428.0, {Method C: $t_R$=2.814 min}.

Step 2: Synthesis of (4aR,6R,7R,8R,8aR)-6-((3,4-dichlorophenyl)thio)-8-(4-(3-fluorophenyl)-1H-imidazol-1-yl)-2-phenylhexahydropyrano[3,2-d][1,3]dioxin-7-ol: (4aR,6R,7R,8R,8aR)-8-amino-6-((3,4-dichlorophenyl)thio)-2-phenylhexahydropyrano[3,2-d][1,3]dioxin-7-ol (150 mg, 0.350 mmol), 2-oxoacetic acid, H$_2$O (29.0 mg, 0.315 mmol) and K$_2$CO$_3$ (242 mg, 1.751 mmol) in DMF (0.5 mL) was stirred at room temperature for 2 h. Then 1-fluoro-3-(isocyano(tosyl)methyl)benzene (101 mg, 0.350 mmol) was added and stirring continued for overnight at rt. The reaction mass quenched with ice water and stirred for 30 minutes. Precipitated solid was filtered, washed with excess water and dried to afford (4aR,6R,7R,8R,8aR)-6-((3,4-dichlorophenyl)thio)-8-(4-(3-fluorophenyl)-1Himidazol-1-yl)-2-phenylhexahydropyrano[3,2-d][1,3]dioxin-7-ol (170 mg, 0.296 mmol, 65%) as brown solid which was as such taken for the next step without further purification. $^1$H NMR (400 MHz, METHANOL-d4) δ 7.75 (d, J=1.0 Hz, 1H), 7.64 (d, J=1.5 Hz, 1H), 7.59-7.56 (m, 1H), 7.44-7.34 (m, 4H), 7.34-7.21 (m, 6H), 6.88-6.81 (m, 1H), 5.84 (d, J=5.0 Hz, 1H), 5.54 (s, 1H), 4.61-4.54 (m, 1H), 4.42 (d, J=2.5 Hz, 1H), 4.24 (s, 1H), 4.14-3.93 (m, 3H). LC-MS, [M+H]$^+$=573.9, {Method C: $t_R$=3.452 min}.

Step 3: Synthesis of ethyl 2-(((4aR,6R,7R,8S,8aR)-6-((3,4-dichlorophenyl)thio)-8-(4-(3-fluorophenyl)-1H-imidazol-1-yl)-2-phenylhexahydropyrano[3,2-d][1,3]dioxin-7-yl)oxy)acetate: Prepared in a similar fashion as described in Example 1, step 7 using (4aR,6R,7R,8R,8aR)-6-((3,4-dichlorophenyl)thio)-8-(4-(3-fluorophenyl)-1H-imidazol-1-yl)-2-phenylhexahydropyrano[3,2-d][1,3]dioxin-7-ol (75 mg, 0.131 mmol) as the reactant to afford ethyl 2-(((4aR,6R,7R,8S,8aR)-6-((3,4-dichlorophenyl)thio)-8-(4-(3-fluorophenyl)-1H-imidazol-1-yl)-2-phenylhexahydropyrano[3,2-d][1,3]dioxin-7-yl)oxy)acetate (52 mg, 0.075 mmol, 58%) as brown solid. LC-MS, [M+H]$^+$=661.2, {Method C: $t_R$=3.732 min}.

Step 4: Synthesis of ethyl 2-(((2R,3R,4S,5R,6R)-2-((3,4-dichlorophenyl)thio)-4-(4-(3-fluorophenyl)-1H-imidazol-1-yl)-5-hydroxy-6-(hydroxymethyl)tetrahydro-2H-pyran-3-yl)oxy)acetate: Prepared in a similar fashion as described in Example 1, step 9 using ethyl 2-(((4aR,6R,7R,8S,8aR)-6-((3,4-dichlorophenyl)thio)-8-(4-(3-fluorophenyl)-1H-imidazol-1-yl)-2-phenylhexahydropyrano[3,2-d][1,3]dioxin-7-yl)oxy)acetate (50 mg, 0.076 mmol) as the reactant to afford ethyl 2-(((2R,3R,4S,5R,6R)-2-((3,4-dichlorophenyl)thio)-4-(4-(3-fluorophenyl)-1H-imidazol-1-yl)-5-hydroxy-6-(hydroxymethyl)tetrahydro-2H-pyran-3-yl)oxy)acetate (40 mg, 74%) which was as such taken for next step without further purification. LC-MS, [M+H]+=573.2, {Method C: $t_R$=2.764 min}.

Step 5: Synthesis of 2-(((2R,3R,4S,5R,6R)-2-((3,4-dichlorophenyl)thio)-4-(4-(3-fluorophenyl)-1H-imidazol-1-yl)-5-hydroxy-6-(hydroxymethyl)tetrahydro-2H-pyran-3-yl)oxy)acetic acid: Prepared in a similar fashion as described in Example 19 using ethyl 2-(((2R,3R,4S,5R,6R)-2-((3,4-dichlorophenyl)thio)-4-(4-(3-fluorophenyl)-1H-imidazol-1-yl)-5-hydroxy-6-(hydroxymethyl)tetrahydro-2H-pyran-3-yl)oxy)acetate (40 mg, 0.070 mmol) as the reactant. The crude material was purified by prep-HPLC Method A to afford Example 63 2-(((2R,3R,4S,5R,6R)-2-((3,4-dichlorophenyl)thio)-4-(4-(3-fluorophenyl)-1H-imidazol-1-yl)-5-hydroxy-6-(hydroxymethyl)tetrahydro-2H-pyran-3-yloxy)acetic acid (9.1 mg, 0.017 mmol, 24%). LC-MS, [M+H]+=543.1, {Method A: $t_R$=1.184 min}. $^1$H NMR (400 MHz, METHANOL-d4) δ 8.20 (s, 1H), 7.88 (s, 1H), 7.82 (d, J=2.0 Hz, 1H), 7.58-7.45 (m, 4H), 7.41-7.34 (m, 1H), 7.02-6.94 (m, 1H), 6.20 (d, J=5.4 Hz, 1H), 4.78 (dd, J=5.3, 11.1 Hz, 1H), 4.59 (dd, J=2.6, 11.4 Hz, 1H), 4.44 (t, J=6.0 Hz, 1H), 4.16 (d, J=2.0 Hz, 1H), 4.14-3.99 (m, 2H), 3.76-3.64 (m, 2H). hGal3 IC$_{50}$=1.56 uM.

It will be evident to one skilled in the art that the present disclosure is not limited to the foregoing illustrative examples, and that it can be embodied in other specific forms without departing from the essential attributes thereof. The examples therefore should be considered in all respects as illustrative and not restrictive, reference being made to the appended claims, rather than to the foregoing examples, and all changes which come within the meaning and range of equivalency of the claims are therefore intended to be embraced.

We claim:
1. A compound of formula I

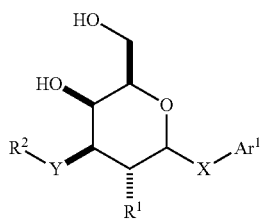

where:
Ar$^1$ is phenyl and is substituted with 0-5 substituents selected from cyano, halo, alkyl, haloalkyl, alkoxy, and haloalkoxy;
Ar$^2$ is phenyl or pyridinyl and is substituted with 0-5 substituents selected from cyano, halo, alkyl, (R$^3$)alkyl, haloalkyl, cycloalkyl, (R$^3$)cycloalkyl, alkoxy, cycloalkoxy, haloalkoxy, and alkoxycarbonyl;
R$^1$ is hydrogen, halo, alkoxy, cyanoalkoxy, hydroxyalkoxy, alkoxyalkoxy, (R$^4$)alkoxy, or (R$^4$)alkenyloxy;
R$^2$ is alkyl, cycloalkyl, alkoxycarbonyl, carboxy, CON(R$^{12}$)(R$^{13}$), or Ar$^2$;
R$^3$ is cyano, halo, alkoxy, or (R$^5$)(R$^6$)N;
R$^4$ is (R$^7$)(R$^8$)N, CO$_2$(R$^9$), or CON(R$^{10}$)(R$^{11}$);
R$^5$ is hydrogen or alkyl;
R$^6$ is hydrogen or alkyl;
or (R$^5$)(R$^6$)N taken together is azetidinyl, pyrrolidinyl, piperidinyl, piperazinyl, morpholinyl, thiomorpholinyl, (oxo)thiomorpholinyl, (dioxo)thiomorpholinyl, homopiperidinyl, or homopiperazinyl;
R$^7$ is hydrogen or alkyl;
R$^8$ is hydrogen or alkyl;
or (R$^7$)(R$^8$)N taken together is azetidinyl, pyrrolidinyl, piperidinyl, piperazinyl, morpholinyl, or morpholinyl-N-oxide;
R$^9$ is hydrogen or alkyl;
R$^{10}$ is hydrogen, alkyl, hydroxyalkyl, alkoxyalkyl, or spiro[3.3]heptanol;
R$^{11}$ is hydrogen, alkyl, hydroxyalkyl, or alkoxyalkyl;
or (R$^{10}$)(R$^{11}$)N taken together is azetidinyl, pyrrolidinyl, piperidinyl, piperazinyl, morpholinyl, thiomorpholinyl, (oxo)thiomorpholinyl, (dioxo)thiomorpholinyl, homopiperidinyl, or homopiperazinyl, and is substituted with 0-4 substituents selected from halo, alkyl, hydroxyalkyl, alkoxyalkyl, hydroxy, alkoxy, oxo, and acetamido;

$R^{12}$ is hydrogen, alkyl, or cycloalkyl;

$R^{13}$ is hydrogen or alkyl;

or $(R^{12})(R^{13})N$ taken together is azetidinyl, pyrrolidinyl, piperidinyl, piperazinyl, or morpholinyl, and is substituted with 0-3 substituents selected from halo and alkyl;

X is S, SO, or $SO_2$; and

Y is imidazolyl or triazolyl;

or a pharmaceutically acceptable salt thereof.

2. A compound of claim 1 where $Ar^1$ is phenyl or pyridinyl, and is substituted with 0-5 substituents selected from cyano, halo, alkyl, haloalkyl, alkoxy, and haloalkoxy; $Ar^2$ is phenyl or pyridinyl and is substituted with 0-5 substituents selected from cyano, halo, alkyl, $(R^3)$alkyl, haloalkyl, cycloalkyl, $(R^3)$cycloalkyl, alkoxy, cycloalkoxy, haloalkoxy, and alkoxycarbonyl; $R^1$ is alkoxy, or $(R^4)$alkoxy; and $R^2$ is $Ar^2$.

3. A compound of claim 1 where $Ar^1$ is phenyl substituted with 0-5 substituents selected from cyano, halo, alkyl, haloalkyl, alkoxy, and haloalkoxy; $Ar^2$ is phenyl substituted with 0-5 substituents selected from cyano, halo, alkyl, haloalkyl, alkoxy, and haloalkoxy; and $R^1$ is alkoxy, cyanoalkoxy, alkoxyalkoxy, or $(R^3)$alkoxy; or a pharmaceutically acceptable salt thereof.

4. A compound of claim 1 where $Ar^2$ is phenyl substituted with 3 halo substituents.

5. A compound of claim 1 where $R^1$ is alkoxy or $(R^4)$alkoxy.

6. A compound of claim 1 where Y is triazolyl.

7. A compound of claim 1 selected from the group consisting of

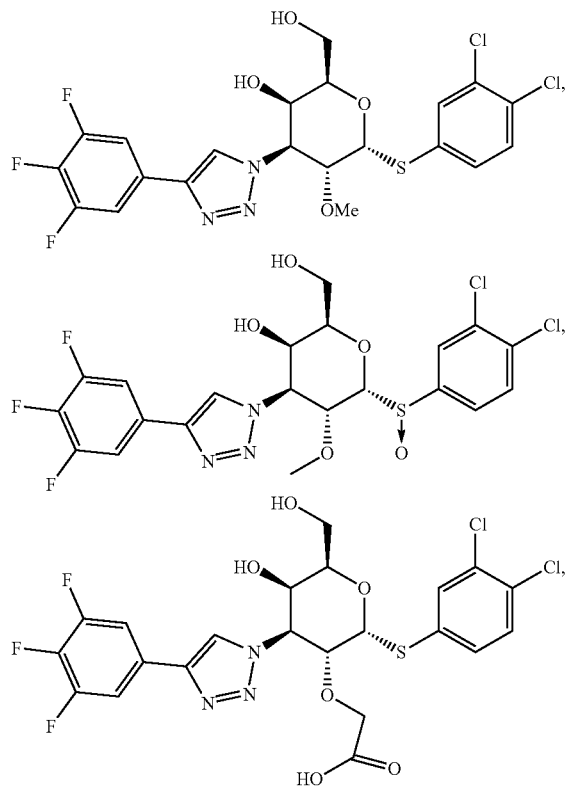

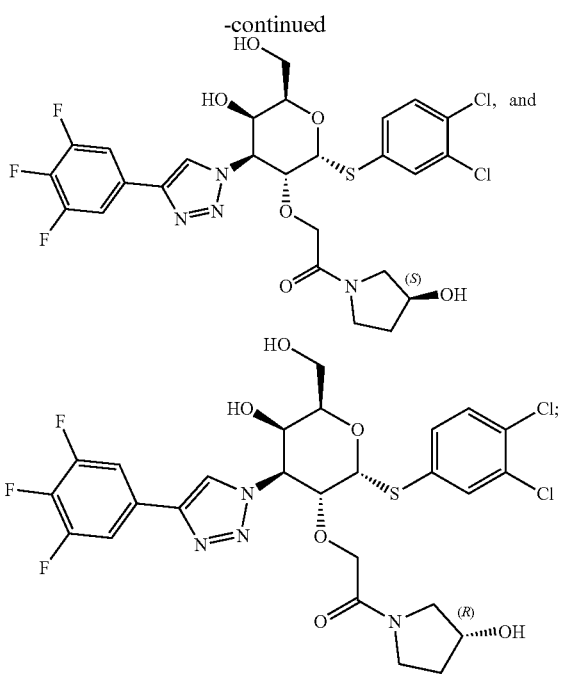

or a pharmaceutically acceptable salt thereof.

8. A composition comprising a therapeutically effective amount of a compound of claim 1, or a pharmaceutically acceptable salt thereof, and a pharmaceutically acceptable carrier.

9. A method for treating liver fibrosis, kidney fibrosis, lung fibrosis, heart fibrosis, skin fibrosis, acute hepatitis, chronic hepatitis, liver fibrosis, liver cirrhosis, portal hypertension, regenerative failure, non-alcoholic steatohepatitis, liver hypofunction, hepatic blood flow disorder, solid tumor, solid tumor metastasis, vascular fibroma, myeloma, multiple myeloma, Kaposi's sarcoma, leukemia, chronic lymphocytic leukemia, invasive metastasis of cancer cell, psoriasis, nephropathy, pneumonia, irritable bowel syndrome, inflammatory bowel disease, abnormal pancreatic secretion, neuropathic pain, peripheral neuropathy, age-related macular degeneration, or diabetic retinopathy, comprising administering a therapeutically effective amount of a compound of claim 1, or a pharmaceutically acceptable salt thereof, to a patient.

10. A method for treating renal fibrosis, pulmonary fibrosis, hepatic fibrosis, arterial fibrosis, or systemic sclerosis, comprising administering a therapeutically effective amount of a compound of claim 1, or a pharmaceutically acceptable salt thereof, to a patient.

11. A composition comprising a therapeutically effective amount of a compound of claim 2, or a pharmaceutically acceptable salt thereof, and a pharmaceutically acceptable carrier.

12. A composition comprising a therapeutically effective amount of a compound of claim 3, or a pharmaceutically acceptable salt thereof, and a pharmaceutically acceptable carrier.

13. A composition comprising a therapeutically effective amount of a compound of claim 4, or a pharmaceutically acceptable salt thereof, and a pharmaceutically acceptable carrier.

14. A composition comprising a therapeutically effective amount of a compound of claim 5, or a pharmaceutically acceptable salt thereof, and a pharmaceutically acceptable carrier.

15. A composition comprising a therapeutically effective amount of a compound of claim 6, or a pharmaceutically acceptable salt thereof, and a pharmaceutically acceptable carrier.

16. A composition comprising a therapeutically effective amount of a compound of claim 7, or a pharmaceutically acceptable salt thereof, and a pharmaceutically acceptable carrier.

17. A method for treating liver fibrosis, kidney fibrosis, lung fibrosis, heart fibrosis, skin fibrosis, acute hepatitis, chronic hepatitis, liver fibrosis, liver cirrhosis, portal hypertension, regenerative failure, non-alcoholic steatohepatitis, liver hypofunction, hepatic blood flow disorder, solid tumor, solid tumor metastasis, vascular fibroma, myeloma, multiple myeloma, Kaposi's sarcoma, leukemia, chronic lymphocytic leukemia, invasive metastasis of cancer cell, psoriasis, nephropathy, pneumonia, irritable bowel syndrome, inflammatory bowel disease abnormal pancreatic secretion, neuropathic pain, peripheral neuropathy, age-related macular degeneration, or diabetic retinopathy, comprising administering a therapeutically effective amount of a compound of claim 6, or a pharmaceutically acceptable salt thereof, to a patient.

18. A method for treating renal fibrosis, pulmonary fibrosis, hepatic fibrosis, arterial fibrosis, or systemic sclerosis, comprising administering a therapeutically effective amount of a compound of claim 6, or a pharmaceutically acceptable salt thereof, to a patient.

19. A method for treating liver fibrosis, kidney fibrosis, lung fibrosis, heart fibrosis, skin fibrosis, acute hepatitis, chronic hepatitis, liver fibrosis, liver cirrhosis, portal hypertension, regenerative failure, non-alcoholic steatohepatitis, liver hypofunction, hepatic blood flow disorder, solid tumor, solid tumor metastasis, vascular fibroma, myeloma, multiple myeloma, Kaposi's sarcoma, leukemia, chronic lymphocytic leukemia, invasive metastasis of cancer cell, psoriasis, nephropathy, pneumonia, irritable bowel syndrome, inflammatory bowel disease abnormal pancreatic secretion, neuropathic pain, peripheral neuropathy, age-related macular degeneration, or diabetic retinopathy, comprising administering a therapeutically effective amount of a compound of claim 7, or a pharmaceutically acceptable salt thereof, to a patient.

20. A method for treating renal fibrosis, pulmonary fibrosis, hepatic fibrosis, arterial fibrosis, or systemic sclerosis, comprising administering a therapeutically effective amount of a compound of claim 7, or a pharmaceutically acceptable salt thereof, to a patient.

* * * * *

UNITED STATES PATENT AND TRADEMARK OFFICE
CERTIFICATE OF CORRECTION

PATENT NO. : 11,072,626 B2
APPLICATION NO. : 16/754381
DATED : July 27, 2021
INVENTOR(S) : Prasada Jalagam et al.

Page 1 of 1

It is certified that error appears in the above-identified patent and that said Letters Patent is hereby corrected as shown below:

In the Claims

<u>Column 75</u>
Line 1, Claim 2 after "phenyl" delete "or pyridinyl,".

Signed and Sealed this
Fourth Day of January, 2022

Drew Hirshfeld
*Performing the Functions and Duties of the
Under Secretary of Commerce for Intellectual Property and
Director of the United States Patent and Trademark Office*